United States Patent [19]
Gormley et al.

[11] Patent Number: 5,994,362
[45] Date of Patent: *Nov. 30, 1999

[54] METHOD OF TREATMENT FOR PROSTATIC CANCER

[75] Inventors: Glenn J. Gormley; Elizabeth Stoner, both of Westfield, N.J.

[73] Assignee: Merck & Co., Inc., Rahway, N.J.

[ * ] Notice: This patent is subject to a terminal disclaimer.

[21] Appl. No.: 08/459,063

[22] Filed: Jun. 2, 1995

Related U.S. Application Data

[63] Continuation of application No. 08/094,950, Dec. 27, 1993, abandoned, which is a continuation of application No. 07/846,154, Mar. 11, 1992, abandoned.

[51] Int. Cl.$^6$ .................. A61K 31/44; A61K 31/275
[52] U.S. Cl. ........................... 514/284; 514/522
[58] Field of Search ...................... 514/284, 522

[56] References Cited

U.S. PATENT DOCUMENTS

| | | | |
|---|---|---|---|
| 4,039,669 | 8/1977 | Beyler et al. | 424/243 |
| 5,175,155 | 12/1992 | Juniewicz et al. | 514/176 |
| 5,300,294 | 4/1994 | Johnson | 424/423 |
| 5,593,981 | 1/1997 | Labrie | 514/170 |
| 5,595,985 | 1/1997 | Labrie | 514/169 |
| 5,610,150 | 3/1997 | Labrie et al. | 514/170 |

FOREIGN PATENT DOCUMENTS

| | | |
|---|---|---|
| 0 200 859 | 12/1986 | European Pat. Off. . |
| 0 285 383 | 5/1988 | European Pat. Off. . |
| WO 92/00010 | 9/1992 | WIPO . |

OTHER PUBLICATIONS

Labrie et al., Endocrinology 128(3) 1991, pp. 1673–1675, "Combination of an antiandrogen and a 5alpha–reductase inhibitor" .

Andriole et al., The Prostate 10 (1987), pp. 189–197, "The effect of 4MA, a potent inhibitor of 5alpha–reductase, on the growth of androgen–responsive human genitourinary tumors . . . ".

Liang et al., J. of Biol. Chem., 256(15), 1981, pp. 7998–8005, "Inhibition of 5alpha–reductase, receptor binding, and nuclear uptake of androgens in the prostate . . . ".

Petrow et al, Steroids 38(2), 1981, pp. 121–140, "Prostatic cancer. I. 6–methylene–4–pregnen–3–ones as irreversible inhibitors of rat prostatic . . . ".

Ito et al, J. Pharm. Pharmacol. 41 (1989), pp. 488–489, "A new approach to prostate cancer".

Kadohama et al., JNCL, vol. 74(2), 1984, pp. 475–486, "Retardation of prostate tumor progression in the noble rat by 4–methyl–4–aza–steroidal inhibitors of 5alpha–reductase".

Raynaud et al., Bull. Cancer (Paris), vol. 73(1), 1986, pp. 36–46, "Cancer de la prostate" Bases biologiques pour l'emploi d'un antiandrogene dans le traitement.

Petrow et al., The Prostate, vol. 9, 1986, pp. 343–361, "The dihydrotestosterone (DHT) hypothesis of prostate cancer and its therapeutic implications".

Petrow et al., The Prostatic Cell: Structure and Function, Part B, (1981), pp. 283–296, "Studies on a 5alpha–reductase inhibitor and their therapeutic implications".

Sandberg et al., Progress in Cancer Research and Therapy, vol. 31 (1984), pp. 477–489, "Enzymatic and receptor systems as targets for therapy of prostatic cancer".

Isaacs et al., The Prostate, 1989, pp. 33–40, "Experimental studies on optimal therapy for prostatic cancer".

Stone et al., The Prostate, 1986, pp. 311–318, "Estrogen formation in human prostatic tissue from patients with and without benign prostatic hyperplasia".

Olea et al., Endocrinology 126(3), 1990, pp. 1457–1463, "The proliferative effect of 'anti–androgens' on the androgen–sensitive human prostate cell line LNCaP".

Furr et al., UK. European Urology (1990) 18 Suppl., 3, pp. 2–9.

Pode et al., European Urology (1990) 18 Suppl 1, p. 177.

*Primary Examiner*—Jerome D. Goldberg
*Attorney, Agent, or Firm*—Catherine D. Fitch; Melvin Winokur

[57] ABSTRACT

Disclosed is a new treatment for men with prostatic cancer involving combination therapy of a 5α-reductase inhibitor, i.e., a 17β-substituted 4-azasteroid, a 17β-substituted non-azasteroid, 17β-acyl-3-carboxyandrost-3,5-diene, benzoylaminophenoxybutanoic acid derivative, fused benz(thio) amide or cinnamoylamide derivative, aromatic 1,2-diethers or thioethers, aromatic ortho acylaminophenoxy alkanoic acids, ortho thioalkylacylamino-phenoxy alkanoic acids, pharmaceutically acceptable salts and esters thereof, and particularly finasteride, in combination with an antiandrogen, i.e. flutamide. Pharmaceutical compositions useful for treatment are also disclosed.

3 Claims, No Drawings

METHOD OF TREATMENT FOR PROSTATIC CANCER

This is a continuation of application Ser. No. 08/094,950 filed Dec. 27, 1993 now abandoned which is a continuation of application Ser. No. 07/846,154, filed Mar. 11, 1992 now abandoned.

BACKGROUND OF THE INVENTION

This invention relates to a new method of treatment for patients, i.e. men having prostatic cancer, which treatment involves a combination therapy of administering therapeutically effective amounts of a 5α-reductase inhibitor in combination with an antiandrogenic agent.

BACKGROUND OF THE INVENTION

Prostate cancer is the second most common cancer occurring among males and the third leading cause of cancer deaths in males over 50. Most prostate cancers exhibit some degree of androgen dependence. Eunuchs do not develop prostate cancer suggesting a hormonal role for prostate cancer. Charles Huggins, et al., established conclusively that androgens play a pivotal role in prostate cancer and that surgical or medical castration of affected men often causes at least temporary regression of the tumor. (See Cancer Research 1, pp. 293–297 (1941).)

It is known that testosterone (T) is secreted by the testes and adrenal glands but can undergo a 5α-reductase mediated conversion to dihydrotestosterone (DHT) in peripheral sites including the liver, skin, and prostate. DHT is preferentially bound by the nucleus of prostatic cells and so it is generally accepted that DHT, rather than T, is the androgen required by the prostate for its growth and function.

Finasteride, 17β(N-t-butyl)carbamoyl-4-aza-5α-androst-1-en-3-one was developed as the culmination of a search for compounds which would inhibit 5α-reductase and thus have the potential for being useful against benign prostatic hyperplasia. Finasteride is a 4-azasteroid and a competitive inhibitor of the enzyme. It shows no affinity for the androgen receptor and so would not be expected to interfere with the binding and action of T in those tissues, such as muscle, which respond to T.

However, these above studies do not provide information on whether finasteride is an effective and safe agent in the treatment of prostatic cancer.

There are several methods described in the prior art for treating prostatic cancer and related prostatic disorders, for example:

U.S. Pat. No. 4,472,382 (Labrie, et al.), discloses that prostate adenocarcinoma, benign prostate hypertrophy and hormone-dependent mammary tumors may be treated with various LH-RH agonists and that prostate adenocarcinoma and benign hypertrophy may be treated by use of various LH-RH agonists and an antiandrogen.

U.S. Pat. No. 4,659,695 (Labrie), discloses a method of treatment of prostate cancer in susceptible male animals including humans whose testicular hormonal secretions are blocked by surgical or chemical means, e.g., by use of an LH-RH agonist, e.g., [D-Trp$^6$, des-Gly-NH$_2$$^{10}$]LH-RH ethylamide which comprises administering an antiandrogen, e.g., flutamide in association with at least one inhibitor of sex steroid biosynthesis, e.g., aminoglutethimide and/or ketoconazole.

U.S. Pat. No. 3,995,060 (Neri, et al.), discloses methods of preparing certain antiandrogens including 4'-substituted and 3',4'-disubstituted anilides, e.g. flutamide, and their use in treating androgen-dependent or androgen-caused disease states, such as prostatic andenocarcinoma, benign prostate hypertrophy, hirsutism, and acne, in mammals, including man.

U.S. Pat. No. 4,895,715 (Neri, et al.), discloses methods for treating androgen-dependent gynecomestia in patients being treated for diseases such as benign prostatic hypertrophy involving the combination therapy of an antiandrogen, i.e. flutamide with an antiestrogen, or an aromatase inhibitor.

However, none of these methods suggest or employ a 5α-reductase inhibitor alone or in combination with another agent.

In addition to DHT, there are other androgens such as testosterone (T) which are also active in the prostate by participating in binding to androgen receptors. It is known that antiandrogen agents, i.e. the non-steroidal flutamide, being 4'-nitro-3'-trifluoromethyl-isobutyranilide, are effective as competitive agents in binding to the androgen receptors, thus blocking the adverse action of androgens in androgen-dependent disease states. (See U.S. Pat. No. 3,995,060 to Neri, Supra.)

It is further known that, in the early stages of prostatic cancer prostatic tumors are androgen-dependent for growth. One of the most important androgens in this respect is dihydrotestosterone (DHT). The production of DHT in the prostate by the enzymic action of 5α-reductase on testosterone can be blocked by the use of e.g., 4-aza steroids, as 5α-reductase inhibitors, which are known in the art. (See Merck U.S. Pat. No. 4,760,071.) Further, it is believed that testosterone, also an androgen, may have characteristics required by prostatic tumors.

Thus, the combined effect of a 5α-reductase inhibitor in inhibiting DHT production in the prostate and the androgen receptor blocking action of an antiandrogen, i.e. flutamide, will produce a greater effect on suppressing the growth, spread and metastasis of prostatic tumors then either agent by itself.

SUMMARY OF THE INVENTION

By this invention there is provided a method of treating prostatic cancer patients who are in need of such treatment comprising the step of administering in combination to such patients therapeutically effective amounts of a 5α-reductase inhibitor e.g. a 17β-substituted 4-azasteroid, a 17β-substituted non-azasteroid, 17β-acyl-3-carboxyandrost-3,5-diene, benzoylaminophenoxybutanoic acid derivative, fused benz(thio)amide or cinnamoylamide derivative, aromatic 1,2-diethers or thioethers, aromatic ortho acylaminophenoxy alkanoic acids, ortho thioalkylacylamino-phenoxy alkanoic acids, pharmaceutically acceptable salts and esters thereof, and particularly finasteride in combination with an antiandrogen.

BRIEF DESCRIPTION OF THE INVENTION AND PREFERRED EMBODIMENTS

In one preferred aspect, the present invention provides an effective method of treating prostate cancer in patients in need of such treating by administering therapeutically effective amounts of the antiandrogen in association with a 5α-reductase inhibitor or pharmaceutical composition thereof. The active compounds may be administered together or in any order, as discussed hereinafter.

By the term "patients in need of such treating" is meant "male patients with functioning gonads who are being treated with a 5α-reductase inhibitor in a therapeutic program designed to combat prostatic cancer and/or benign prostatic hyperplasia (BPH) and are discovered to have a stage of cancer in which the prostatic tumors are still androgen dependent.

The use of therapeutically effective amounts of the 5α-reductase inhibitor and the antiandrogen in accordance with this invention effectively treats prostatic cancer and is more effective than the use of either agent entirely by itself.

Typical suitable antiandrogens known in the art and useful and included within the scope of this invention include nonsteroidal antiandrogens such as the imidazolidines, especially 1-(3'-trifluoromethyl-4'nitrophenyl)-4,4-dimethyl-imidazoline-2,5-dione (also called Anandron) described in U.S. Pat. No. 4,097,578; 4'-nitro-3'-trifluoromethylisobutyranilide (also called flutamide) described in U.S. Pat. No. 3,847,988, hydroxyflutamide described in U.S. Pat. No. 3,875,229 and prodrug forms of hydroxyflutamide; the N-(phenylalkanoyl)aniline derivatives disclosed in U.S. Pat. No. 4,386,080; the 3,4-disubstituted-branched-chain acylanilides disclosed in U.S. Pat. No. 4,239,776 (A. T. Glen, et al.) and specifically casodex (Imperial Chemical Industries), which is N-[4-cyano-3-(trifluoromethyl) phenyl]-3-[(4-fluorophenyl) sulfonyl]-2-hydroxy-2-methyl-propionamide disclosed in U.S. Pat. No. 4,636,505 (H. Tucker).

Representative compounds of the non-steroidal antiandrogens described above are the following:

1-(3'-trifluoromethyl-4'-nitrophenyl)-4,4-dimethyl-5-iminoimidazoline-2-one;
1-(3'-trifluoromethyl-4'-nitrophenyl)-4,4-dimethyl-imidazoline-2,5-dione;
ethyl N-(4-nitro-3-trifluoromethylphenyl)-cyclopropylcarbimidate;
ethyl N-(4-nitro-3-trifluoromethylphenyl)-isobutyrimidate;
ethyl N-(4-iodo-3-trifluoromethylphenyl)-isobutyrimidate;
ethyl N-(4-nitro-3-trifluoromethylphenyl)-2.3-dimethylbutyrimidate;
ethyl N-(4'-nitro-3'trifluoromethylphenyl)-2-methylbutyrimidate;
ethyl N-(4-bromo-3-trifluoromethylphenyl)-isobutyrimidate;
ethyl N-(4-nitrophenyl)-isobutyrimidate;
ethyl N-(4-chloro-3-trifluoromethylphenyl)-isobutyrimidate;
ethyl N-(3-bromo-4-nitrophenyl)-isobutyrimidate;
ethyl N-(3-chloro-4-nitrophenyl)-isobutyrimidate;
N-(4-Nitro-3-trifluoromethylphenyl) isobutyrchlorimidate;
4-Nitro-3-trifluoromethylisobutyrthioanilide;
Ethyl N-(4-nitro-3-trifluoromethylphenyl)-isobutyrimidate;
Methyl N-(4-nitro-3-trifluoromethylphenyl)-2-hydroxyisobutyrimidate;
2-bromo-4'-nitro-3'-trifluoromethylisobutyranalide;
2-methoxy,2-fluoro-2-chloro-3'-trifluoromethylisobutyranilide;
2-iodo-4'-nitro-3'trifluoromethylisobutyranilide;
N-methyl-2-bromo-4'-nitro-3'-trifluoromethylisobutyranilide;
N-ethyl-2-bromo-4'-nitro-3'-trifluoromethylisobutyranilide;
N-propyl-2-bromo-4'-nitro-3'-trifluoromethylisobutyranilide;
N-butyl-2-bromo-4'-nitro-3'-trifluoromethylisobutyranilide;
2-hydroxy-4'-nitro-3'-trifluoromethylisobutyranilide;
3',4'dinitro-2-hydroxyisovaleranilide;
4'-chloro-2-hydroxy-3'-trifluoromethylcyclobutylcarbanilide;
3'-chloro-2-hydro-4'-iodocyclopropylcarbanilide;
3'-bromo-2-hydroxy-3-methyl-4'-nitrovaleranilide;
2-hydroxy-3'-iodo-4'-trifluoromethylisobutyranilide;
2,3-dimethyl-2-hydroxy-3'-methyl-4'-nitrovaleranilide;
3'-acetyl-2,3-dimethyl-2-hydroxy-4'-iodovaleranilide;
3'-acetyl-2,3-dimethyl-2-hydroxy-4'-nitrovaleranilide;
2-hydroxy-3'-methoxy-4'nitroisobutyranilide;
3'-ethyl-2-hydroxy-4'-trifluoromethylisobutyranilide;
2,3-dimethyl-2-hydroxy-4'-nitro-3'-trifluoromethylthiovaleranilide;
4'-chloro-2-hydroxy-3'-propylisobutyranilide;
3'-bromo-2,3-dimethyl-2-hydroxy-4'-trifluoromethylcyclopropylcarbanilide;
2-hydroxy-4'-nitrobutyranilide;
2-hydroxy-3'-nitro-4'-bromoisobutyranilide;
4'-chloro-2-hydroxy-3'-iodoisovaleranilide;
2-bromo-4'-nitrocyclopropylcarbanilide;
2,3-dimethyl-2-hydroxy-3'-propionyl-4'-trifluoromethylbutyranilide;
2,3-dimethyl-2-hydroxy-3'-propionyl-4'-nitrobutyranilide;
2-hydroxy-4'-trifluoromethylisobutyranilide;
2-hydroxy-4'-nitro-3'-trifluoromethylisovaleranilide;
2-hydroxy-2-methyl-4'-nitro-3'-trifluoromethylbutyranilide;
2-hydroxy-3'-4'-dichloroisobutyranilide;
2-hydroxy-3'-4'-diiodoisobutyranilide;
3'-fluoro-2-hydroxy-4'-nitroisobutyranilide;
2-hydroxy-4'-chloro-3'-trifluoromethylisobutyranilide;
2-hydroxy-4'-nitroisobutyranilide;
2-ethyl-2-hydroxy-4'-nitro-3'-trifluoromethylbutyranilide;
3'-bromo-2-hydroxy-4'-nitroisobutyranilide;
2,3-dimethyl-2-hydroxy-4'-nitro-3'-trifluoromethylbutyranilide;
2-hydroxy-N-methyl-4'-nitro-3'-trifluoromethylisobutyranilide;
4'-chloro-2-hydroxy-N-methyl-3'-trifluoromethylisobutyranilide;
4'-bromo-2-hydroxy-3'-trifluoromethylisobutyranilide;
2,3-dimethyl-2-hydroxy-4'-nitro-3'-trifluoromethylbutyranilide;
2-hydroxy-N-methyl-4'-nitro-3'-trifluoromethylisobutyranilide;
2-acetoxy-4'-nitro-3'-trifluoromethylisobutyranilide;
2-methoxy-4'-nitro-3'-trifluoromethylisobutyranilide;
2-valeryloxy-4'-nitro-3'-trifluoromethylisobutyranilide;
2-hydroxy-3'-bromo-4'-nitroisobutyranilide;
2-hydroxy-4'-bromo-3'-trifluoromethylisobutyranilide;
2-acetoxy-4'-bromo-3'-trifluoromethylisobutyranilide;
3'-bromo-2-chloro-4'-nitroisobutyranilide;
2-bromo-4'-nitro-3'-trifluoromethylisobutyranilide;
N-methyl-2-methoxy-4'-nitro-3'-trifluoromethylisobutyranilide;
4'-bromo-2-chloro-3'-trifluoromethylisobutyranilide;
2-chloro-4'-iodo-3'-trifluoromethylisobutyranilide;
2-acetoxy-4'-bromo-3'-trifluoromethylisobutyranilide;
3'-chloro-2-hydroxy-4'-nitroisobutyranilide;
4'-bromo-2-methoxy-3'-trifluoromethylisobutyranilide;
2-chloro-4'-nitro-3'-trifluoromethylisobutyranilide;
2-hydroxy-4'-chloro-3'-trifluoromethylisobutyranilide;
2-hydroxy-4'-nitro-3'-trifluoromethylcyclopropylcarbanilide;
2-hydroxy-4'-iodo-3'-trifluoromethylcyclopropylcarbanilide;
2,3-dimethyl-2-hydroxy-4'-nitro-3'-trifluoromethylbutyranilide;
2-hydroxy-4'-nitro-3'-trifluoromethylisovaleranilide;
4'-bromo-2-hydroxy-3'-trifluoromethylisobutyranilide;
2'-hydroxy-4'-nitroisobutyranilide;
4'-chloro-2-hydroxy-3'-trifluoromethylisobutyranilide;

3'-bromo-2-hydroxy-4'-nitroisobutyranilide;
3'-chloro-2-hydroxy-4'-nitroisobutyranilide;
2-chloro-4'-nitro-3'-trifluoromethyl-cyclopropylcarbanilide;
2-chloro-4'nitro-3'-iodo-3'-trifluoromethylbutyranilide;
2-chloro-4'-nitro-3'-trifluoromethylcyclopropylcarbanilide;
2-chloro-4'-nitro-3'-trifluoromethyl-isobutyranilide;
2-chloro-2,3-dimethyl-4'iodo-3'-trifluoromethylbutyranilide;
2-chloro-4'-nitro-3'-trifluoromethylisovaleranilide;
4'-bromo-2-chloro-3'-trifluoromethylisovaleranilide;
4'-bromo-2-chloro-3'-trifluoromethylisobutyranilide;
2-chloro-4'-nitroisobutyranilide;
2,4'-dichloro-3'-trifluoromethylisobutyranilide;
3'-bromo-2-chloro-4'-nitroisobutyranilide;
2,3'-dichloro-4'-nitroisobutyranilide;
4'-Nitro-3'-trifluoromethyl-2-valeryloxyisobutyranilide;
3,4-dichloro-N-(2-hydroxy-2-p-nitrophenylpropionyl)aniline;
4-nitro-3-trifluoromethyl-N-(2-hydroxy-2-p-nitrophenylpropionyl)aniline;
4-cyano-3-trifluoromethyl-N-(2-hydroxy-2-p-nitrophenylpropionyl)aniline;
3-chloro-4-nitro-N-(2-hydroxy-2-p-nitrophenylpropionyl)aniline;
3-chloro-4-methylsulphonyl-N-(2-hydroxy-2-p-nitrophenylpropionyl)aniline;
4-nitro-3-trifluoromethyl-N-(2-hydroxy-2-p-trifluoromethylphenylpropionyl)aniline;
3-chloro-4-nitro-N-(2-hydroxy-2-p-trifluoromethylphenylpropionyl)aniline;
4-nitro-3-trifluoromethyl-N-(2-p-cyanophenyl-2-hydroxypropionyl)aniline;
4-nitro-3-trifluoromethyl-N-(2-p-fluorophenyl-2-hydroxypropionyl)aniline;
4-nitro-3-trifluoromethyl-N-(2-hydroxy-2-p-methylsulphinylphenylpropionyl)aniline;
3,4-dichloro-N-(2-hydroxy-2-p-methylsulphinylphenylpropionyl)aniline;
3,4-dichloro-N-(2-p-acetylphenyl-2-hydroxypropionyl)aniline;
3,4,5,-trichloro-N-(2-hydroxy-2-p-nitrophenylpropionyl)aniline;
2-chloro-4-nitro-N-(2-hydroxy-2-p-nitrophenylpropionyl)aniline;
N-(2-methoxy-2-p-nitrophenylpropionyl)-4-nitro-3-trifluoromethylaniline;
N-(2-n-butoxy-2-p-nitrophenylpropionyl)-4-nitro-3-trifluoromethylaniline;
4-nitro-3-trifluoromethyl-N-(2-p-nitrophenylpropionyl)aniline;
4-nitro-3-trifluoromethyl-N-(2-hydroxy-2-p-methanesulphinylphenylpropionyl)aniline;
4-nitro-3-trifluoromethyl-N-(2-hydroxy-2-p-methanesulphonylphenylpropionyl)aniline;
4-nitro-3-trifluoromethyl-N-(3-chloro-2-hydroxy-2-p-nitrophenylpropionyl)aniline;
3,4-dichloro-N-(3-chloro-2-hydroxy-2-nitrophenylpropionyl)aniline;
3-chloro-4-cyano-N-(3-chloro-2-hydroxy-2-p-nitrophenylpropionyl)aniline;
3,4-dichloro-N-(2-hydroxy-2-p-methoxycarbonylphenylpropionyl)aniline;
5-methyl-5-p-nitrophenyl-3-(4-nitro-3-trifluoromethylphenyl)oxazolidine-2,4-dione;
3,4-dicyanoisobutyrylanilide;
3,4-dicyano-(2-hydroxy-2-methylpropionyl)anilide;
3,4-dicyano-N-methylisobutyrylanilide;
3,4-dicyano-(2-methoxy-2-methylpropionyl)anilide;
4-cyano-3-trifluoromethyl-(2-hydroxy-2-methylpropionyl)anilide;
3,4-dicyano-(2-acetoxy-2-methylpropionyl)anilide;
3,4-dicyano-(2-hydroxy-2-methylpropionyl)anilide;
3,4-dicyano-(cyclopropanecarbonyl)anilide;
3-cyano-4-nitro-(2-hydroxy-2-methylpropionyl)anilide;
3,4-dicyano-N-methylisobutyranilide;
3,4-dicyano-N-ethylisobutyranilide;
N-butyl-3,4-dicyanoisobutyranilide;
3,4-dicyano-(2-decanoyloxy-2-methylpropionyl)anilide;
3,4-dicyano-(2-hydroxy-2-methylpropionyl)anilide;
3-chloro-4-cyano-N-(3-ethylthio-2-hydroxy-2-methylpropionyl)aniline;
3-chloro-4-cyano-N-(3-ethylsulphonyl-2-hydroxy-2-methylpropionyl)aniline;
4-cyano-3-trifluoromethyl-N-(2-hydroxy-2-methyl-3-phenylsulphonylpropionyl)aniline;
4-cyano-3-trifluoromethyl-N-(3-ethylsulphonyl-2-hydroxy-2-methylproionyl)aniline;
4-nitro-3-trifluoromethyl-N-(2-hydroxy-3-phenylsulphonyl-2-methylpropionyl)aniline;
4-nitro-3-trifluoromethyl-N-(3-ethylsulphonyl-2-hydroxy-2-methylpropionyl)aniline;
3-chloro-4-nitro-N-(2-hydroxy-3-phenylthio-2-methylpropionyl)aniline;
4-nitro-3-trifluoromethyl-N-[2-hydroxy-2-methyl-3-(thiazol-2-ylthio)propionyl]aniline;
4-nitro-3-trifluoromethyl-N-[3-allylthio-2-hydroxy-2-methylpropionyl)aniline;
4-nitro-3-trifluoromethyl-N-(3-p-fluorophenylthio-2-hydroxy-2-methylpropionyl)aniline;
4-nitro-3-trifluoromethyl-N-[2-hydroxy-2-methyl-3-(pyrid-2-ylthio)propionyl]aniline;
4-nitro-3-trifluoromethyl-N-[2-hydroxy-2-methyl-3-(5-methyl-1,3,4-thiadiazol-2-ylthio)propionyl)aniline;
4-nitro-3-trifluoromethyl-N-[2-hydroxy-2-methyl-3-(4-methylthiazol-2-ylthio)propionyl]aniline;
4-nitro-3-trifluoromethyl-N-[2-hydroxy-2-methyl-3-(pyrid-2-ylsulphonyl)propionyl]aniline;
4-nitro-3-trifluoromethyl-N-(3-p-fluorophenyl-sulphonyl-2-hydroxy-2-methylpropionyl)aniline;
4-cyano-3-trifluoromethyl-N-[2-hydroxy-2-methyl-3-(thiazol-2-ylthio)propionyl]aniline;
4-cyano-3-trifluoromethyl-N-[2-hydroxy-2-methyl-3-(pyrid-2-ylthio)propionyl]aniline;
4-cyano-3-trifluoromethyl-N-(2-hydroxy-2-methyl-3-methylthiopropionyl)aniline;
4-cyano-3-trifluoromethyl-N-(3-p-fluorophenylthio-2-hydroxy-2-methylpropionyl)aniline; and
4-cyano-3-trifluoromethyl-N-(3-p-fluorophenyl-sulphonyl-2-hydroxy-2-methylpropionyl)aniline, and the like.

Typical suitable steroidal antiandrogens known in the art include cyproterone, 6-chloro-1,2-dihydro-17-(acetyl)-3'H-cyclopropa[1,2]-pregna-1,4,6-triene-3,20-dione, available under the tradename of Androcur from Schering A. G., W. Berlin. See U.S. Pat. No. 3,234,093.

The use of pure antiandrogens such as flutamide is preferred. By the term "pure antiandrogen" is meant an antiandrogen which is devoid of any androgenic, estrogenic, antiestrogenic, progestational, antiprogestational, angonadotrophic or adrenocortical activity.

Typical 5α-reductase inhibitors known in the art include the 4-aza steroids developed by Merck. (See U.S. Pat. No. 4,377,584 to Rasmusson, et al; U.S. Pat. No. 4,220,735 to Rasmusson, et al.; U.S. Pat. No. 4,845,104 to Carlin, et al; U.S. Pat. No. 4,760,071 to Rasmusson, et al., which discloses finasteride, being 17β-(N-t-butyl)carbamoyl-4-aza-5α-androst-1-en-3-one, known by its trademark as PROSCAR*; U.S. Pat. No. 4,732,897 to Cainelli, et al.; U.S. Pat. No. 4,859,681 to Rasmusson, et al.; EPO Publn. 0 155 076; EPO Publn. 0 004 949; and EPO Publn. 0 314 189.

Preferred are where the 4-aza steroid has the formula:

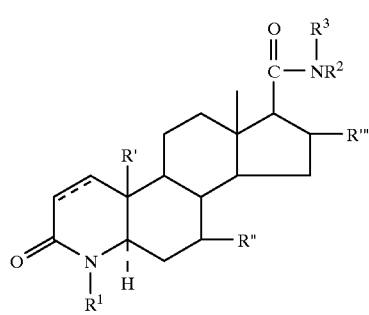

I wherein the dotted line represents a double bond when present, $R^1$ and $R^3$ are independently hydrogen, methyl or ethyl, $R^2$ is a hydrocarbon radical selected from straight or branched chain substituted or unsubstituted alkyl, cycloalkyl, or aralkyl of from 1–12 carbons or monocyclic aryl optionally containing 1 or more lower alkyl substituents of from 1–2 carbon atoms and/or 1 or more halogen substituents, R' is hydrogen or methyl, R" is hydrogen or β-methyl, R'" is hydrogen, α-methyl or β-methyl, and pharmaceutically acceptable salts or esters thereof.

A preferred embodiment of the compound of formula I applicable in the process of our invention is represented by the formula:

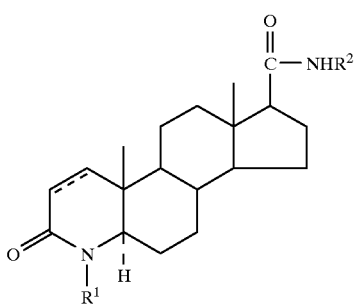

II wherein $R^1$ is hydrogen, methyl or ethyl, and $R^2$ is branched chain alkyl, cycloalkyl, aralkyl of from 4–12 carbons,
phenyl, optionally substituted by methyl, chloro or fluoro, substituted or unsubstituted 1-, 2-adamantyl, 1-, 2-adamantylmethyl, 1-, 2- or 7-norbornanyl, 1-, 2- or 7-norbornanymethyl.

Representative compounds of the present invention include the following:

17β-(N-tert-amylcarbamoyl-4-aza-5α-androst-1-en-3-one,
17β-(N-tert-hexylcarbamoyl)-4-aza-5α-androst-1-en-3-one,
17β-(N-tert-butylcarbamoyl)-4-aza-5α-androst-1-en-3-one,
17β-(N-isobutylcarbamoyl)-4-aza-5α-androst-1-en-3-one,
17β-(N-tert-octylcarbamoyl)-4-aza-5α-androst-1-en-3-one,
17β-(N-octylcarbamoyl)-4-aza-5α-androst-1-en-3-one,
17β-(N-1,1-diethylbutylcarbamoyl)-4-aza-5α-androst-1-en-3-one,
17β-(N-neopentylcarbamoyl)-4-aza-5α-androst-1-en-3-one,
17β-(N-2-adamantylcarbamoyl)-4-aza-5α-androst-1-en-3-one,
17β-(N-1-adamantylcarbamoyl)-4-aza-5α-androst-1-en-3-one,
17β-(N-2-norbornylcarbamoyl)-4-aza-5α-androst-1-en-3-one,
17β-(N-1-norbornylcarbamoyl)-4-aza-5α-androst-1-en-3-one,
17β-(N-phenylcarbamoyl)-4-aza-4-methyl-5α-androst-1-en-3-one,
17β-(N-benzylcarbamoyl)-4-aza-4-methyl-5α-androst-1-en-3-one,
17β-(N-tert-amylcarbamoyl-4-aza-4-methyl-5α-androst-1-en-3-one,
17β-(N-tert-hexylcarbamoyl)-4-aza-4-methyl-5α-androst-1-en-3-one,
17β-(N-tert-butylcarbamoyl)-4-aza-4-methyl-5α-androst-1-en-3-one,
17β-(N-isobutylcarbamoyl)-4-aza-4-methyl-5α-androst-1-en-3-one,
17β-(N-tert-octylcarbamoyl)-4-aza-4-methyl-5α-androst-1-en-3-one,
17β-(N-1,1,3,3-tetramethylbutylcarbamoyl)-4-aza-5α-androst-1-en-3-one,
17β-(N-octylcarbamoyl)-4-aza-4-methyl-5α-androst-1-en-3-one,
17β-(N-1,1-diethylbutylcarbamoyl)-4-aza-4-methyl-5α-androst-1-en-3-one,
17β-(N-neopentylcarbamoyl)-4-aza-4-methyl-5α-androst-1-en-3-one,
17β(N-1-adamantylcarbamoyl)-4-aza-5α-androstan-3-one;
17β(N-1-adamantylcarbamoyl)-4-methyl-4-aza-5α-androst-1-en-3-one;
17β(N-1-adamantylcarbamoyl)-4-methyl-4-aza-5α-androstan-3-one;
17β-(N-1-adamantylmethylcarbamoyl)-4-aza-5α-androst-1-en-3-one;
17β-(N-2-adamantylcarbamoyl)-4-aza-5α-androstan-3-one;
17β-(N-methyl-N-2-adamantylcarbamoyl)-4-methyl-4-aza-androstan-3-one;
17β-(N-2-adamantylcarbamoyl)-4-methyl-4-aza-5α-androstane-3-one;
17β-(N-2-adamantylcarbamoyl)-4-methyl-4-aza-5α-androst-1-en-3-one;
17β-(N-methyl-N-2-adamantyl)carbamoyl-4-methyl-4-aza-androst-1-en-3-one;
17β-(N-(3-methyl)-1-adamantyl-carbamoyl)-4-aza-4-methyl-5α-androst-an-3-one;
17β-(N-exo-2-norbornanylcarbamoyl)-4-aza-4-methyl-5α-androst-1-en-3-one;
17β-(N-exo-2-norbornanylcarbamoyl)-4-aza-5α-androst-1-en-3-one;17β-(N-2-adamantylcarbamoyl)-4-aza-5α-androst-en-3-one;
17β-(N-methyl-N-2-adamantylcarbamoyl)-4-aza-4-methyl-androstan-3-one;
17β-(N-2-adamantylcarbamoyl)-4-methyl-4-aza-5α-androstan-3-one; and
17β-(N-methyl-N-2-adamantyl)carbamoyl-4-methyl-4-aza-androst-1-en-3-one.

The corresponding compounds of those above wherein the 4-aza substituent is substituted in each of the above named compounds with a hydrogen, methyl or an ethyl radical, to form a different N-substituent, and wherein a double bond can be optionally present as indicated by the dotted line in position 1.

The alkyl, cycloalkyl, aralkyl, monocyclic aryl, 1-, 2-adamantyl or 1-, 2-norbornanyl moieties can be substituted with one or more substituents of the following: $C_1$–$C_4$ linear/branched alkyl, including methyl, ethyl, isopropyl, n-butyl; nitro; oxo; $C_7$–$C_9$ aralkyl, including benzyl; $(CH_2)n$ COOR where n is 0–2 and R is H or $C_1$–$C_4$ linear/branched alkyl including methyl, ethyl; $CH_2OH$; OH; OR where R is $C_1$–$C_4$ linear/branched alkyl including methyl, ethyl; halo, including fluoro, bromo, iodo; COOH; COOR, where R is linear/branched $C_1$–$C_4$ alkyl; —$CONH_2$; $CH_2NH_2$; $CH_2NHCOR$ where R is $C_1$–$C_4$ linear/branched alkyl including methyl, ethyl; phenyl; o, m, p-substituted phenyl including p-nitro, p-amino and p-sulfo; or cyano. The amino group of the adamantyl or norbornanyl moiety can also be substituted as $R^1$ with methyl and ethyl, as well as hydrogen.

Also included within the scope of this invention are pharmaceutically acceptable salts or esters, where a basic or acidic group is present on the substituted alkyl, cycloalkyl, aralkyl, adamantyl or norbornanyl moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Representative examples include for $R^2$ (where AD is adamantyl):
3,5,7-trinitro-1-AD; 4-oxo-1-AD; 1-benzyl-1-AD; 4,4-dimethyl-1-Ad; 3,7-dimethyl-5-carboxymethyl-1-AD; 3-carboxymethyl-1-AD; 3-chloro-1-AD; 1,3-dihydroxy-6,6-dimethyl-2-AD; 3-chloro-1-AD; 4-carbethoxy-2-AD; 4-carboxy-2-AD; 3-isopropyl-1-AD; 3-n-butyl-1-AD; 3-propyl-1-AD; 3-,5-diethyl-1-AD; 3-hydroxymethyl-1-AD; 2-carboxy-1-AD; 3-methyl-1-AD; 5-hydroxy-2-AD; 2-hydroxy-1-AD; 1-aminomethyl-1-hydroxy-2-AD; 2-oxo-1-AD; 2-phenyl-2-AD; 1-amino-methyl-2-AD; 1-carboxy-2-AD; 1-aminocarbonyl-2-AD; 3-hydroxy-5,7-dimethyl-1-AD; 4-fluoro-1-AD; 3-fluoro-1-AD; 4-hydroxy-2-AD; 3-phenyl-1-AD; 3-(p-aminophenyl)-1-AD; 3-(p-nitrophenyl)-1-AD; 3-methyl-5-hydroxymethyl-1-AD; 3,5-dimethyl-4-hydroxy-1-AD; 2-hydroxymethyl-2-AD; 3-(p-sulfophenyl)-1-AD; 3-methyl-5-ethyl-1-AD; 2-carboxy-2-AD; 3,5-7-trimethyl-1-AD; 4-iodo-2-AD; 4-bromo-2-AD; 4-chloro-2-AD; 1-acetylaminomethyl-2-AD; 1-carboxymethyl-2-AD; 1-methyl-2-AD; 1-aminocarboxylmethyl-2-AD; 1-aminocarboxyl-1-AD; 2-cyano-2-AD; 3,5-dimethyl- 7-ethyl-1-AD; 4-hydroxy-1-AD; 1-hydroxy-2-AD; 5-carboxy-3-methyl-1-AD; 3,5-dimethyl-7-carboxy-1-AD; 3-carboxy-1-AD; 3-hydroxy-1-AD; and the like.

Representative examples include for $R^2$ as substituted norbornanyl moieties are (where NB is norbornanyl):
2-NB; 1,7,7-trimethyl-4-phenyl-2-NB; 3-carboxy-2-NB; 3-phenyl-2-carboxy-2-NB; 2-cyano-3-phenyl-2-NB; 3-hydroxy-4,7,7-trimethyl-2-NB; 6-hydroxymethyl-2-NB; 5-cyano-2-NB; 3-allyl-2-NB; 1-NB; 7,7-dimethyl-1-hydroxymethyl-2-NB; 3-methoxy-4,7,7-trimethyl-2-NB; 3-aminocarbonyl-2-NB; 3-ethoxycarbonyl-2-NB; 3,3-dimethyl-2-NB; 7-oxo-1-NB; 3-phenyl-2-NB; 1-carboxymethyl-7,7-dimethyl-2-NB; 1-ethyl-2-NB; 1-methyl-2-NB; 2,2,3,3,5,5,6,6,7,7-decafluoro-1-NB; 3-hydroxy-2-NB; 3-chloro-2-NB; 3-(p-methoxyphenyl)-2-NB; 2,2-dimethyl-3-methylene-7-NB; 3-oxo-2-NB; 1-methoxy-2-NB; 7-NB; 3-isopropyl-2-NB; 2-bromo-1-NB; 3-chloro-1-NB; and the like.

Procedures for preparing the compounds of Formula I useful in this invention, including the above, are well known in the art.

The novel compounds of formula I of the present invention can be prepared by a method starting with the known steroid ester (III) of the formula:

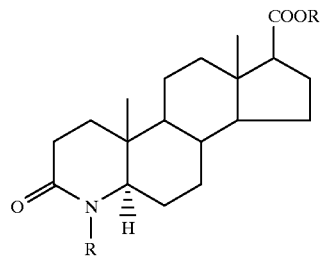

IIIA

17β-(carbomethoxy)-4-aza-5-α-androstan-3-ones which includes the stages of optionally 1) dehydrogenating said starting material to produce the corresponding compound containing a double-bond in the 1,2-position of the A-ring, 2) converting the 17-carbomethoxy substituent into an N-substituted alkyl, cycloalkyl, aralkyl, monocylic acyl, or adamantylcarbamoyl substituent and, if desired, 3) alkylating the A-ring nitrogen to introduce a N-methyl or N-ethyl substituent into the A ring 4-position. For the dehydrogenatin step, it is preferable that the 4-aza nitrogen be unsubstituted. The alternate pathways can consist of one or more discrete chemical steps and if desired can take place before step (1) or following step (1) or step (3).

In accordance with the process of the present invention (see flow sheet), the products of our invention are formed by optionally: (1) heating a 17β-alkoxycarbonyl-4-aza-5α-androstan-3-ones, compound III, (prepared in the literature as described in the reference U.S. Pat. No. 4,377,584) with a dehydrogenating agent such as benzeneseleninic anhydride in a refluxing inert solvent, e.g. chlorobenzene, to form a 17β-alkoxycarbonyl-4-aza-5α-androst-1-ene-3-one IV (alternately, the dichlorodicyanobenzoquinone process of Dolling, et al., JACS 1988, Vol. 110, pp. 3318–3319, can be used); (2) the formed 5α-androst-1-en-3-one compound from Step 1 can be reacted with, e.g. sodium hydride under anhydrous conditions in a neutral solvent such as dimethylformamide; (3) contacting the resulting reaction mixture with an alkyl (methyl or ethyl) iodide to form the corresponding 17-β-alkoxy-adamantyl-carbamoyl-4-alkyl-4-aza-5α-androst-1-en-3-one V; (4) subsequently hydrolyzing said 17β-alkoxycarbonyl-4-alkyl-4-aza-5α-androst-1-en-3-one with a strong base, such as aqueous methanolic potassium hydroxide at the reflux temperature, followed by acidification and isolation of the resulting steroidal acid to yield 17β-carboxy 4-alkyl-4-aza-5α-androst-1-en-3-one VI; (5) said steroidal acid can be then converted to its corresponding 2-pyridylthio ester by refluxing with triphenyl phosphine and 2,2'-dipyridyl disulfide in an inert solvent such as toluene and the resulting product 17β-(2-pyridylthiocarbonyl)-4-alkyl-4-aza-5α-androst-1-en-3-one VII can be isolated by chromatography on e.g. silica gel; and (6) said pyridylthio ester can be thenreacted with 1-adamantyl-, 2-adamantylamine or norbornanylamine in an inert solvent e.g. tetrahydrofuran, to form the desired product 17β-N-adamantylcarbamoyl-4-alkyl-4-aza-5α-androst-1-en-3-one VIII which can be isolated by chromatography e.g. on silica gel. When the previous reaction is carried out in the absence of first forming the double bond at position 1, the corresponding 17β-(N-adamantylcarbamoyl)- 4-alkyl-4-aza-5α-androstan-3-one (or N-norbornanyl carbamoyl compound) is prepared.

In accordance with an alternate process of our invention the corresponding N-unsubstituted-17β(N-adamantyl-carbamoyl)-4-aza-5α-androst-1-en-3-one XIV is readily prepared from the 17β (alkoxycarbonyl)-4-aza-5α-androstone-3-one IV by repeating the above series of reaction steps but omitting the alkylation Step 2 herein above, i.e. treatment of the 4-aza-5-α-androst-1-en-3-one with e.g. sodium amide followed by methyl or ethyl iodide via intermediates XII and XIII.

In accordance with a further alternate process of preparing the compounds of our invention having only hydrogen as the sole substituent on the ring A—nitrogen, the double bond in the A ring is introduced as the last step of the process. Thus, a 17β-alkoxycarbonyl 4-aza-5α-androstan-3-one III is hydrolyzed to the corresponding steroidal acid IX 17β-carboxy-4-aza-5α-androstan-3-one which in turn is converted to the corresponding pyridylthio ester, 17β (2-pyridylthiocarbonyl)-4-aza-5α-androstan-3-one, X followed by treatment of the ester with an amine of formula $R^2$-$NH_2$ wherein $R^2$ is as defined hereinabove as 1- or 2-adamantyl or 1-, 2-, or 7-norbornanyl to form a 17β (N-adamantyl-carbamoyl)-4-aza-5α-androstone-3-one XI which is dehydrogenated as previously described to produce compound XIV, 17β-(N-adamantyl-carbamoyl)-4-aza-androst-1-en-3-one or corresponding norbornanyl derivative.

In another alternate method of introducing the 17β-(N-adamantyl-carbamoyl)substituent into a 17β-carboxy androstane compound of formula VI, XII or IX, each is treated in a manner similar to the procedure described in *Steroids*, Vol. 35 #3, March 1980, p. 1–7 with dicyclohexylcarbodiimide and 1-hydroxybenzo-triazole to form the 17β-(1-benzotriazoloxycarbonyl)-4-aza-5α-androst-1-en-3-one, VII, XIII or compound X, wherein the substituent X is benzotriazoloxy group.

The 16-methyl derivative wherein R′″ is methyl are prepared from known 16-methyl-17-acyl-4-methyl-4-aza-5α-androstan-3-ones, e.g. 4,16β-dimethyl-17β-acetyl-4-aza-5α-androstan-3-one by known dehydrogenation procedures for 4-methyl-4-aza compounds to produce the corresponding 4,16β-dimethyl-17β-acetyl-4-aza-5α-androst-1-en-3-one.

The above reactions are schematically represented in the following flowsheet.

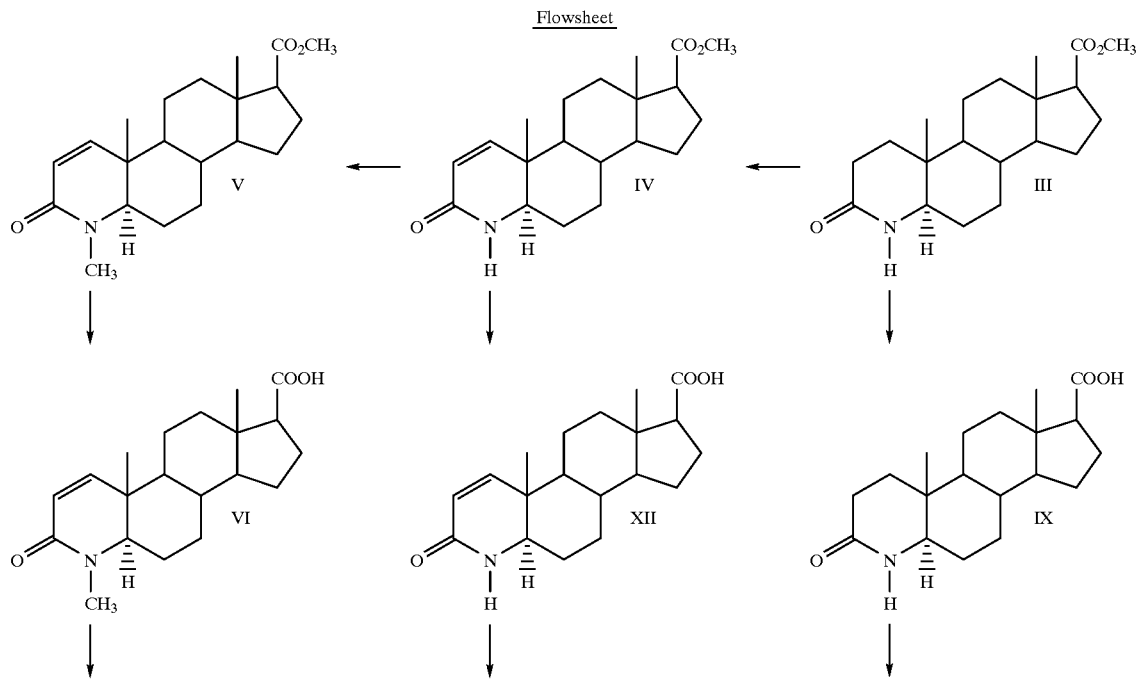

Flowsheet

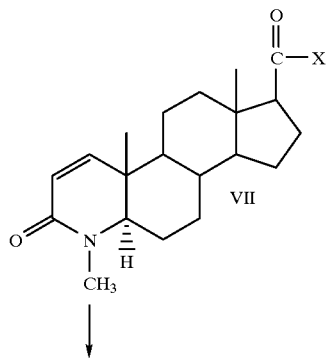 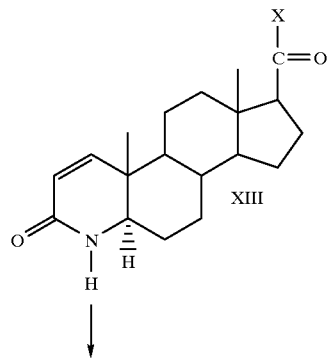 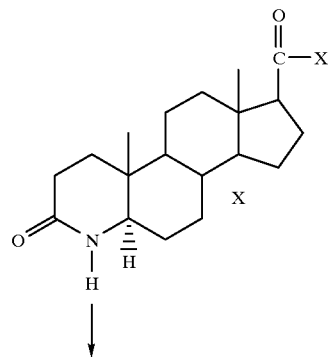

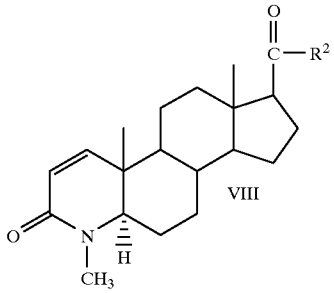 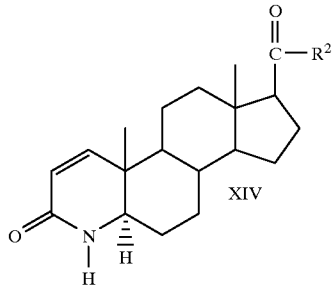 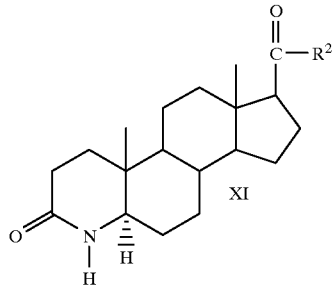

X is 2-pyridylthio or 1-benzotriazoloxy.
R² is 1- or 2-adamantyl or norbornanyl.

Also a preferred 4-azasteroid is a 17β-acyl-4-aza-5α-androst-1-ene-3-one compound of the formula:

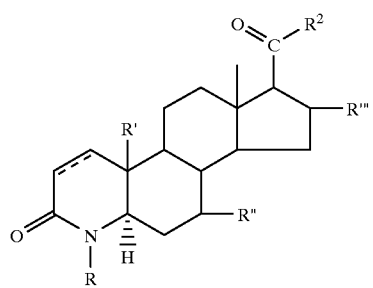

IA wherein the dotted line represents a double bond when present;

R is selected from hydrogen, methyl and ethyl;

R² is (a) a monovalent radical selected from straight or branched chain alkyl, or cycloalkyl, of from 1–12 carbons, which can be substituted by one or more of $C_1-C_2$ alkyl or halo;

(b) an aralkyl radical selected from benzyl or phenethyl;

(c) a polycyclic aromatic radical which can be substituted with one or more of: —OH, protected —OH, —$OC_1-C_4$ alkyl, $C_1-C_4$ alkyl, halo or nitro;

(d) a monocyclic aromatic radical which can be substituted with one or more of:

(1) —OH, —$OC_1-C_4$ alkyl, $C_1-C_4$ alkyl, —$(CH_2)_m$OH, —$(CH_2)_n$, COOH, including protected hydroxy, where m is 1–4, n is 1–3, providing $C_1-C_4$ alkyl is only present when one of the above oxygen-containing radicals is present;

(2) —SH, —$SC_1-C_4$ alkyl, —$SOC_1-C_4$ alkyl, —$SO_2C_1-C_4$ alkyl, —$SO_2N(C_1-C_4\text{-alkyl})_2$, $C_1-C_4$ alkyl —$(CH_2)_m$SH, —S—$(CH_2)_n$—O—$COCH_3$, where m is 1–4 n is 1–3, providing $C_1-C_4$ alkyl is only present when one of the above sulfur containing radicals is present;

(3) $N(R^3)_2$, which can be protected, where $R^3$ is independently H or $C_1-C_4$ alkyl, where the monoaryl ring can also be further substituted with $C_1-C_4$ alkyl; and (4) heterocyclic radical selected from 2- or 4-pyridyl, 2-pyrrolyl, 2-furyl or thiophenyl;

and R', R" and R'" are each selected from hydrogen and methyl, and pharmaceutically acceptable salts thereof.

A preferred embodiment of the compounds of our invention process is:

the compound of above Structure IA,
wherein the dotted line is a double bond,
R is hydrogen or methyl, and
R² is branched chain alkyl, or cycloalkyl of from 4–10 carbons, and R" and R'" are hydrogen.

Another embodiment of the invention is the compounds of above Structure I where R² is phenyl, or phenyl substituted by substituents described above, including where R² is phenyl, 2-, 3-, or 4-tolyl, xylyl, 2-bromophenyl, 2-chlorophenyl, 2,6-dichlorophenyl, 2,6-dibromophenyl, aminophenyl, N-alkylaminophenyl, N-N-dialkylaminophenyl, 4-biphenyl, 3-biphenyl, naphthyl, anthracyl, phenanthryl, thiophenyl, methylthiophenyl, methylsulfinyl, phenyl, methylsulfophenyl, aminosulfophenyl, thioethylphenyl, acetoxymethylthiophenyl, 17β-(4-hydroxyphenyl), 17β-(3-hydroxyphenyl), 17β-(3,4-dihydroxyphenyl), or 17β-(3,5-dimethyl-4-hydroxyphenyl).

Representative compounds of the invention are:

17β-(phenylcarbonyl)-4-aza-4-methyl-5α-androst-1-ene-3-one;

17β-(2-tolylcarbonyl)-4-aza-4-methyl-5α-androst-1-ene-3-one;

17β-(3-tolylcarbonyl)-4-aza-4-methyl-5α-androst-1-ene-3-one;
17β-(4-tolylcarbonyl)-4-aza-4-methyl-5α-androst-1-ene-3-one;
17β-(2-bromophenylcarbonyl)-4-aza-4-methyl-5α-androst-1-ene-3-one;
17β-(2-chlorophenylcarbonyl)-4-aza-4-methyl-5α-androst-1-ene-3-one;
17β-(2,6-dichlorophenylcarbonyl)-4-aza-4-methyl-5α-androst-1-ene-3-one;
17β-(2,6-dibromophenylcarbonyl)-4-aza-4-methyl-5α-androst-1-ene-3-one;
17β-(xylylcarbonyl)-4-aza-4-methyl-5α-androst-1-ene-3-one;
17β-(t-butylcarbonyl)-4-aza-5α-androst-1-ene-3-one;
17β-(isobutylcarbonyl)-4-aza-5α-androst-1-ene-3-one;
17β-(isooctylcarbonyl)-4-aza-5α-androst-1-ene-3-one;
17β-(n-octylcarbonyl)-4-aza-5α-androst-1-ene-3-one;
17β-(1,1-diethylbutylcarbonyl)-4-aza-5α-androst-1-ene-3-one;
17β-(neopentylcarbonyl)-4-aza-5α-androst-1-ene-3-one;
17β-(tert-amylcarbonyl)-4-aza-4-5α-androst-1-ene-3-one;
17β-(tert-hexylcarbonyl)-4-aza-4-5α-androst-1-ene-3-one;
17β-(cyclohexylcarbonyl)-4-aza-5α-androst-1-ene-3-one;
17β-(cyclopentylcarbonyl)-4-aza-5α-androst-1-ene-3-one;
17β-(benzylcarbonyl)-4-aza-5α-androst-1-ene-3-one;
17β-(2-pyridylcarbonyl)-4-aza-5α-androst-1-ene-3-one;
17β-(4-pyridylcarbonyl)-4-aza-5α-androst-1-ene-3-one;
17β-(2-pyrrolylcarbonyl)-4-aza-5α-androst-1-ene-3-one;
17β-(2-furylcarbonyl)-4-aza-5α-androst-1-ene-3-one;
17β-(2-thiophenylcarbonyl)-4-aza-5α-androst-1-ene-3-one;
17β-(2-adamantylcarbonyl)-4-aza-5α-androst-1-ene-3-one;
17β-(3-(phenylcarbonyl)-4-aza-5α-androst-1-ene-3-one;
17β-(2-tolylcarbonyl)-4-aza-5α-androst-1-ene-3-one;
17β-(3-tolylcarbonyl)-4-aza-5α-androst-1-ene-3-one;
17β-(4-tolylcarbonyl)-4-aza-5α-androst-1-ene-3-one;
17β-(2-bromophenylcarbonyl)-4-aza-5α-androst-1-ene-3-one;
17β-(2-chlorophenylcarbonyl)-4-aza-5α-androst-1-ene-3-one;
17β-(2,6-dichlorophenylcarbonyl)-4-aza-5α-androst-1-ene-3-one;
17β-(2,6-dibromophenylcarbonyl)-4-aza-5α-androst-1-ene-3-one;
17β-(xylylcarbonyl)-4-aza-5α-androst-1-ene-3-one;
17β-(phenylethyl)carbonyl-4-aza-5α-androst-1-ene-3-one;
17β-(4-dimethylaminophenylcarbonyl)-4-aza-5α-androst-1-en-3-one;
17β-(3-dimethylaminophenylcarbonyl)-4-aza-5α-androst-1-en-3-one.
17β-(3,4-diethylaminophenylcarbonyl)-4-aza-androst-1-en-3-one.
17β-(3,5-dimethyl-4-diethylaminophenylcarbonyl)-4-aza-5α-androst-1-en-3-one;
17β-(4-N-methylaminomethylphenylcarbonyl)-4-aza-5α-androst-1-en-3-one; or
17β-(2-N-ethylamino-4-ethylphenylcarbonyl)-4-aza-5α-androst-1-en-3-one.
17β-(4-phenylbenzoyl)-4-aza-5α-androst-1-en-3-one;
17β-(3-phenylbenzoyl)-4-aza-5α-androst-1-en-3-one;
17β-(4-biphenyl)-4-aza-5α-androst-1-en-3-one;
17β-(3-biphenyl)-4-aza-5α-androst-1-en-3-one;
17β-(1-naphthyl)-4-aza-5α-androst-1-en-3-one;
17β-(2-naphthyl)-4-aza-5α-androst-1-en-3-one;
17β-(1-phenanthryl)-4-aza-5α-androst-1-en-3-one;
17β-(2-phenanthryl)-4-aza-5α-androst-1-en-3-one;
17β-(1-biphenyl)-4-aza-5α-androst-1-en-3-one;
17β-(9-anthracyl)-4-aza-5α-androst-1-en-3-one;
17β-(4-thiophenylcarbonyl)-4-aza-5α-androst-1-en-3-one;
17β-(3-thiophenylcarbonyl)-4-aza-5α-androst-1-en-3-one;
17β-(4-methylthiophenylcarbonyl )-4-aza-5α-androst-1-en-3-one;
17β-(4-methylsulfinylphenylcarbonyl)-4-aza-5α-androst-1-en-3-one;
17β-(4-methylsulfophenylcarbonyl)-4-aza-5α-androst-1-en-3-one;
17β-(3-methylsulfinylphenylcarbonyl)-4-aza-5α-androst-1-en-3-one;
17β-(4-N,N-dimethylaminosulfophenylcarbonyl)-4-aza-5α-androst-1-en-3-one;
17β-(2-ethyl-4-methylthiophenylcarbonyl)-4-aza-5α-androst-1-en-3-one;
17β-(4-thioethylphenylcarbonyl)-4-aza-4-methyl-5α-androst-1-en-3-one;
17β-(4-acetoxymethylthiophenylcarbonyl)-4-aza-4-methyl5α-androst-1-en-3-one;
17β-(2-methyl-4-methylthiophenylcarbonyl)-4-aza-4-methyl-5α-androst-1-en-3-one;
17β-(2-methyl-4-methylsulfinylphenylcarbonyl)-4-aza-4-methyl-5α-androst-1-en-3-one;
17β-(2-isopropyl-4-methylsulfophenylcarbonyl)-4-aza-4-methyl-5α-androst-1-en-3-one;
17β-(4-methylthiophenylcarbonyl)-4-aza-4-methyl-5α-androstan-3-one;
17β-(4-methylsulfinylphenylcarbonyl)-4-aza-4-methyl-5α-androstan-3-one;
17β-(4-methylsulfophenylcatbonyl)-4-aza-4-methyl-5α-androstan-3-one;
17β-(4-hydroxyphenyl)-4-aza-5α-androst-1-en-3-one;
17β-(3-hydroxyphenyl)-4-aza-5α-androst-1-en-3-one;
17β-(3,4-dihydroxyphenyl)-4-aza-5α-androst-1-en-3-one;
17β-(3,5-dimethyl-4-hydroxyphenyl)-4-aza-5α-androst-1-en-3-one;
17β-(4-hydroxymethylphenyl)-4-aza-5α-androst-1-en-3-one;
17β-(2-hydroxyethylphenylcarbonyl)-4-aza-5α-androst-1-en-3-one;
17β-(4-methoxyphenyl)-4-aza-5α-androst-1-en-3-one;
17β-(4-carboxymethylphenyl)-4-aza-5α-androst-1-en-3-one;
17β-(4-hydroxyphenyl)-4-aza-4-methyl-5α-androst-1-en-3-one;
17β-(3-hydroxyphenyl)-4-aza-4-methyl-5α-androst-1-en-3-one;
17β-(3,4-dihydroxyphenyl)-4-aza-4-methyl-5α-androst-1-en-3-one;
17β-(3,5-dimethyl-4-hydroxyphenyl)-4-aza-4-methyl-5α-androst-1-en-3-one;
17β-(4-hydroxymethylphenyl)-4-aza-4-methyl-5α-androst-1-en-3-one;
17β-(2-hydroxyethylphenylcarbonyl)-4-aza-4-methyl-5α-androst-1-en-3-one;
17β-(4-methoxyphenyl)-4-aza-4-methyl-5α-androst-1-en-3-one;
17β-(4-carboxymethylphenyl)-4-aza-4-methyl-5α-androst-1-en-3-one; and
17β-(4-carboxyphenyl)-4-aza-5α-androst-1-en-3-one, and the corresponding compounds wherein the 4-hydrogen substituent is replaced in each of the above named compounds by a methyl or an ethyl radical.

The compounds of formula IA of the present invention are prepared by a method starting with the known steroid ester of the formula:

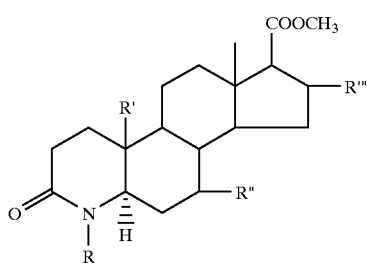

named 17β-(carbomethoxy)-4-aza-5α-androstan-3-one, which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydeogenation step, it is preferable that the 4-aza nitrogen be unsubstituted, The dehydrogenation step can be carried out, e.g. according to the procedure of Dolling, et al. involving dichlorodicyanobenzoquinone, JACS (1988) Vol. 110, pp. 3318–3319. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an R²-Li or an R²MgX (X=Cl, Br) compound, such as sec-butylmagnesium chloride in tetrahydrofuran, to form the desired product, e.g., 17β-(sec-butylcarbonyl)-4-alkyl-4-aza-5α-androst-1-en-3-one (VIII) which is isolated by chromatography on silica gel. When the previous reaction is carried out using an R²MgX or, an R²-Li compound in place of sec-butylmagnesium chloride, the corresponding 17β-(acyl)-4-alkyl-4-aza-5α-androst-1-en-3-one is prepared wherein acyl is R² carbonyl.

In accordance with the process of our invention, the corresponding 17β-acyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove, i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the 1,2-double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3-one, (IX) which, in turn, is converted to the corresponding thiopyridyl ester, 17β-(2-pyridylthiocarbonyl)-4-aza-5α-androstan-1-one (X) followed by treatment of the ester with an R²MgX or R²Li compound wherein R² is as defined hereinabove to form a 17β-(acyl)-4-aza-5α-androstan-3-one (XI) which is dehydrogenated as previously described to produce compound XIV, 17β-(acyl)-4-aza-5α-androst-1-en-3-one.

In an additional alternative process for making the compounds of formula I when the starting material is an ester, particularly methyl ester as shown in formula III–V in the schematic, reaction with a Grignard reagent R²MgX, gives the ketone, 17β-R²CO—, corresponding to the R² moiety associated with the Grignard reagent.

The 16-methyl derivative wherein R'" is methyl are prepared from known 16-methyl-17β-acyl-4-methyl-4-aza-5α-androstan-3-ones, e.g. 4,16β-dimethyl-17β-acetyl-4-aza-5β-androstan-3-one by known dehydrogenation procedures for 4-methyl-4-aza compounds to produce the corresponding 4,16β-dimethyl-17β-acetyl-4-aza-5α-androst-1-en-3-one.

The above reactions are schematically represented in the following structural outline:

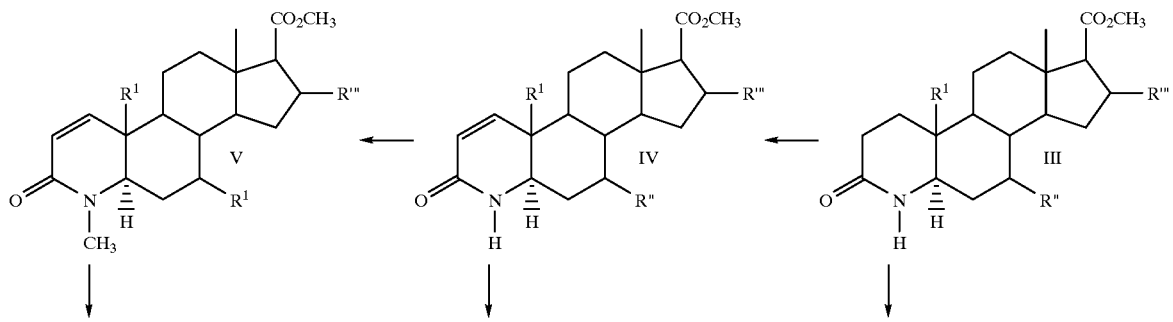

-continued

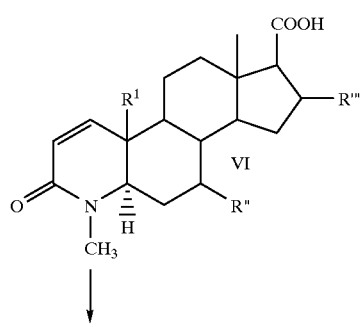

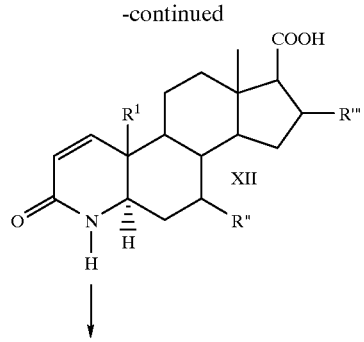

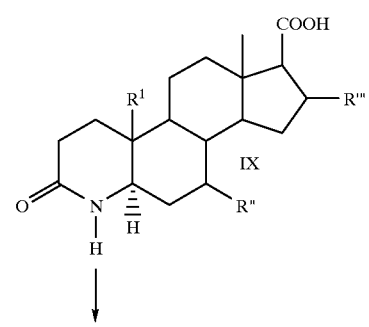

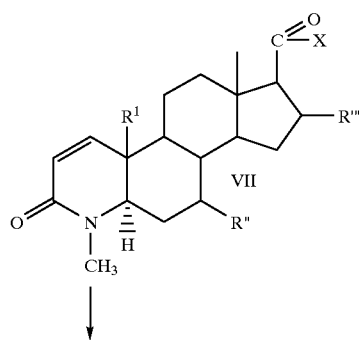

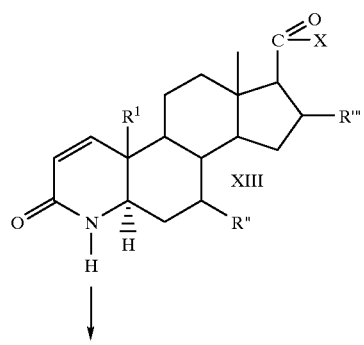

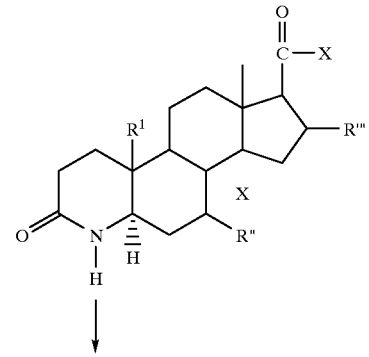

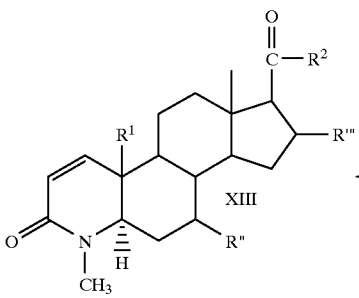

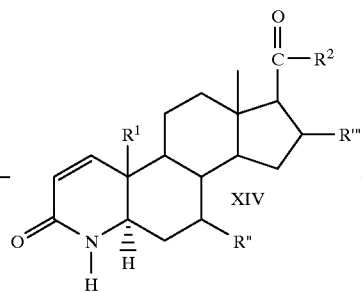

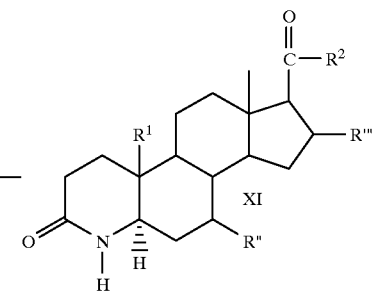

X is 2-pyridylthio wherein X is a 2-pyridylthio substituent and $R^2$ is defined as hereinabove.

In the above described reaction Scheme, where $R^2$ is p-hydroxybiphenyl, this can be derived by starting with an appropriate bromobiphenylylphenol, e.g. p-bromobiphenylphenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

By the term "$C_1$–$C_4$ alkyl" is used herein, is meant linear or branched alkyl, including methyl, ethyl, propyl, isopropyl, n-butyl, isobutyl, sec-butyl and t-butyl.

When this reaction scheme is carried out using an $R^2MgX$ or $R^2$-Li compound containing a thiophenyl substituted $R^2$, e.g. p-methylthiophenyl magnesium chloride, the corresponding 17β-(substituted thio-benzoyl)-4-alkyl aza-5α-androst-1-en-3-one is prepared wherein phenyl is $R^2$.

The Grignard reagent, $R^2MgX$, for all the species included within the scope of this invention, are available or can readily be made by one skilled in the art. For example, where $R^2$ is $C_1$–$C_4$ alkyl thiophenyl, can be formed from the appropriate $C_1$–$C_4$ alkyl thiobromobenzene, e.g. p-methylthiobromobenzene.

The formed $C_1$–$C_4$ alkyl thiobenzene can be used to further prepare $C_1$–$C_4$ alkyl sulfoxides by oxidation with e.g. m-chloroperbenzoic acid. The resulting sulfoxide can be further oxidized by the use of the m-chloroperbenzoic acid reaction to proceed for a longer period of time to form the $C_1$–$C_4$ alkyl sulfone.

Further, the sulfoxide can be used in the Pummerer rearrangement to form the corresponding thiol.

The —$SO_2N(C_1$–$C_4$ alkyl$)_2$ substituted phenyl ($R^2$) is formed from the appropriate bromobenzene, e.g. p-N,N-dimethylaminosulfobromobenzene which is used directly in the Grignard reaction to form the final product.

The thioalkyl groups on the phenyl ring, i.e. —$(CH_2)_m$SH, where m is 1–4, are readily formed via a four step procedure from an alkoxy alkyl phenyl bromide, Br—$C_6H_4$—$(CH_2)_m$ $OCH_3$. Direct addition of the Grignard reagent prepared from above-bromoalkyl phenyl derivative to the thiopyridyl ester results in the keto derivative, i.e. 17β(4-methoxyalkyl-benzoyl)-4-aza-5α-androst-1-ene-3-one. This can be readily converted into thio analogue via BBr₃ at −70° C. to form the hydroxyalkyl derivative, followed by displacement by halogen, e.g. bromo and then converting the halogenated compound through NaSH displacement to give the final mercapto compound. Where in the Reaction Scheme said pyridylthio ester is reacted with an aminophenyl containing $R^2$-Li or an $R^2$MgX (X=Cl, Br) compound, such as p-dimethylaminophenyl magnesium chloride, this is carried out in tetrahydrofuran to form the desired product 17β-(p-dimethylaminophenyl-carbonyl)-4-alkyl-4-aza-5α-androst-1-en-3-one (VIII) which is isolated by chromatography on silica gel.

The Grignard reagent, $R^2$MgX, for all of the aminophenyl species included within the scope of this invention, are available and can be made readily by one skilled in the art.

Where in the process said Grignard reagent contains a phenolic type $R^2$ moiety, then said pyridylthio ester is then reacted with an $R^2$-Li or an $R^2$MgX (X=Cl, Br) Grignard reagent, such as p-methoxyphenyl-magnesium chloride in tetrahydrofuran to form the desired product, e.g. 17β-(p-methoxyphenylcarbonyl)-4-alkyl-4-aza-5α-androst-1-en-3-one (VIII) which is isolated by chromatography on silica gel. When this reaction is carried out using another $R^2$MgX or, an $R^2$-Li compound in place of p-methoxyphenylmagnesium chloride, the corresponding 17β-(substituted benzoyl)-4-alkyl-4-aza-5α-androst-1-en-3-one is prepared wherein phenyl is $R^2$.

The Grignard reagent, $R^2$MgX, for all of the species included within the scope of this invention, are available and can be made readily by one skilled in the art.

For example, where $R^2$ is hydroxyphenyl, this can be derived by starting with an appropriate bromophenol, e.g. p-bromophenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

For $R^2$ being hydroxyethylphenyl, the same blocking procedure can be analogously conducted starting with the appropriate hydroxyalkyl bromophenol, e.g. p-hydroxymethylbromobenzene, or p-hydroxyethylbromobenzene.

Where $R^2$ is carboxyphenyl, this can be obtained by the chromic acid oxidation of the appropriate hydroxymethylbenzene, e.g. p-bromo-hydroxymethylbenzene, formed as described above.

Where $R^2$ is -O-$C_1$-$C_4$ alkyl, the appropriate bromo-O-$C_1$-$C_4$ alkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

Also within the scope of the present invention is the use of ketone reduction products of IA, in combination with flutamide for treatment of prostatic carcinoma, being secondary alcohols of the formula:

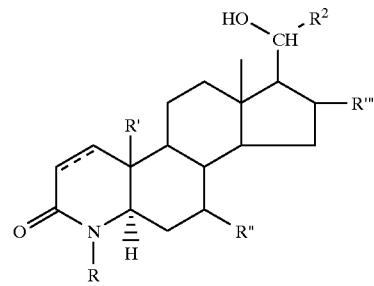

wherein R is selected from hydrogen, methyl and ethyl;
$R^2$ is (a) a monovalent radical selected from straight or branched chain alkyl, or cycloalkyl, of from 1–12 carbons, which can be substituted by one or more of $C_1$-$C_2$ alkyl or halo;
(b) an aralkyl radical selected from benzyl or phenethyl;
(c) a polycyclic aromatic radical which can be substituted with one or more of: —OH, protected —OH, —O$C_1$-$C_4$ alkyl, $C_1$-$C_4$ alkyl, halo or nitro;
(d) a monocyclic aromatic radical which can be substituted with one or more of:
(1) —OH, —O$C_1$-$C_4$ alkyl, $C_1$-$C_4$ alkyl, —(CH₂)$_m$ OH, —(CH₂)$_n$ COOH, including protecting hydroxy, where m is 1–4, n is 1–3, providing $C_1$-$C_4$ alkyl is only present when one of the above oxygen-containing radicals is present;
(2) —SH, —S$C_1$-$C_4$ alkyl, —SO$C_1$-$C_4$ alkyl, —SO₂$C_1$-$C_4$ alkyl, —SO₂N($C_1$-$C_4$-alkyl)₂, $C_1$-$C_4$ alkyl —(CH₂)$_m$SH, —S—(CH₂)$_n$—O—COCH₃, where m is 1–4 n is 1–3, providing $C_1$-$C_4$ alkyl is only present when one of the above sulfur containing radicals is present;
(3) N($R^3$)₂, which can be protected, where $R^3$ is independently H or $C_1$-$C_4$ alkyl, where the monoaryl ring can also be further substituted with $C_1$-$C_4$ alkyl; and
(4) heterocyclic radical selected from 2- or 4-pyridyl, 2-pyrrolyl, 2-furyl or thiophenyl;
R', R" and R'" are hydrogen or methyl, wherein the dotted line represents a double bond which can be present, and pharmaceutically acceptable salts and esters thereof.

These compounds can be made by conventional sodium borohydride reduction of the carbonyl attached to $R^2$ without reducing the amide carbonyl in Ring A or the 1,2-double bond, if present. If the $R^2$ phenyl contains a carbonyl function, it can be selectively blocked and then regenerated after the borohydride reduction by conventional methods.

The borohydride reduction can be carried out in, e.g. water or aqueous methanol, at a temperature of room temperature to 50° C. and the product then isolated and purified by conventional means. The compounds are also active as 5-alpha reductase inhibitors in the treatment of patterned alopecia.

The compounds of the present invention, prepared in accordance with the method described above, are, as already described, potent agents in combination with an antiandrogen, e.g. flutamide for the treatment of prostatic cancer.

17β-substituted steroidal 5α-reductase inhibitors which are non-4-aza steroids are known in the art and include those developed by SmithKline Beckmann as disclosed in U.S. Pat. No. 4,882,319 to Holt, et al.; U.S. Pat. No. 4,910,226 to Holt, et al; EPO Publn. 0 289 327 now U.S. Pat. No. 4,910,226; EPO Publn. 0 277 002 now U.S. Pat. No. 4,888,336; EPO Publn. 0 343 954; EPO Publn. 0 375 344 now U.S. Pat. No. 4,937,237; EPO Publn. 0 375 347; now U.S. Pat. No. 4,970,205; EPO Publn. 0 375 349; now U.S. Pat. No. 5,026,882.

In the method the 17β-substituted non-aza steroids are of the formula:

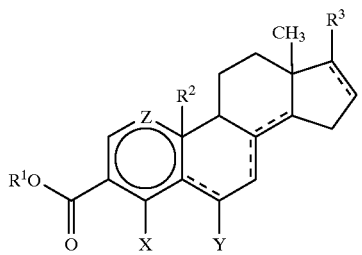

in which:
the A ring has up to 2 double bonds;
the B, C, and D rings have optimal double bonds where indicated by the broken lines, provided that the A, B, and C rings do not have adjacent double bonds and the D ring does not have a $C_{16}$–$C_{17}$ double bond when $R_3$ represents two substituents or a divalent substituent;
Z is $(CH_2)n$ and n is 0 or 2, provided that Z is $(CH)n$ when adjacent to a double bond;
X is H, Cl, F, Br, I, $CF_3$, or $C_{1-6}$alkyl;
Y is H, $CF_3$, F, Cl, or $CH_3$, provided that Y is H when there is no $C_5$–$C_6$ double bond;
$R^1$ is H or $C_{1-8}$alkyl;
$R^2$ is absent or present as H or $CH_3$, provided $R^2$ is absent when the carbon to which it is attached is unsaturated; and
$R^3$ is
(1) α-hydrogen, or α-hydroxyl, or α-acetoxy and/or
(a)

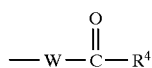

where W is a bond or $C_{1-12}$ alkylidene, and $R^4$ is
(i) hydrogen,
(ii) hydroxyl,
(iii) $C_{1-8}$alkyl,
(iv) hydroxylic $C_{1-8}$alkyl,
(v) $C_{1-8}$alkoxy,
(vi) $NR^5R^6$, where $R^5$ and $R^6$ are each independently selected from hydrogen, $C_{1-8}$alkyl, $C_{3-6}$cycloalkyl, phenyl; or $R^5$ and $R^6$ taken together with the nitrogen to which they are attached represent a 5–6 membered saturated ring,
(vii) $OR^7$, where $R^7$ is hydrogen, alkali metal, $C_{1-8}$alkyl, benzyl, or
(b) —Alk—$OR^8$, where Alk is $C_{1-2}$ alkylidene, and $R^8$ is
(i) phenyl $C_{1-6}$alklycarbonyl,
(ii) $C_{5-10}$ cycloalkylcarbonyl,
(iii) benzoyl,
(iv) $C_{1-8}$ alkoxycarbonyl,
(v) aminocarbonyl, or $C_{1-8}$alkyl substituted aminocarbonyl,
(vi) hydrogen, or
(vii) $C_{1-8}$ alkyl,
(2) =CH—W—CO—$R^4$ or =CH—W—$OR^8$, where W is a bond of $C_{1-12}$ alkylidene and $R^4$ and $R^8$ have the same meaning as above and R8 also is hydrogen or $C_{1-20}$ alkylcarbonyl,
(3)

where the dashed bond replaces the 17-α-hydrogen,
(4) α-hydrogen and $NHCOR^9$ where $R^9$ is $C_{1-12}$alkyl or $NR^5R^6$ where $R^5$ and $R^6$ have the same meaning as above,
(5) α-hydrogen and cyano,
(6) α-hydrogen and tetrazolyl, or
(7) keto;
or a pharmaceutical acceptable salt thereof; except compounds in which:
(i) the B ring has a $C_5$–$C_6$ double bond, $R^1$ is $CH_3$, and $R^3$ is keto, methoxycarbonyl, or acetyl; or
(ii) the A-nor ring has a $C_3$–$C_4$ double bond and $R^3$ is acetoxy or acetyl;
(iii) $R^1$ is $CH_3$ and $R^3$ is acetoxy or acetyl; or
(iv) the A-nor ring has a $C_3$–$C_4$ double bond and $R^1$ is methyl; or
(v) the B ring has a $C_3$–$C_4$ double bond and $R^3$ is β-hydroxy.

Representative compounds whose synthesis and properties are disclosed in the above issued US patents include the following and pharmaceutically acceptable salts thereof:
4-methyl-4-aza-5α-8(14)-pregnen-3-one-(20R)-20-carboxylic acid;
(20R)-hydroxymethyl-4-methyl-4-aza-5α-8(14)-pregnen-3-one;
4-methyl-4-aza-5α-8(14)-androsten-3-one-17β-N,N-diisopropylcarboxamide;
17β-(N,N-diisopropylcarboxamide)-estr-1,3,5(10)-triene-3-phosphonic acid;
17β-(N-tert-butylcarboxamide)-estr-1,3,5(10)-triene-3-phosphonic acid;
17β-(N,N-diisopropylcarboxamide)-estr-1,3,5(10),16-tetraene-3-phosphonic acid;
17β-(N-tert-butylcarboxamide)-estr-1,3,5(10),16-tetraene-3-phosphonic acid;
17β-(N,N-diisopropylcarboxamide)-estr-1,3,5(10),6,8-pentaene-3-phosphonic acid;
17β-(N,N-diisopropylcarboxamide)-2-methyl-estr-1,3,5(10)triene-3-phosphonic acid;
17β-(N,N-diisopropylcarboxamide)-4-methyl-estr-1,3,5(10)-triene-3-phosphonic acid;
17β-(N-N-diisopropylcarboxamide)-estr-1,3,5(10),6-tetraene-3-phosphonic acid;
17β-(N-N-diisopropylcarboxamide)-2-chloro-estr-1,3,5(10)-triene-3-phosphonic acid;
17β-(N-N-diisopropylcarboxamide)-4-chloro-estr-1,3,5(10)-triene-3-phosphonic acid;
17β-(N-butylcarboxamide)-estr-1,3,5(10)-triene-3carboxylic acid;
17β-(N-butylcarboxamide)-estr-1,3,5(10)16-tetraene-3-carboxylic acid;
17β-(N,N-diisopropylcarboxamide)-estr-1,3,5(10)-triene-3-phosphinic acid;

17β-(N-tert-butylcarboxamide)-estr-1,3,5(10)-triene-3-phosphinic acid;
17β-(N,N-diisoprPpylcarboxamide)-2-methyl-estr-1,3,5(10)-triene-3-phosphinic acid;
17β-(N,N-diisopropylcarboxamide)-4-methyl-estr-1,3,5(10)-triene-3-phosphinic acid;
17β-(N,N-diisopropylcarboxamide)-2-chloro-estr-1,3,5(10)-triene-3-phosphinic acid;
17β-(N,N-diisopropylcarboxamide)-4-chloro-estr-1,3,5(10)-triene-3-phosphinic acid;
17β-(N,N-diisopropylcarboxamide)-1,3,5(10),16-tetraene-3-phosphinic acid;
17β-(N-tert-butylcarboxamide)-estr-1,3,5(10),16-tetraene-3-phosphinic acid;
17β-(N,N-diisopropylcarboxamide)-estr-1,3,5(10),6,8-pentaene-3-phosphinic acid;
17β-(N,N-diisopropylcarboxamide)-estr-1,3,5(10),6-tetraene-3-phosphinic acid;
17β-(N,N-diisopropylcarboxamide)-estr-1,3,5(10)-triene-3-phosphonic acid;
17β-(N-tert-butylcarboxamide)-estr-1,3,5(10)-triene-3-phosphonic acid;
17β-(N,N-diisopropylcarboxamide)-estr-1,3,5(10),16-tetraene-3-phosphonic acid;
17β-(N-tert-butylcarboxamide)-estr-1,3,5(10),16-tetraene-3-phosphonic acid;
17β-(N,N-diisopropylcarboxamide)-estr-1,3,5(10),6,8-pentaene-3-phosphonic acid;
17β-(N,N-diisopropylcarboxamide)-2-methyl-estr-1,3,5(10)-triene-3-phosphonic acid;
17β-(N,N-diisopropylcarboxamide)-4-methyl-estr-1,3,5(10)-triene-3-phosphonic acid;
17β-(N,N-diisopropylcarboxamide)-estr-1,3,5(10),6-tetraene-3-phosphonic acid;
17β-(N,N-diisopropylcarboxamide)-2-chloro-estr-1,3,5(10)-triene-3-phosphonic acid;
17β-(N,N-diisopropylcarboxamide)-4-chloro-estr-1,3,5(10)-triene-3-phosphonic acid;
17β-(N,N-diisopropylcarboxamide)-estr-1,3,5(10)-triene-3-sulfonic acid;
17β-(N-tert-butylcarboxamide)-estr-1,3,5(10)-triene-3-sulfonic acid;
17β-(N,N-diisopropylcarboxamide)-estr-1,3,5(10),16-tetraene-3-sulfonic acid;
17β-(N-tert-butylcarboxamide)-estr-1,3,5(10),16-tetraene-3-sulfonic acid;
17β-(N,N-diisopropylcarboxamide)-estr-1,3,5(10),6,8-pentaene-3-sulfonic acid;
17β-(N,N-diisopropylcarboxamide)-2-methyl-estr-1,3,5(10)-triene-3-sulfonic acid;
17β-(N,N-diisopropylcarboxamide)-4-methyl-estr-1,3,5(10)-triene-3-sulfonic acid;
17β-(N,N-diisopropylcarboxamide)-2-chloro-estr-1,3,5(10)-triene-3-sulfonic acid;
17β-(N,N-diisopropylcarboxamide)-4-chloro-estr-1,3,5(10)-triene-3-sulfonic acid;
17β-(N,N-diisopropylcarboxamide)-androst-3,5-diene-3-phosphinic acid;
17β-(N-t-butylcarboxamide)-androst-3,5-diene-3-phosphinic acid;
17β-(N,N-diisopropylcarboxamide)-5α-androst-3-ene-3-phosphinic acid;
17β-(N,N-diisopropylcarboxamide)-5α-androst-2-ene-3-phosphinic acid;
17β-(N,N-diisopropylcarboxamide-androst-2,4-diene-3-phosphinic acid; methyl(17β-N,N-diisopropylcarboxamide)-androst-3,5-diene-3-phosphinic acid;
20α-(hydroxymethyl)-5α-pregn-3-ene-3-phosphinic acid;
17β-(N,N-diisopropylcarboxamide)-4-fluoro-5α-androst-3-ene-3-phosphinic acid;
20α-(hydroxymethyl)-4-fluoro-5α-pregn-3-ene-3-phosphinic acid;
20α-(hydroxymethyl)-A-nor-5α-pregn-1-ene-2-phosphinic acid;
17β-(N,N-diisopropylcarboxamide)-5α-androst-1,3-diene-3-phosphinic acid;
17β-(N,N-diisopropylcarboxamide)-5α-androstane-3β-phosphinic acid;
17β-(N,N-diisopropylcarboxamide)-estr-3,5(10)-diene-3-phosphinic acid;
17β-(N,N-Diisopropylcarboxamide)-estr-3,5-diene-3-phosphinic acid;
17β-(N,N-Diisopropylcarboxamide)-androst-3,5-11-triene-3-phosphinic acid.
20α-(hydroxymethyl)-5α-pregn-3-ene-3-carboxylic acid;
N,N-diisopropyl-5α-androst-3-ene-17β-carboxamide-3 carboxylic acid;
N,N-diisopropyl-androst-3,5-diene 17β-carboxamide-3-carboxylic acid;
17β-(N,N-diisopropylcarboxamide)-4-fluoro-5α-androst-3-ene-3-carboxylic acid;
20α-(hydroxymethyl)-4-fluoro-5α-pregn-3-ene-3-carboxylic acid;
20α-(hydroxymethyl)-A-nor-5α-pregn-1-ene-2-carboxylic acid;
17β-N,N-diisopropylcarboxamide-5α-androst-1,3-diene-3-carboxylic acid;
N-t-Butyl Androst-3,5-diene-17β-carboxamide-3-carboxylic acid;
N,N-Diisopropyl-5α-Androst-2-ene-17β-carboxamide-3-carboxylic acid;
N,N-Diisopropyl Androst-2,4,-diene-17β-carboxamide-3-carboxylic acid;
N,N-Diisopropyl 5α-Androstane-17β-carboxamide carboxylic acid;
N,N-Diisopropyl Estr-3,5(10)-diene-17β-carboxamide-3-carboxylic acid;
N,N,-Diisopropyl Estr-3,5-diene-17β-carboxamide-3-carboxylic acid;
20α(hydroxymethyl)-5α-pregn-3-ene-carboxylic acid
N,N-diisopropyl-5α-androst-3-ene-17β-carboxamide-3-carboxylic acid;
N,N-diisopropyl-androst-3,5-diene-17β-carboxamide-3-carboxylic acid;
17β-(N,N-diisopropylcarboxamide)-4-fluoro-5α-androst-3-ene-3-carboxylic acid;
17β-(N,N-Diisopropylcarboxamide)-androst-3,5,11-triene-3-carboxylic acid;
17β-(N,N-Diisopropylcarboxamide)-androst-3,5-diene-3-thiocarboxylic acid;
17β-(N-t-Butylcarboxamide)-androst-3,5,11-triene-3-carboxylic acid;
17β-(N-t-Butylcarboxamide)-androst-3,5-diene-3-thiocarboxylic acid,
N-t-butyl-androst-3,5-diene-17β-carboxamide-3-carboxylic acid,
N,N-diisopropyl-androst-3,5-diene-17β-carboxamide-3-carboxylic acid,
20α-(hydroxymethyl)-3-α-pregn-3-ene-3-carboxylic acid,
20α-(hydroxymethyl)-4-fluoro-5-α-pregn-3-ene-3-carboxylic acid,
3-carbomethoxy-N,N-diisopropyl-androst-3,5-diene-17β-carboxamide,
17β-N,N-diisopropylcarboxamide-5-α-androst-1,3-diene-3-carboxylic acid, N,N-Diisopropyl 5-α-androst-2-ene-17β-carboxamide-3-carboxylic acid, N,N-diisopropyl androst-2-4-diene-17β-carboxamide-3-carboxylic acid, N,N-diisopropyl 5-α-androstane-17β-carboxamide-3β-carboxylic acid, and N,N-diisopropyl estr-3,5(10)-diene-17β-carboxamide-3-carboxylic acid.

The benzoylaminophenoxy butanoic acid derivatives are of the formula:

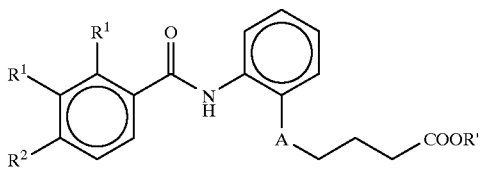

wherein R' is hydrogen or alkyl of from 1 to 4 carbon atom(s); A is oxygen atom, sulfur atom or sulfinyl (SO) group; both $R^1$'s are methyl or chlorine, or the two $R^1$'s and the carbon atoms of the benzene ring to which the two $R^1$'s are linked together are cyclopentane, cyclohexane or a benzene ring; and $R^2$ represents a group of formula:

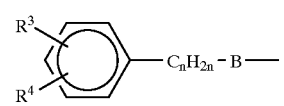 (i)

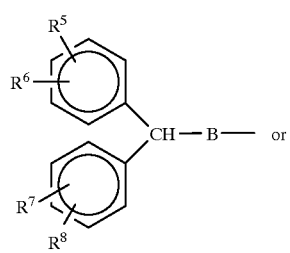 (ii)

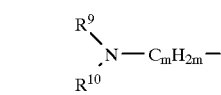 (iii)

wherein B is oxygen, sulfur or a group of formula: $NR^{11}$ wherein $R^{11}$ is hydrogen or alkyl of from 1 to 4 carbon atom(s), $R^3$, $R^4$, $R^5$, $R^6$, $R^7$, and $R^8$ are, independently, hydrogen, alkyl of from 1 to 4 carbon atom(s), halogen, trifluoromethyl or cyclobutylmethyl, m is 0 or 1, n is an integer of from 1 to 5, and $R^9$ is a hydrogen, alkyl of from 1 to 5 carbon atom(s) or a group of formula:

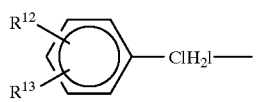

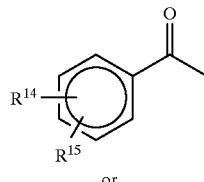

or

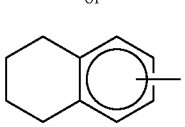

wherein $R^{12}$, $R^{13}$, $R^{14}$, and $R^{15}$ are, independently, hydrogen, alkyl of from 1 to 4 carbon atom(s), halogen, trifluoromethyl or cyclobutylmethyl, and 1 is an integer of from 1 to 4, and $R^{10}$ is a group of formula:

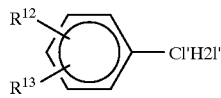

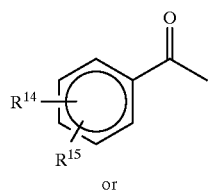

or

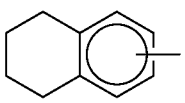

wherein $R^{12}$, $R^{13}$, $R^{14}$, and $R^{15}$ are, independently, hydrogen, alkyl of from 1 to 4 carbon atom(s), halogen, trifluoromethyl or cyclobutylmethyl, and 1' is an integer of from 1 to 4; or non-toxic salts thereof.

Representative examples of each of these two classes of compounds whose synthesis and properties are disclosed in the above cited US issued patents include the following:

4-[2-(4-benzyloxy-2,3-dimethylbenzoylamino)phenoxy] butanoic acid;

4-[2-[4-(2-methylbenzyloxy)-2,3-dimethylbenzoylamino] butanoic acid;

4-[2-[4-(3-methylbenzyloxy)-2,3-dimethylbenzoylamino] phenoxy]butanoic acid;

4-[2-[(4-methylbenzyloxy)-2,3-dimethylbenzoylamino] phenoxy]butanoic acid;

4-[2-[4-(2,6-dimethylbenzyloxy)-2,3-dimethylbenzoylamino]phenoxy]butanoic acid;

4-[2-[4-(4-ethylbenzyloxy)-2,3-dimethylbenzoylamino] phenoxy]butanoic acid;

4-[2-[4-(4-propylbenzyloxy)-2,3-dimethylbenzoylamino] phenoxy]butanoic acid;

4-[2-[4-(4-isopropylbenzyloxy)-2,3-dimethylbenzoyl-amino]phenoxy]butanoic acid;

4-[2-[4-(4-isobutylbenzyloxy)-2,3-dimethylbenzoyl-amino]phenoxy]butanoic acid;

4-[2-[4-(4-chlorobenzyloxy)-2,3-dimethylbenzoylamino] phenoxy]butanoic acid;

4-[2-[4-(4-cyclobutylmethylbenzyloxy)-2,3-dimethylbenzoylamino]phenoxy]butanoic acid;

4-[2-[4-(2-phenylethoxy)-2,3-dimethylbenzoylamino]phenoxy]butanoic acid;
4-[2-[4-(3-phenylpropoxy)-2,3-dimethylbenzoylamino]phenoxy]butanoic acid;
4-[2-[4-(4-phenylbutoxy)-2,3-dimethylbenzoylamino]phenoxybutanoic acid;
4-[2-[4-(5-phenylpentyloxy)-2,3-dimethylbenzoylamino]phenoxy]butanoic acid;
4-[2-[4-(1-(4-isobutylphenyl)ethoxy)-2,3-dimethylbenzoylamino]phenoxy]butanoic acid;
4-[2-[4-(4-propylbenzyloxy)-2,3-dimethylbenzoylamino)phenylthio]butanoic acid;
4-[2-[1-(4-isobutylphenyl)ethoxy)-2,3-dimethylbenzoylamino]phenylthio]butanoic acid;
4-[2-[4-(4-propylbenzyloxy)-2,3-dimethylbenzoylamino]phenylsulfinyl)butanoic acid;
4-[2-[4-[N-(4-trifluoromethylphenylmethyl)amino)-2,3-dimethylbenzoylamino]phenoxy]butanoic acid;
4-[2-[4-(4-isobutylbenzyloxy)-5,6,7,8-tetrahydronaphthalene-1-carbonylamino)phenoxybutanoic acid;
4-[2-[4-(4-isobutylbenzyloxy)naphthalene-1-carbonylamino)phenoxy)butanoic acid;
4-[2-[8-(4-isobutylbenzyloxy)-5,6,7,8-tetrahydronaphthalene-1-carbonylamino)phenylthio]butanoic acid;
4-[2-[4-[bis(4-propylphenyl)methoxy]2,3-dimethylbenzoylamino)phenoxy]butanoic acid;
4-[2-(4-diphenylmethoxy)-2,3-dimethylbenzoylamino)phenoxy]butanoic acid;
4-[2-[4-[bis(4-propylphenyl)methylamino]-2,3-dimethylbenzoylamino]phenoxy]butanoic acid;
4-[2-[4-[bis-(4-propylphenyl)methylthio]-2,3-dimethylbenzoylamino]phenoxy]butanoic acid;
4-[2-[4-[N,N-bis(4-propylphenylmethyl)amino]-2,3-dimethylbenzoylamino]phenoxy]butanoic acid;
4-[2-[4-[N,N-bis(4-trifluoromethylphenylmethyl)amino]-2,3-dimethylbenzoylamino]phenoxy]butanoic acid;
4-[2-[4-N-methyl-N-(5,6,7,8-tetrahydronaphth-1-yl]aminomethyl]-2,3-dimethylbenzoylamino]phenoxy]butanoic acid;
8-(p-pentylbenzoyl)amino-2-(5-tetrazolyl)-1,4-benzodioxane;
8-(p-pentylbenzoyl)amino-2-(5-tetrazolyl)-6 chloro-1,4-benzodioxane;
8-(m-octylbenzoyl)amino-2-(5-tetrazolyl)-1,4-benzodioxane;
8-(o-pentylbenzoyl)amino-2-(5-tetrazolyl)-1,4-benzodioxane;
8-(p-butylbenzoyl)amino-2-(5-tetrazolyl)-1,4-benzodioxane;
8-(p-hexylbenzoyl)amino-2-(5-tetrazolyl)-1,4-benzodioxane;
8-(p-heptylbenzoyl)amino-2-(5-tetrazolyl)-1,4-benzodioxane;
8-(p-octylbenzoyl)amino-2-(5-tetrazolyl)-1,4-benzodioxane;
8-(p-nonylbenzoyl)amino-2-(5-tetrazolyl)-1,4-benzodioxane;
8-(p-decylbenzoyl)amino-2-(5-tetrazolyl)-1,4-benzodioxane;
8-(p-undecylbenzoyl)amino-2-(5-tetrazolyl)-1,4-benzodioxane;
8-(p-dodecylbenzoyl)amino-2-(5-tetrazolyl)-1,4-benzodioxane;
8-(p-pentyloxybenzoyl)amino-2-(5-tetrazolyl)-1,4-benzodioxane;
8-(m-pentyloxybenzoyl)amino-2-(5-tetrazolyl)-1,4-benzodioxane;
8-(o-pentyloxybenzoyl)amino-2-(5-tetrazolyl)-1,4-benzodioxane;
8-(p-butyloxybenzoyl)amino-2-(5-tetrazolyl)-1,4-benzodioxane;
8-(p-nonyloxybenzoyl)amino-2-(5-tetrazolyl)-1,4-benzodioxane;
8-(p-propoxybenzoyl)amino-2-(5-tetrazolyl)-1,4-benzodioxane;
8-(p-hexyloxybenzoyl)amino-2-(5-tetrazolyl)-1,4-benzodioxane;
8-(p-heptyloxybenzoyl)amino-2-(5-tetrazolyl)-1,4-benzodioxane;
8-(p-octyloxybenzoyl)amino-2-(5-tetrazolyl)-1,4-benzodioxane;
8-(o-decyloxybenzoyl)amino-2-(5-tetrazolyl)-1,4-benzodioxane;
8-(p-isopentyloxybenzoyl)amino-2-(5-tetrazolyl)-1,4-benzodioxane;
8-(p-isohexyloxybenzoyl)amino-2-(5-tetrazolyl)-1,4-benzodioxane;
8-[p-(1-methylbutoxy)benzoyl]amino-2-(5-tetrazolyl)-1,4-benzodioxane;
8-(N-methyl-N-(p-octynyloxy)benzoyl])amino-2-(5-tetrazolyl)-1,4-benzodioxane;
8-(p-oxtyloxybenzoyl)amino-1,4-benzodioxane-2-carboxylic acid and methyl ester thereof;
8-(p-isoheptyloxybenzoyl)amino-2-(5-tetrazolyl)-1,4-benzodioxane;
8-(p-isooctyloxybenzoyl)amino-2-(5-tetrazolyl)-1,4-benzodioxane;
8-[p-(3,7-dimethyloctyloxy)benzoyl]amino-2-(5-tetrazolyl)-1,4-benzodioxane;
8-(p-octyloxybenzoyl)amino-2-(5-tetrazolyl)-1,4-benzodioxane;
8-(p-heptyloxybenzoyl)amino-2-(5-tetrazolyl)-1,4-benzodioxane-7-carboxylic acid and methyl ester thereof, and the like.

Also included as a 5α-reductase inhibitor in this invention is a cinnamoylamide of the following formula:

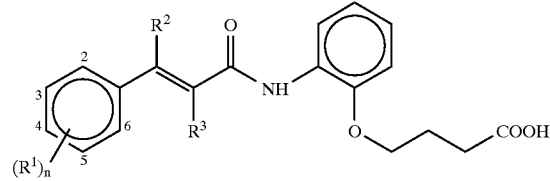

wherein $R^2$ and $R^3$ each independently represents a hydrogen or methyl group with the proviso that
(i) when $R^2$ represents a methyl group, $R^3$ represents hydrogen and $(R^1)n$ represents a member selected from the group consisting of 3-group, 4-pentyl group, 4-neopentyl group, 4-(2-ethylbutyl) group and 4-(2-methylpentyl) group, or
(ii) when $R^2$ represents hydrogen, $R^3$ represents a methyl group and $(R^1)n$ represents a 3-pentyl group, or non-toxic salts thereof.

Representative compounds include:
4-[2-(4-butylthio-β-methylcinnamoylamino)phenoxy]butanoic acid
4-[2-(4-cyclobutylmethy)β-methylcinnamoylamino)phenoxy]butanoic acid
4-[2-(4-cyclohexylmethyl)β-methylcinnamoylamino)phenoxy]butanoic acid 4-[2-(4-{4-phenylbutyl)-β-methylcinnamoylamino)
  phenoxy]butanoic acid
4-[2-(4-phenoxy-β-methylcinnamoylamino)phenoxy]
  butanoic acid
4-[2-(3-pentyl-α-methylcinnamoylamino)phenoxy]
  butanoic acid
4-[2-(4-phenethyl-α-methylcinnamoylamino)phenoxy]
  butanoic acid
4-[2-(3-pentyl-β-methylcinnamoylamino)phenoxy]butanoic
  acid
4-[2-(4-neopentyl]-β-methylcinnamoylamino)phenoxy]
  butanoic acid
4-[2-{4-(2-ethylbutyl)-β-methylcinnamoylamino)phenoxy]
  butanoic acid,
4-[2-{4-(2-methylpentyl)-β-methylcinnamoylamino)
  phenoxy]butanoic acid, and
4-[2-(2-fluoro-4-pentylexy-β-methylcinnamoylamino)
  phenoxy]butanoic acid.

Also included in this invention are fused benz(thio) amides of the formula:

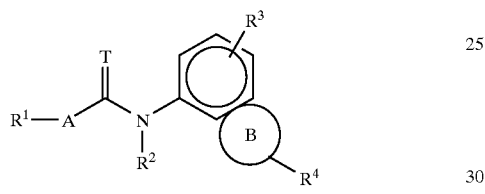

wherein A represents a single bond or a group of methylene, ethylene, trimethylene, tetramethylene, vinylene, propenylene, butenylene, butadienylene or ethynylene group optionally being substituted by one, two or three of straight or branched alkyl group(s) of from 1 to 10 carbon atom(s) and/or phenyl group(s);

B represents a heterocyclic ring of from 4 to 8 members containing one, two or three hetero atom(s) selected from the group consisting of oxygen, nitrogen and sulphur atom(s), wherein the said ring may optionally be substituted by group(s) selected from oxo, thioxo and/or hydroxy group(s) including a ring of formula:

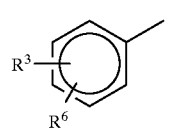 or 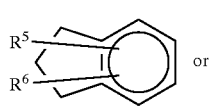

T represents an oxygen atom or a sulphur atom;
$R^1$ represents a group of general formula:

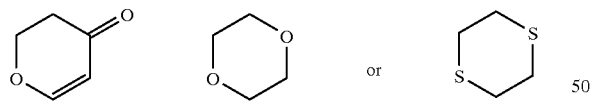

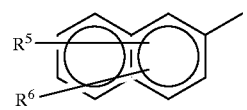

(iv) a straight or branched alkyl, alkenyl or alkynyl group of from 1 to 20 carbon atom(s), wherein $R^5$ and $R^6$ independently represent a hydrogen atom or a halogen atom or a straight or branched alkyl, alkenyl or alkynyl group of from 1 to 20 carbon atom(s) being unreplaced or replaced by one, two, three, four or five optional carbon atom(s), by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s);

$R^2$ represents a hydrogen atom or a straight or branched alkyl group of from 1 to 6 carbon atom(s);

$R^3$ represents a hydrogen atom, a halogen atom, a hydroxy group, a nitro group, a group of general formula: —COOR$^7$, wherein $R^7$ represents a hydrogen atom or a straight or branched alkyl group of from 1 to 6 carbon atom(s), or a straight or branched alkyl, alkoxy or alkylthio group of from 1 to 6 carbon atom(s);

$R^4$ represents a group of general formula:

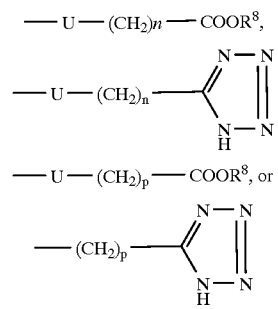

wherein U represents an oxygen atom or a sulphur atom, $R^8$ represents a hydrogen atom or a straight or branched alkyl group of from 1 to 6 carbon atom(s), n and m represent an integer of from 1 to 10, respectively, p and q represent zero or an integer of from 1 to 10, respectively, or non-toxic salts thereof.

Representative compounds include:
7-(p-hexyloxybenzoyl)amino-2-(5-tetrazolyl)benzofuran,
7-(p-octyloxybenzoyl)amino-2-(5-tetrazolyl)benzofuran,
7-(p-heptyloxybenzoyl)amino-2-(5-tetrazolyl)benzofuran,
7-(p-nonyloxybenzoyl)amino-2-)5-tetrazolyl)benzofuran,
7-[p-(4-phenylbutoxy)benzoyl]amino-2-(5-tetrazolyl)-
  benzofuran,
7-[p-(2E,7,-octadienyl)benzoyl]amino-2-(5-tetrazolyl)-
  benzofuran,
7-[p-(6-chlorohexyloxy)benzoyl]amino-2-(5-tetrazolyl)-
  benzofuran and
7-(p-pentyicinnamoyl)amino-2-(5-tetrazolyl)benzofuran,
7-(p-hexyloxybenzoyl)amino-2-(5-tetrazolyl)-2,3-dihydro-
  1-benzofuran,
7-(p-heptyloxybenzoyl)amino-2-(5-tetrazolyl)-2,3-dihydro-
  1-benzofuran, 7-(p-octyloxybenzoyl)amino-2-(5-tetrazolyl)-2,3-dihydro-1-benzofuran,
7-(p-nonyloxybenzoyl)amino-2-(5-tetrazolyl)-2,3-dihydro-1-benzofuran,
7-(p-pentylcinnamoyl)amino-2-(5-tetrazolyl)-2,3-dihydro-1-benzofuran,
8[p-2E,7-octadienyloxy)benzoyl]amino-2-(5-tetrazolyl)quinoline,
8-[p-(4-phenylbutoxy)benzoyl]amino-2-(5-tetrazolyl)quinoline,
8-[p-(6-chlorohexyloxy)benzoyl]amino-2-(5-tetrazolyl)quinoline,
8-[p-(2E,7-octadienyloxy)benzoyl]amino-4-hydroxyquinoline-2-carboxylic acid,
8-[p-(4-phenylbutoxy)benzoyl]amino-4-hydroxyquinoline-2-carboxylic acid,
8-[p-[4-(2-thienyl)butoxy)benzoyl]amino-4-hydroxyquinoline-2-carboxylic acid,
8-[p-(2E,7-octadienyloxy)benzoyl]amino-4-hydroxy-2-(tetrazolyl)quinoline,
8-[p-(4-(2-phenylbutoxy)benzoyl]amino-4-hydroxy-2-(5-tetrazolyl)quinoline and,
8-(p-pentylcinnamoyl)amino-4-hydroxy-2-(5-tetrazolyl)quinoline and,
4-(p-heptyloxybenzoyl)amino-2-(5-tetrazolyl)-1,3-benzodioxole,
4-(p-hexyloxybenzoyl)amino-2-(5-tetrazolyl)-1,3-benzodioxole,
4-[p-[4-(phenylbutoxy)benzoyl]amino-2-(5-tetrazolyl)1,3-benzodioxole,
4-(p-pentylcinnamoyl)amino-2-(5-tetrazolyl)-1,3-benzodioxole,
9-[p-(4-phenylbutoxy)benzoyl]amino-2-(5-tetrazolyl)-3,4-dihydro-2H-1,5-benzodioxepin,
9-[p-(2E, 7-octadienyloxy)benzoyl]amino-2-(5-tetrazolyl)-3,4-dihydro-2H-1,5-benzodioxepin,
9-[p-(7-octenyloxy)benzoyl]amino-2-(5-tetrazolyl)-3,4-dihydro-2H-1,5-benzodioxepin,
8-(p-heptyloxybenzoyl)amino-2-(5-tetrazolyl)-2,3-dihydro-1,4-benzoxazine,
8-[p-(4-phenylbutoxy)benzoyl]amino-2-(5-tetrazolyl)-2,3-dihydro-1,4-benzoxazine and
8-(p-pentylcinnamoyl)amino-2-(5-tetrazolyl)-2,3-dihydro-1,4-benzoxazine,
8-[p-(4-phenylbutoxy)benzoyl]amino-2-(5-tetrazolyl)-4-oxo-4H-1-benzothiopyran,
8-[p-(4-phenylbutoxy)benzol]amino-2-(5-tetrazolyl)-3,4-dihydro-2H-1-benzopyran,
8-[p-(7-octenyloxy)benzoyl]amino-2-(5-tetrazolyl)-3,4-dihydro-2H-1-benzopyran,
8-(p-pentylbenzoyl)amino-2-(5-tetrazolyl)-4-oxo-4H-1-benzopyran,
8-(p-pentylbenzoyl)amino-4-oxo-4H-1-benzopyran-2-carboxylic acid and ethyl ester thereof,
8-(p-hexylbenzoyl)amino-2-(5-tetrazolyl)-4-oxo-4H-1-benzopyran,
8-(p-heptylbenzoyl)amino-2-(5-tetrazolyl)-4-oxo-4H-1-benzopyran,
8-(p-octylbenzoyl)amino-2-(5-tetrazolyl)-4-oxo-4H-1-benzopyran and
8-(p-nonylbenzoyl)amino-2-(5-tetrazolyl-4-oxo-4H-1-benzopyran
8-(p-butoxybenzoyl)amino-2-(5-tetrazolyl)-4-oxo-4H-1-benzopyran,
8-(p-pentyloxybenzoyl)amino-2-(5-tetrazolyl)-4-oxo-4H-1-benzopyran,
8-(p-hexyloxybenzoyl)amino-2-(5-tetrazolyl)-4-oxo-4H-1-benzopyran,
8-(p-heptyloxybenzoyl)amino-2-(5-tetrazolyl)-4-oxo-4H-1-benzopyran,
8-(p-nonyloxybenzoyl)amino-2-(5tetrazolyl)-4-oxo-4H-1-benzopyran,
8-(p-octyloxybenzoyl )amino-2-(5-tetrazolyl)-4-oxo-4H-1-benzopyran,
8-(p-heptyloxybenzoyl)amino-2-(5-tetrazolyl)-6-fluoro-4-oxo-4H-1-benzopyran,
8-(p-octyloxybenzoyl)amino-2-(5-tetrazolyl)-6-methyl-4-oxo-4H-1-benzopyran and
8-(p-heptyloxybenzoyl)amino-2-(5-tetrazolyl)-6-methyl-4-oxo-4H-1-benzopyran and
8p-(2E,7-octadienyloxy)benzoyl]amino-2-(5-tetrazolyl)-4-oxo-4H-1-benzopyran,
8-(p-geranyloxybenzoyl)amino-2-(5-tetrazolyl)-4-oxo-4H-1-benzopyran,
8p-(2E-nonenyloxy)benzoyl]amino-2-(5-tetrazolyl)-4-oxo-4H-1-benzopyran,
8[p-(2E-octenyloxy)benzoyl]amino-2-(5-tetrazolyl)-4-oxo-4H-1-benzopyran,
8[p-(7-octenyloxy)benzoyl]amino-2-(5-tetrazolyl)-4-oxo-4H-1-benzopyran,
8[p-(2E-heptenyloxy)benzoyl]amino-2-(5-tetrazolyl)-4-oxo-4H-1-benzopyran,
8[p-(2E-hexenyloxy)benzoyl]amino-2-(5-tetrazolyl)-4-oxo-4H-1-benzopyran,
8[p-(2E,7-octadienyloxy)benzoyl]amino-2-(5-tetrazolyl)-6-fluoro-4-oxo-4H-1-benzopyran,
8[p-(2E-octenyloxy)benzoyl]amino-2-(5-tetrazolyl)-6-methyl-4-oxo-4H-1-benzopyran,
8[p-(2E,7-octadienyloxy)benzoyl]amino-2-(5-tetrazolyl)-6-chloro-4-oxo-4H-1-benzopyran,
8[p-(2-octynyloxy)benzoyl]amino-2-(5-tetrazolyl)-4-oxo-4H-1-benzopyran, thereof
8[p-(4-chlorobutoxy)benzoyl]amino-2-(5-tetrazolyl)-4-oxo-4H-1-benzopyran,
8[p-(5-chloropentyloxy)benzoyl]amino-2-(5-tetrazolyl)-4-oxo-4H-1-benzopyran,
8[p-(6-chlorohexyloxy)benzoyl]amino-2-(5-tetrazolyl)-4-oxo-4H-1-benzopyran,
8[p-(6-chlorohexyloxy)benzoyl]amino-2-(5-tetrazolyl)-4-oxo-4H-1-benzopyran,
8[p-(7-chloroheptyloxy)benzoyl]amino-2-(5-tetrazolyl)-4-oxo-4H-1-benzopyran,
8[p-(8-chlorooctyloxy)benzoyl]amino-2-(5-tetrazolyl)-6-methyl-4-oxo-4H-1-benzopyran,
8[p-(7-chloroheptyloxy)benzoyl]amino-2-(5-tetrazolyl)-6-methyl-4-oxo-4H-1-benzopyran and
8[p-(8-chlorooctyloxy)benzoyl]amino-2-(5-tetrazolyl)-4-oxo-4H-1-benzopyran,
8[p-(3-phenylpropoxy)benzoyl]amino-2-(5-tetrazolyl)-4-oxo-4H-1-benzopyran,
8[p-(3-phenyl-2E-propenyloxy)benzoyl]amino-2-(5-tetrazolyl)-4-oxo-4H-1-benzopyran,
8[p-(4-phenylbutoxy)benzoyl]amino-2-(5-tetrazolyl)-4-oxo-4H-1-benzopyran,
8[p-(4-phenylbutoxy)benzoyl]amino-2-(5-tetrazolyl)-6-methyl-4-oxo-4H-1-benzopyran,
8[p-[2-(2-naphthy)ethoxy]benzoyl]amino-2-(5-tetrazolyl)-4-oxo-4H-1-benzopyran,
8[p-[2-(2-naphthyl)ethoxy])benzoyl]amino-2-(5-tetrazolyl)-6-methyl-4-oxo-4H-1-benzopyran,
8[p-[3-(3,4-dichlorophenyl)propoxy]benzoyl]amino-2-(5-tetrazolyl)-4-oxo-4H-1-benzopyran,
8[p-[3-(3,4-dichlorophenyl)propoxy]benzoyl]amino-2-(5-tetrazolyl)-4-oxo-4H-1-benzopyran,
8[p-[3-(p-chlorophenyl)butoxy]benzoyl]amino-2-(5-tetrazolyl)-4-oxo-4H-1-benzopyran, 8[p-[3-(p-chlorophenyl)butoxy]benzoyl]amino-6-methyl-2-(5-tetrazolyl)-4-oxo-4H-1-benzopyran,
8[p-[3-(p-chlorophenyl)propoxy]benzoyl]amino-6-methyl-2-(5-tetrazolyl)-4-oxo-4H-1-benzopyran,
8[p-[4-(2-thienyl)butoxy]benzoyl]amino-2-(5-tetrazolyl)-4-oxo-4H-1-benzopyran,
8[p-[4-(2-thienyl)butoxy]benzoyl]amino-2-(5-tetrazolyl)-6-methyl-4-oxo-4H-1-benzopyran,
8-(p-pentylcinnamoyl)amino-4-oxo-4H-1-benzopyran-2-carboxylic acid and methyl ester thereof,
8-(p-pentylcinnamoyl)amino-2-(5-tetrazolyl)-4-oxo-4H-1-benzopyran,
8-(p-pentylcinnamoyl)amino-2-(5-tetrazolyl)-6-methyl-4-oxo-4H-1-benzopyran,
8-(p-pentylcinnamoyl)amino-2-(5-tetrazolyl)-6-fluoro-4-oxo-4H-1-benzopyran,
8-(p-pentylcinnamoyl)amino-6-methyl-4-oxo-4H-1-benzopyran-2-carboxylic acid and ethyl ester thereof,
8-(p-butylcinnamoyl)amino-2-(5-tetrazolyl)-4-oxo-4H-1-benzopyran,
8-(p-hexylcinnamoyl)amino-2-(5-tetrazolyl)-4-oxo-4H-1-benzopyran,
8-(p-heptylcinnamoyl)amino-2-(5-tetrazolyl)-4-oxo-4H-1-benzopyran,
8-cinnamoylamino-2-(5-tetrazolyl)-4-oxo-4H-1-benzopyran,
8-(p-hexyloxycinnamoyl)amino-2-(5-tetrazolyl)-4-oxo-4H-1-benzopyran,
8-(p-heptyloxycinnamoyl)amino-2-(5-tetrazolyl)-4-oxo-4H-1-benzopyran,
8-(p-isohexyloxycinnamoyl)amino-2-(5-tetrazolyl)-4-oxo-4H-1-benzopyran,
8[p-(2-octynyloxy)cinnamoyl]amino-4-oxo-4H-1-benzopyran-2-carboxylic acid,
8[p-(5-chloropentyloxy)cinnamoyl]amino-2-(5-tetrazolyl)-4-oxo-4H-1-benzopyran,
8[p-(6-chlorohexyloxy)cinnamoyl]amino-2-(5-tetrazolyl)-4-oxo-4H-1-benzopyran,
8-(p-pentylbenzoyl)amino-2-(5-tetrazolyl)-1,4-benzodioxane;
8-(p-pentylbenzoyl)amino-2-(5-tetrazolyl)-6 chloro-1,4-benzodioxane;
8-(m-octylbenzoyl)amino-2-(5-tetrazolyl)-1,4-benzodioxane;
8-(o-pentylbenzoyl)amino-2-(5-tetrazolyl)-1,4-benzodioxane;
8-(p-butylbenzoyl)amino-2-(5-tetrazolyl)-1,4-benzodioxane;
8-(p-hexylbenzoyl)amino-2-(5-tetrazolyl)-1,4-benzodioxane;
8-(p-heptylbenzoyl)amino-2-(5-tetrazolyl)-1,4-benzodioxane;
8-(p-octylbenzoyl)amino-2-(5-tetrazolyl)-1,4-benzodioxane;
8-(p-nonylbenzoyl)amino-2-(5-tetrazolyl)-1,4-benzodioxane;
8-(p-decylbenzoyl)amino-2-(5-tetrazolyl)-1,4-benzodioxane;
8-(p-undecylbenzoyl)amino-2-(5-tetrazolyl)-1,4-benzodioxane;
8-(p-dodecylbenzoyl)amino-2-(5-tetrazolyl)-1,4-benzodioxane;
8-(p-pentyloxybenzoyl)amino-2-(5-tetrazolyl)-1,4-benzodioxane;
8-(m-pentyloxybenzoyl)amino-2-(5-tetrazolyl)-1,4-benzodioxane;
8-(o-pentyloxybenzoyl)amino-2-(5-tetrazolyl)-1,4-benzodioxane;
8-(p-butyloxybenzoyl)amino-2-(5-tetrazolyl)-1,4-benzodioxane;
8-(p-nonyloxybenzoyl)amino-2-(5-tetrazolyl)-1,4-benzodioxane;
8-(p-propoxybenzoyl)amino-2-(5-tetrazolyl)-1,4-benzodioxane;
8-(p-hexyloxybenzoyl)amino-2-(5-tetrazolyl)-1,4-benzodioxane;
8-(p-heptyloxybenzoyl)amino-2-(5-tetrazolyl)-1,4-benzodioxane;
8-(p-octyloxybenzoyl)amino-2-(5-tetrazolyl)-1,4-benzodioxane;
8-(o-decyloxybenzoyl)amino-2-(5-tetrazolyl)-1,4-benzodioxane;
8-(p-isopentyloxybenzoyl)amino-2-(5-tetrazolyl)-1,4-benzodioxane;
8-(p-isohexyloxybenzoyl)amino-2-(5-tetrazolyl)-1,4-benzodioxane;
8-[p-(1-methylbutoxy)benzoyl]amino-2-(5-tetrazolyl)-1,4-benzodioxane;
8-(N-methyl-N-(p-octynyloxy)benzoyl])amino-2-(5-tetrazolyl)-1,4-benzodioxane;
8-(p-octyloxybenzoyl)amino-1,4-benzodioxane-2-carboxylic acid and methyl ester thereof;
8-(p-isoheptyloxybenzoyl)amino-2-(5-tetrazolyl)-1,4-benzodioxane;
8-(p-isooctyloxybenzoyl)amino-2-(5-tetrazolyl)-1,4-benzodioxane;
8-[p-(3,7-dimethyloctyloxy)benzoyl]amino-2-(5-tetrazolyl)-1,4-benzodioxane;
8-(p-octyloxybenzoyl)amino-2-(5-tetrazolyl)-1,4-benzodioxane-7-carboxylic acid,
8-[p-(2E-octyloxybenzoyl)amino-2-(5-tetrazolyl)-1,4-benzodioxane,
8-[p-(3-butenyloxy)benzoyl)amino-2-(5-tetrazolyl)-1,4-benzodioxane,
8-[p-(3Z-hexenyloxy)benzoyl)amino-2-(5-tetrazolyl)-1,4-benzodioxane,
8-[p-(2Z-octenyloxy)benzoyl)amino-2-(5-tetrazolyl)-1,4-benzodioxane,
8-[p-(2E-nonenyloxy)benzoyl)amino-2-(5-tetrazolyl)-1,4-benzodioxane,
8-[N-methyl-N-[p-(2E-cctenyloxy)benzoyl)amino-2-(5-tetrazolyl)-1,4-benzodioxane,
8-[p-(2E-hexenyloxy)benzoyl)amino-2-(5-tetrazolyl)-1,4-benzodioxane,
8-[p-(3E-heptenyloxy)benzoyl)amino-2-(5-tetrazolyl)-1,4-benzodioxane,
8-[p-(2E-octenyloxy)benzoyl)amino-1,4-benzodioxane-2-carboxylic acid and methyl ester thereof,
8-[p-(2E-heptenyloxy)benzoyl)amino-2-(5-tetrazolyl)-1,4-benzodioxane,
8-[p-(4-pentenyloxy)benzoyl)amino-2-(5-tetrazolyl)-1,4-benzodioxane,
8-[p-(2E-decenyloxy)benzoyl)amino-2-(5-tetrazolyl)-1,4-benzodioxane,
8-(p-geranyloxy)benzoyl)amino-2-(5-tetrazolyl)-1,4-benzodioxane,
8-[p-(2E,7-octadienyloxy)benzoyl)amino-2-(5-tetrazolyl)-1,4-benzodioxane,
8-[p-(2E-pentenyloxy)benzoyl)amino-2-(5-tetrazolyl)-1,4-benzodioxane,
8-[p-(2E-butenyloxy)benzoyl)amino-2-(5-tetrazolyl)-1,4-benzodioxane,
8-[p-(3E-octenyloxy)benzoyl)amino-2-(5-tetrazolyl)-1,4-benzodioxane,
8-[p-(7-octenyloxy)benzoyl)amino-2-(5-tetrazolyl)-1,4-benzodioxane, 8-[p-(2E,4E-octadienyloxy)benzoyl)amino-2-(5-tetrazolyl)-1,4-benzodioxane and
8-[p-(2E-octadienyloxy)benzoyl)amino-2-(5-tetrazolyl)-1,4-benzodioxane,
8-[p-(2-octynyloxy)benzoyl)amino-2-(5-tetrazolyl)-1,4-benzodioxane,
8-[p-(2-octynyloxy)benzoyl]amino-1,4-benzodioxane-2-carboxylic acid and methyl ester thereof and
8-[p-(2-isooctynyloxy)benzoyl]amino-2-(5-tetrazolyl)-1,4-benzodioxane
8-(p-pentylthiobenzoyl)amino-2-(5-tetrazolyl)-1,4-benzodioxane,
8-(m-pentylthiobenzoyl)amino-2-(5-tetrazolyl)-1,4-benzodioxane
8-(o-pentylthiobenzoyl)amino-2-(5-tetrazolyl)-1,4-benzodioxane and
8-(p-heptylthiobenzoyl)amino-2-(5-tetrazolyl)-1,4-benzodioxane
8-[p-(6-chlorohexyloxy)benzoyl]amino-2-(5-tetrazolyl)-1,4-benzodioxane,
8-[p-(5-chloropentyloxy)benzoyl]amino-2-(5-tetrazolyl)-1,4-benzodioxane,
8-[p-(4-chlorobutoxy)benzoyl]amino-2-(5-tetrazolyl)-1,4-benzodioxane,
8-[p-(7-chloroheptyloxy)benzoyl]amino-2-(5-tetrazolyl)-1,4-benzodioxane,
8-[p-(8-chlorooctyloxy)benzoyl]amino-2-(5-tetrazolyl)-1,4-benzodioxane,
8-[p-(9-chlorononyloxy)benzoyl]amino-2-(5-tetrazolyl)-1,4-benzodioxane and
8-[p-(t-bromopentyloxy)benzoyl]amino-2-(5-tetrazolyl)-1,4,-benzodioxane-2-carboxylic acid and methyl ester thereof
8-[p-hexyloxymethyl)benzoyl]amino-2-(5-tetrazolyl)-1,4-benzodioxane
8-[p-(cyclohexylmethoxy)benzoyl]amino-2-(5-tetrazolyl)-1,4-benzodioxane,
8-[p-(4-cyclohexylbutoxy)benozyl]amino-2-(5-tetrazolyl)-1,4-benzodioxane, and
8-[p-(2-cyclohexylethoxy)benzoyl')amino-2-(5-tetrazolyl)-1,4-benzodioxane, and
8-[p-(p-butylphenyl)methoxybenoyl]amino-2-(5-tetrazolyl)-1,4-benzodioxane,
8-[p-(5-phenylpentyloxy)benzoyl]amino-2-(5-tetrazolyl)-1,4-benzodioxane,
8-[p-(3-phenylpropoxy) benzoyl')amino-2-(5-tetrazolyl)-1,4-benzodioxane,
8-[p-(p-propylphenyl)methoxybenzoyl]amino-2-(5-tetrazolyl)-1,4-benzodioxane,
8-[p-(3-phenyl-2-propenyloxy)benzoyl]amino-2-(5-tetrazolyl)-1,4-benzodioxane,
8-[p-(4-phenylbutoxy)benzoyl]amino-2-(5-tetrazolyl)-1,4-benzodioxane,
8-[p-(o-pentylphenyl)methoxybenzoylamino-2-(5-tetrazolyl)-1,4-benzodioxane,
8-[p-(m-butylphenylmethoxybenzoyl]amino-2-(5-tetrazolyl)-1,4-benzodioxane,
8-(p-phenylmethoxybenzoyl)amino-2-(5-tetrazolyl)-1,4-benzodioxane,
8-[p-(2-phenylethoxy)benzoyl')amino-2-(5-tetrazolyl)1,4-benzodioxane,
8-[p-4-phenylbutoxy)benzoyl]amino-2-(5-tetrazolyl)-1,4-benzodioxane,
8-[p[-2-(2-naphthyl)ethoxy]benzoyl')amino-2-(5-tetrazolyl)-1,4-benzodioxane,
8-[p-[3-(p-chlorophenyl)propoxy]benzoyl]amino-2-(5-tetrazolyl)-1,4-benzodioxane and
8-[p-[4-(p-chlorophenyl)butoxy]benzoyl]amino-2-(5-tetrazolyl)-1,4-benzodioxane,
8-[p-(5-methoxycarbonylpen,tyloxy)benzoyl]amino-2-(5-tetrazolyl)-1,4-benzodioxane,
8-[p-(6-acetyloxyhexyloxy)benzoyl]amino-2-(5-tetrazxolyl)-1,4-benzodioxane,
8-[p-(6-hydroxyhexyloxy)benzoyl]amino-2-(5-tetrazolyl)-1,4-benozdioxane,
8-[p-(2E-octenoyloxy)benzoyl]amino-2-(5-tetrazolyl)-1,4-benzodioxane and
8-(p-octanoylbenzoyl)amino-2-(5-tetrazolyl)-1,4-benzodioxane
8-[p-(3-phenylthiopropoxy)benzoyl]amino-2-(5-tetrazolyl)-1,4-benzodioxane,
8-[p-(3-phenoxypropoxy)benzoyl]amino-2-(5-tetrazolyl)-1,4-benzodioxane,
8-[p-(2-phenylthioethoxy)benzoyl')amino-2-(5-tetrazolyl)-1,4-benzodioxane and
8-[p-(2-phenoxyethoxy)benzoyl')amino-2-(5-tetrazolyl)-1,4-benzodioxane
8-[p-[2-(3-thienyl)ethoxy]benzoyl]amino-2-(5-tetrazolyl)-1,4-benzodioxane and
8-[p-[4-(2-thienyl)butoxy]benzoyl')amino-2-(5-tetrazolyl)-1,4-benodioxane
8-[p-(5-azidopenyloxy)benozyl]amino-2-(5-tetrazolyl)-1,4-benzodioxane,
8-[p-(5-dimethylaminopentyloxy)benzoyl]amino-2-(5-tetrazolyl)-1,4-benzodioxane,
8-[p-(4-nitrobutoxy)benzoylamino-2-(5-tetrazolyl)-1,4-benzodioxane,
8-[p-(2-azidoethoxy)benzoyl]amino-2-(5-tetrazolyl)-1,4-benzodioxane,
8-[p-(4-azidobutoxy)benzoyl]amino-2-(5-tetrazolyl)-1,4-benzodioxane,
8-[p-(2-octenoylamino)benzoyl')amino-2-(5-tetrazolyl)-1,4-benzodioxane,
8-(p-pentyloxy-m-methoxybenzoyl)amino-2-(5-tetrazolyl)-1,4-benzodioxane,
8-[p-(2E-octenyloxy)-m-chlorobenzoy]amino-2-(5-tetrazolyl)-1,4-benzodioxane
8-(2-naphthylcarbonyl)amino-2-(5-tetrazolyl)-1,4-benzodioxane,
8-(p-pentylcinnamoyl)amino-2-(5-tetrazolyl)-1,4-benzodioxane,
8-(p-pentylcinnamoyl)amino-1,4-benzodioxane-2-carboxylic acid and methyl ester thereof,
8-(p-heptylcinnamoyl)amino-2-(5-tetrazolyl)-1,4-benzodioxane,
8-[N-methyl-[N-(pentylcinnamoyl)]amino]-2-(5-tetrazolyl)-1,4-benzodioxane,
5-(p-pentylcinnamoyl)amino-2-(5-tetrazolyl)-7-chloro-1,4-benzodioxane,
8-(p-pentylcinnamoyl)amino-2-(5-tetrazolyl)-6-chloro-1,4-benzodioxane,
8-(p-ethylcinnamoyl)amino-2-(5-tetrazolyl)-1,4-benzodioxane,
8-(p-propylcinnamoyl)amino-2-(5-tetrazolyl)-1,4-benzodioxane,
8-(p-butylcinnamoyl)amino-2-(5-tetrazolyl)-1,4-benzodioxane,
8-(p-pentylcinnamoyl)amino-2-(5-tetrazolyl)-6-methyl-1,4-benzodioxane,
8-(o-pentylcinnamoyl)amino-2-(5-tetrazolyl)-1,4-benzodioxane,
8-(m-octylcinnamoyl)amino-2-(5-tetrazolyl)-1,4-benzodioxane,
8-(p-pentylcinnamoyl)amino-2-(5-tetrazolyl)-1,4-benzodioxane-5-carboxylic acid and methyl ester thereof, 5-(p-pentylcinnamoyl)amino-2-(5-tetrazolyl)-1,4-benzodioxane-8-carboxylic acid and methyl ester thereof,
8-(p-hexylcinnamoyl)amino-2-(5-tetrazolyl)-1,4-benzodioxane,
8-(p-nonylcinnamoyl)amino-2-(5-tetrazolyl)-1,4-benzodioxane,
8-(p-pentylcinnamoyl)amino-2-(5-tetrazolyl)-1,4-benzodioxane-6-carboxylic acid and methyl ester thereof,
5-(p-pentylcinnamoyl)amino-2-(5-tetrazolyl)-1,4-benzodioxane-7-carboxylic acid and methyl ester thereof,
8-(p-octylcinnamoyl)amino-2-(5-tetrazolyl)-1,4-benzodioxane,
8-(p-decylcinnamoyl)amino-2-(5-tetrazolyl)-1,4-benzodioxane,
8-P-isopropylcinnamoyl)amino-2-(5-tetrazolyl)-1,4-benzodioxane,
8-(p-isobutylcinnamoyl)amino-2-(5-tetrazolyl)-1,4-benzodioxane,
8-(p-isopentylcinnamoyl)amino-2-(5-tetrazolyl)-1,4-benzodioxane,
8-(p-pentyl-2-methylcinnamoyl)amino-2-(5-tetrazolyl)-1,4-benzodioxane,
8-(p-pentyl-3-methylcinnamoyl)amino-2-(5-tetrazolyl)-1,4-benzodioxane and
8-(p-pentylcinnamoyl)amino-2-(5-tetrazolyl)methyl-1,4-benzodioxane
8-(p-pentyloxycinnamoyl)amino-2-(5-tetrazolyl)-1,4-benzodioxane,
8-(m-pentyloxycinnamoyl)amino-2-(5-tetrazolyl)-1,4-benzodioxane,
8-(o-pentyloxycinnamoyl)amino-2-(5-tetrazoly)-1,4-benzodioxane,
8-(p-propoxycinnamoyl)amino-2-(5-tetrazolyl)-1,4,-benzodioxane,
8-(p-butoxycinnamoyl)amino-2-(5-tetrazolyl)-1,4-benzodioxane,
8-(p-octyloxycinnamoyl)amino-2-(5-tetrazolyl)-1,4-benzodioxane,
8-(p-hexyloxycinnamoyl)amino-2-(5-tetrazolyl)-1,4-benzodioxane,
8-(p-heptyloxycinnamoyl)amino-2-(5-tetrazolyl)-1,4-benzodioxane,
8-(p-isopentyloxycinnamoyl)amino-2-(5-tetrazolyl)-1,4-benzodioxane,
8-(p-isohexyloxycinnamoyl)amino-2-(5-tetrazolyl)-1,4-benzodioxane,
8-[p-(1-methylbutoxy)cinnamoyl]amino-2-(5-tetrazolyl)-1,4-benzodioxane,
8-(p-isoheptyloxycinnamoyl)amino-2-(5-tetrazolyl)-1,4-benzodioxane,
8-(p-isooctyloxycinnamoyl)amino-2-(5-tetrazolyl)-1,4-benzodioxane,
8-(p-isohexyloxy-2-methylcinnamoyl)amino-2-(5-tetrazolyl)-1,4-benzodioxane and
8-(p-isohexyloxy-2-phenylcinnamoyl)amino-2-(5-tetrazolyl)-1,4-benzodioxane,
8-[p-(2E-octenyloxy)cinnamoyl]amino-2-(5-tetrazolyl)-1,4-benzodioxane,
8-[p-(2-propenyloxy)cinnamoyl]amino-2-(5-tetrazolyl)-1,4-benzodioxane,
8-[p-(3-butenyloxy)cinnamoyl]amino-2-(5-tetrazolyl)-1,4-benzodioxane,
8-[p-(3Z-hexenyloxy)cinnamoyl]amino-2-(5-tetrazolyl)1,4-benzodioxane,
8-[p-2Z-pentenyloxycinnamoyl]amino-2-(5-tetrazolyl)-1,4-benzodioxane,
8-[p-(2E-nonenyloxy)cinnamoyl]amino-2-(5-tetrazolyl)-1,4-benzodioxane,
8-[p-(3E-heptenyloxy)cinnamoyl]amino-2-(5-tetrazolyl)-1,4-benzodioxane,
8-[p-(2E-heptenyloxy)cinnamoyl]amino-2-(5-tetrazolyl)-1,4-benzodioxane,
8-[p-(2E-hexenyloxy)cinnamoyl]amino-2-(5-tetrazolyl)-1,4-benzodioxane,
8-[p-(2E-pentenyloxy)cinnamoyl]amino-2-(5-tetrazolyl)1,4-benzodioxane,
8-[p-(4-pentenyloxy)cinnamoyl]amino-2-(5-tetrazolyl)1,4-benzodioxane,
8-[p-(2E-butenyloxy)cinnamoyl]amino-2-(5-tetrazolyl)-1,4-benzodioxane and
8-[p-(2E-decenyloxy)cinnamoyl]amino-2-(5-tetrazolyl)-1,4-benzodioxane
8-[p-(2-octynyloxy)cinnamoyl]amino-2-(5-tetrazolyl)-1,4-benzodioxane and
8-[p-(2-pentynyloxy)cinnamoyl]amino-2-(5-tetrazolyl)-1,4-benzodioxane,
8-(p-pentylthiocinnamoyl)amino-2-(5-tetrazolyl)-1,4-benzodioxane,
8-(m-pentylthiocinnamoyl)amino-2-(5-tetrazolyl)-1,4-benzodioxane and
8-(o-pentylthiocinnamoyl)amino-2-(5-tetrazolyl)-1,4-benzodioxane,
8-[p-(6-chlorohexyloxy)cinnamoyl]amino-2-(5-tetrazolyl)1,4-benzodioxane,
8-[p-(4-chlorobutoxy)cinnamoyl]amino-2-(5-tetrazolyl)-1,4-benzodioxane,
8-[p-(5-chloropentyloxy)cinnamoyl]amino-2-(5-tetrazolyl)-1,4-benzodioxane and
8-[p-(7-chloroheptyloxy)cinnamoyl')amino-2-(5-tetrazolyl)-1,4-benzodioxane
8-(p-isopentyloxymethyl-cinnamoyl)amino-2-(5-tetrazolyl)-1,4-benzodioxane,
8-(p-cyclohexylcinnamoyl)amino-2-(5-tetrazolyl)-1,4-benzodioxane,
8-(p-cyclohexylmethoxycinnamoyl)amino-2-(5-tetrazolyl)-1,4-benzodioxane,
8-[p-(4-cyclohexylbutoxy)cinnamoyl')amino-2-(5-tetrazolyl)-1,4-benzodioxane and
8-[p-(2-cyclohexylethoxy)cinnamoyl]amino-2-(5-tetrazolyl)-1,4-benzodioxane,
8-(p-phenylmethylcinnamoyl)amino-2-(5-tetrazolyl)-1,4-benzodioxane,
8-(p-phenylmethoxycinnamoyl)amino-2-(5-tetrazolyl)-1,4-benzodioxane,
8-[p-(2-phenylethoxy)cinnamoyl]amino-2-(5-tetrazolyl)-1,4-benzodioxane,
8-[p-(4-phenylbutoxy)cinnamoyl]amino-2-(5-tetrazolyl)-1,4-benzodioxane,
8-[p-(5-phenylpentyloxy)cinnamoyl]amino-2-(5-tetrazolyl)-1,4-benzodioxane and
8-[p-(3-phenylpropoxy)cinnamoyl]amino-2-(5-tetrazolyl)-1,4-benzodioxane,
8-[p-(6-acetyloxyhexyloxy)cinnamoyl]amino-2-(5-tetrazolyl)-1,4-benzodioxane,
8-[p-[2-(2-thienyl)ethoxy)-cinnamoyl]-amino-2-(5-tetrazolyl)-1,4-benzodioxane,
8-(m,p-dimethoxycinnamoyl)amino-2-(5-tetrazolyl)-1,4-benzodioxane,
8-(m-methoxy-p-pentyloxycinnamoyl)amino-2-(5-tetrazolyl)-1,4-benzodioxane and
8-(p-pentyloxy-m-chlorocinnamoyl)amino-2-(5-tetrazolyl)-1,4-benzodioxane
8-[3-(5-indanyl)acryloyl]amino-2-(5-tetrazolyl)-1,4-benzodioxane,
N-(2-hexadecenoyl)amino-2-(5-tetrazolyl)-1,4-benzodioxane, 8-(p-pentylphenylacetyl)amino-2-(5-tetrazolyl)-1,4-benzodioxane and
8-[3-(p-pentylphenyl)propionyl]amino-2-(5-tetrazolyl)-1,4-benzodioxane
8-(p-hexylphenylpropioloyl)amino-2-(5-tetrazolyl)-1,4-benzodioxane,
8-[5-(p-propoxyphenyl)penta-2E,4E-dienoyl]amino-2-(5-tetrazolyl)-1,4-benzodioxane and
8-[5-(p-butylphenyl)penta-2E,4E-dienoyl]amino-2-(5-tetrazolyl)-1,4-benzodioxane,
8-(p-pentylcinnamoyl)amino-2-(5-tetrazolyl)-2,3-dihydro-14-dithianaphthalene and
5-(p-pentylcinnamoyl)amino-2-(5-tetrazolyl)-2,3-dihydro-1,4-dithianaphthalene and sodium salts thereof.

Also included are aromatic 1,2-di(thio)ethers of the formula:

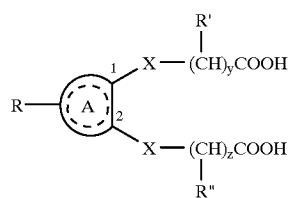

wherein
A is an 1,2-disubstituted aromatic ring; preferably a benzene ring;
wherein
X is independently O, S, SO, or $SO_2$;
R is H,
$C_1$–$C_4$ alkyl,
phenyl or substituted phenyl,
halo,
haloalkyl,
hydroxy,
carboxy,
cyano,
$C_1$–$C_4$ alkoxy,
$C_1$–$C_4$ alkylthio,
$C_1$–$C_4$ alkylsulfinyl,
$C_1$–$C_4$ alkylsulfonyl,
nitro,
amino,
$C_1$–$C_4$ mono or di-alkylamino;
R' and R" are independently
H,
halo,
$C_1$–$C_4$ alkyl or $C_1$–$C_4$ alkoxy,
amino, or oxo, where CH—R' or CH—R" in the formula become —C=O;
y is 1–6;
z is 6–20; and
wherein

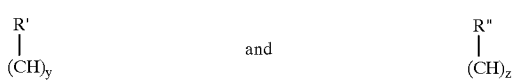

can independently represent substituted or unsubstituted alkyl radicals or alkenyl radicals containing at least one alkene bond;
and pharmaceutically acceptable salts and esters thereof.

The compounds of the instant invention are inhibitors of the human testosterone-5α-reductase enzyme.

The scope of the compounds of the instant invention are described by the above-described formula.

In the description of the formula the following terms are used which are hereby defined:

X in the general formula above is O or S, preferably where one X is O, and particularly where both Xs are O, e.g., resulting in the catechol structure.

"$C_1$–$C_4$ alkyl" includes linear or branched species, e.g. methyl, ethyl, n-propyl, isopropyl, cyclopropyl, n-butyl, isobutyl, sec-butyl, t-butyl.

"$C_1$–$C_4$ alkoxy" includes linear or branched species, e.g., methoxy, ethoxy, n-propoxy, isopropoxy, n-butoxy, isobutoxy, sec-butoxy, t-butoxy.

"Halo" includes fluoro, chloro, bromo or iodo.

"Substituted phenyl" includes phenyl substituted by one or more of $C_1$–$C_4$ alkyl, $C_1$–$C_4$ alkoxy, or halo, and the like, as defined above. representative examples include o, m-, p-methoxy phenyl; 2,4-dimethoxyphenyl; 2-chloro-4-ethoxyphenyl; 3,5-dimethoxyphenyl; 2,4-dichlorophenyl; 2-bromo-4-methylphenyl, o-fluorophenyl, and the like.

"Haloalkyl" includes $C_1$–$C_4$ alkyl, defined above, substituted with one or more "halo" as defined above and includes: trifluoromethyl, 2,2-dichloroethyl and the like.

"$C_1$–$C_4$ alkylthio" includes $C_1$–$C_4$ alkyl, defined above, substituted with at least one divalent thio (—S—) grouping including; methylthio, ethylthio, isopropylthio, n-butylthio, and the like.

"$C_1$–$C_4$ alkylsulfinyl" includes $C_1$–$C_4$ alkyl, defined above, substituted with at least one —SO— grouping including; methylsulfinyl, ethylsulfinyl; isopropylsulfinyl, and the like.

"$C_1$–$C_4$ alkylsulfonyl" includes $C_1$–$C_4$ alkyl, defined above, substituted with at least one sulfonyl group, —$SO_2$—, including; methylsulfonyl, ethylsulfonyl, isopropylsulfonyl, n-butylsulfonyl, and the like.

"$C_1$–$C_4$ mono or dialkyl amino" includes amino, substituted with one or more $C_1$–$C_4$ alkyl groups as defined hereinabove, including: methylamino, ethylamino, n-butylamino, t-butylamino, N,N-dimethylamino, N,N-diethylamino, methyl-t-butylamino, and the like.

The R group or groups on the benzene ring can be present initially in the process, such as in starting material I in Flow Chart A, e.g. phenyl, methyl, methoxy, cyano, trifluoromethyl, carbomethoxy, or added later by a conventional reaction, e.g. chloro, as by chlorination, nitro by nitration, or created from a starting or added functional group present, e.g. converting a nitro to an amino group by catalytic reduction, then alkylating to a mono or dialkylamine. An amino group can be subjected to diazotization to a hydroxy group, which can be followed by methylation to a methoxy group. Similarly, a hydroxy group can be converted to a thiol by the analogous procedures described in J. Org. Chem. 31, pp 3980–3984 (1966) by Newman and Karnes, and J. Org. Chem. 31, pp 410 (1966) by Kwart, H. and Evans, E. S. The resulting thiol can be alkylated to alkylthio, which can be oxidized to the corresponding sulfoxide or sulfone. Preferred substituents are H, $C_1$–$C_4$ alkyl, $C_1$–$C_4$ alkoxy and phenyl. These reactions and sequences are conventional in the art and it will be obvious to one skilled in the art to modify the benzene ring to arrive at an R radical disclosed herein.

By the term "pharmaceutically acceptable salts and esters thereof" is meant, salts and esters of the acid groups in the final molecule which can be used as part of the human drug delivery system and include the salts: sodium, potassium, calcium, ammonium, substituted ammonium, quaternary ammonium, and esters: ethyl ester, aceturate, besylate, edetate, phenpropionate, acetate, pamoate, and esters which serye as "prodrug" formulations which will hydrolyze in the body at physiological pH's to regenerate the acid, including pivaloylates, e.g. pivoxetil and pivoxil, and Kanebo esters, and the like.

where y is 1–6, preferably 3, can contain at least one R' substituent as defined above, and can be, e.g.,

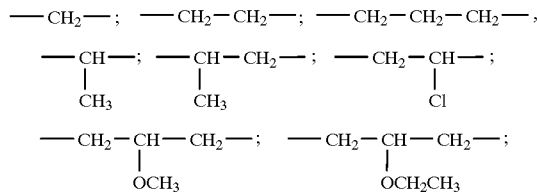

and the like.

An alkene bond can also be present in R'

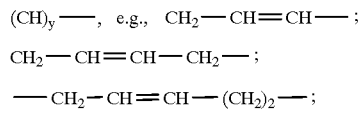

and the like.

where z is 6–20, preferably 10–16, can contain at least one R" substituent as defined above, and can be; e.g.,

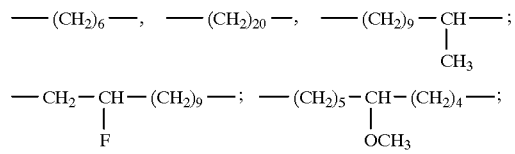

and the like.

An alkene bond can also be present in

e.g., $CH_2$—CH=CH—$(CH_2)_8$—; —$(CH_2)_8$—CH=CH$(CH_2)_2$—; —$(CH_2)_9$—CH=CH—$(CH_2)_9$—; $(CH_2)_4$—CH=CH—$(CH_2)_4$—; and the like.

R' and R" can also be —$NHCOCH_3$, which can be hydrolyzed to amino by conventional acid or base hydrolysis in the final molecule; R' and R" can also be oxo, obtained by, for example, HBr addition to an alkene followed by conversion to an alcohol and subsequent oxidation to the ketone.

Preferred is where one R' or R" is H and particularly preferred is where both

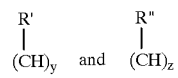

are alkyl.

Preferred compounds of the instant invention are given by the following formulas;

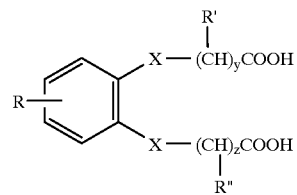

wherein one X is O and R, R', R", y and z are defined above; and particularly preferred are the compounds,

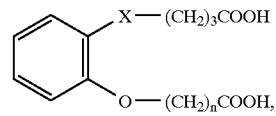

wherein

X is O or S and n is 10–16.

The compounds of the instant invention can be made by the procedure outlined in the following Flowchart A-1.

FLOW CHART A-1

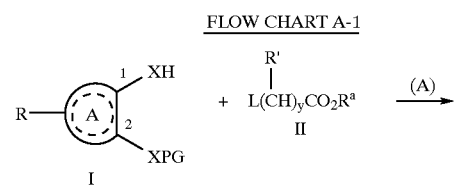

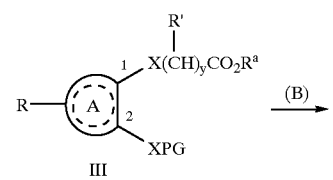

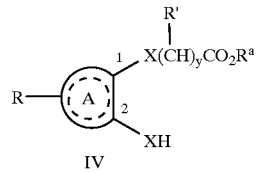

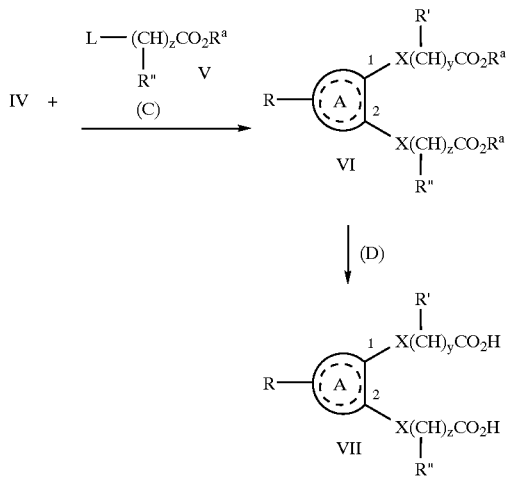

As seen in Flow Chart A-1, Compound I is the starting substrate in the invention process and is a 1,2-substituted benzene ring. X can be independently O or S and "PG" represents a hydroxy or thio protecting group which is inactive during Step (A) but can be subsequently removed by, e.g. palladium on carbon catalyst in ethanol under a pressurized $H_2$ atmosphere.

Examples of "PG" protecting groups which are conventional and known in the art (See "Protective Groups in Organic Synthesis" by Theodora W. Greene—1981—John Wiley—Chapter 2, "Protection for the Hydroxyl Group, Including 1,2- and 1,3-Diols" pp. 16–87 and Chapter 6 "Protection for the Thiol Group" pp. 193–218).

Representative examples of "PG" include: benzyl, p-methoxybenzyl, p-halobenzyl; including p-chlorobenzyl, p-fluorobenzyl, and the like. Other protective groups which are known will be obvious to one skilled in the art to carry out the function of Step (A).

Representive examples of compounds useful as I in the instant invention, include, but are not limited to the following:

2-(benzyloxy)-phenol,
2-benzyloxy-thiophenol,
2-(benzylthio)-phehol,
2-(benzylthio)thiophenol,
3-methoxy-2-benzyloxyphenol,
2-benzyloxy-4-methoxyphenol,
3-methyl-2-benzyloxyphenol,
2-benzyloxy-5-methylphenol,
2-benzyloxy-4-methylphenol,
2-benzyloxy-5-methylphenol,
2-benzyloxy-3,5-diisopropylphenol,
2-benzyloxy-3,5-di-t-butylphenol,
2-benzyloxy-4-t-butylphenol,
2-benzyloxy-3-ethylphenol,
2-benzyloxy-5-phenylphenol,
2-benzyloxy-4-methyl-1-thiophenol,
2-benzyloxy-5-trifluoromethyl-1-thiophenol,
2-benzyloxy-6-methoxy-1-thiophenol,
2-benzylthio-4-methyl-thiophenol,
2-benzylthio-5-methylsulfonyl-phenol, and the like.

Representative examples of II useful in the invention process where L is a leaving group, e.g., halogen, including bromo, chloro, or sulfonate, and the like, and $R^a$ is a $C_1$–$C_4$ linear or branched alkyl portion of the ester, including methyl, ethyl, isopropyl, t-butyl, sec-butyl, and the like, and where $R^1$ and Y are or defined above, include, but are not limited to:

Br—$CH_2$—COOMe,
Cl—$CH_2CH_2CH_2$COO$CH_2CH_3$,
Br—$CH_2CH_2CH_2CH_2$COOMe,
Br—$CH_2CH_2CH_2CH_2CH_2$COOEt,
Br—$CH_2CH_2CH_2CH_2CH_2CH_2$COO$CH_2CH_2CH_3$,
Br—$(CH_2)_2$CH($CH_3$)COOMe,
Br—$CH_2$CH($CH_3$)$CH_2$COOEt,
Br—$CH_2CH_2CH_2$COOMe,
Br—$CH_2$CH(O$CH_3$)$CH_2$COOCH($CH_3$)$_2$,
Cl—$CH_2$CH(O$CH_2CH_3$)$CH_2$COOMe,
Br—$CH_2$CH(F)$CH_2$COOMe,
Cl—$CH_2CH_2$COOEt,
and the like.

In Step (A) the condensation of I and II to produce III takes place in an non-hydroxylated polar organic solvent, e.g., acetone, ethyl acetate, methylethylketone, dioxan, THF, diethylketone, and the like, A proton acceptor is also present, e.g. potassium carbonate, sodium bicarbonate, pyridine, triethylamine, and the like. Generally, the reaction is carried out under an inert atomosphere, e.g. dry nitrogen, and heated at reflux or allowed to sit for an extended period of time at room temperature. Workup is conventional.

In Step (B) the protecting group, "PG", is catalytically removed at ambient temperature under a pressurized, hydrogen atmosphere in an organic solvent to produce IV, being a phenol or thiophenol. Operable catalysts include 5% Pd/C, and the like. The organic solvent should be inert under the reaction conditions and includes ethyl acetate, ethanol, methanol, dioxane, and the like.

Step (C) involves reacting IV with V to produce VI, the diester. The reaction conditions are similar to those described in Step (A) utilizing an inert organic solvent for the reactants and a proton acceptor.

Representative examples of V useful in the invention are:

Br($CH_2$)$_6$COOMe,
Br($CH_2$)$_7$COOMe,
Br($CH_2$)$_8$COOMe,
Br($CH_2$)$_9$COOMe,
Br($CH_2$)$_{10}$COOMe,
Br($CH_2$)$_{11}$COOMe,
Cl($CH_2$)$_{12}$COOEt,
Cl($CH_2$)$_{13}$COOCH($CH_3$)$_2$,
Cl($CH_2$)$_{14}$COO$CH_2CH_2CH_3$,
Br—($CH_2$)$_{15}$COOMe
Br—($CH_2$)$_{16}$COOMe
Br($CH_2$)$_{16}$COO$CH_2CH_3$,
Br($CH_2$)$_{17}$COOC($CH_3$)$_3$,
Br($CH_2$)$_{18}$COOMe,
Br($CH_2$)$_{19}$COOEt,
Br($CH_2$)$_{20}$COOMe,
Br($CH_2$)$_2$CH($CH_3$)—($CH_2$)$_{10}$COOMe,
Br—$CH_2$CH($CH_3$)($CH_2$)$_{10}$COOMe,
Br—$CH_2CH_3$CH($CH_3$)$CH_2$COOEt,
Br—$CH_2$CH(O$CH_3$)($CH_2$)$_7$COOCH($CH_3$)$_2$,
Cl—$CH_2$CH(O$CH_2CH_3$)$CH_2CH_2$COOMe,

Br—CH₂CH(NHCOCH₃)—(CH₂)₁₀—CH₂—COOMe,

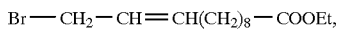

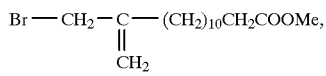

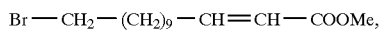

Br—CH₂—(CH₂)₉—CH=CH—COOMe,

Br—CH₂—(CH₂)₉—CH=CH—COOMe, and the like.

In Step (D), the diester can be deesterified by aqueous basic hydrolysis, e.g. NaOH in MeOH/H₂O to yield the diacid VII upon acidification.

FLOW CHART B-1

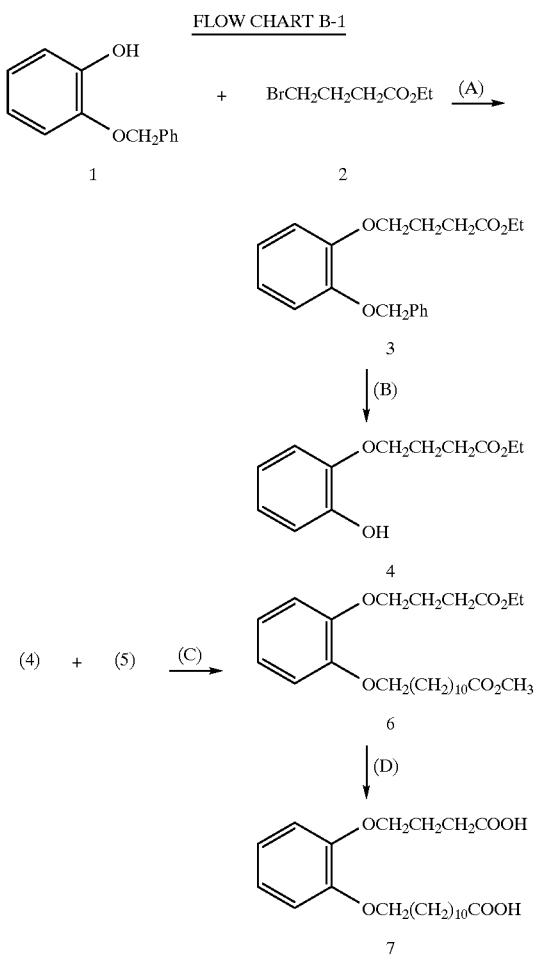

FLOW CHART C-1

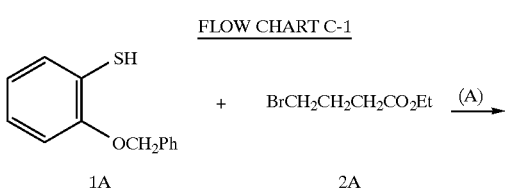

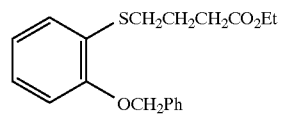

3A

↓(B)

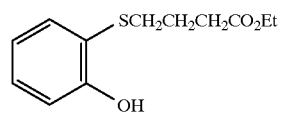

4A (4A) + (5) —(C)→

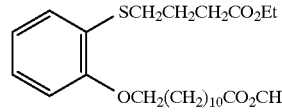

6A

↓(D)

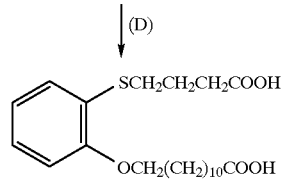

7A

Flow Sheet B-1 illustrates the specific synthesis of 7.

As seen, 2-benzyloxyphenol 1, ethyl 4-bromobutyrate 2 and anhydrous K₂CO₃ in e.g., dry acetone are heated at reflux or stirred for an extended period of time at room temperature, under a nitrogen atmosphere to give product ethyl 4-(2-benzyloxyphenoxy) butyrate 3, in Step (A).

A solution of 3 in e.g., ethyl acetate is catalytically hydrogenated at room temperature under e.g. 40 psig of H₂ in the presence of a 5% Pd/C catalyst to yield ethyl 4-(2-hydroxyphenoxy) butyrate 4 in Step (B).

Step (C) comprises reacting 4 and methyl 12-bromododecanoate 5 with potassium carbonate in acetone as in Step (A) to obtain the monomethyl ester 6.

In Step (D), the diester 6 is de-esterified by e.g., 2.5 N NaOH in MeOH/H₂O to yield the final product, diacid 7, upon acidification.

Flow Sheet C-1 illustrates the synthesis of the sulfur analog of 7 as 7A. This analogous procedure uses substantially the same steps as involved in Flow Sheet B.

It is also obvious from the above Flow Sheets that suitable replacement compounds for II and 2 with other substituted and unsubstituted halo alkyl esters, known in the art and described herein, and that suitable replacement of V and 5 with other bromoesters, available in the art and also described above will yield all of the compounds within the scope of the instant claims.

Representative examples of compounds produced by this process include:
4-(2-(20-Carboxyeicosyloxy)phenoxy)butyric acid;
4-(2-(19-Carboxynonadecyloxy)phenoxy)butyric acid;
4-(2-(18-Carboxyoctadecyloxy)phenoxy)butyric acid;
4-(2-(17-Carboxyheptadecyloxy)phenoxy)butyric acid;
4-(2-(16-Carboxyhexadecyloxy)phenoxy)butyric acid;
4-(2-(15-Carboxypentadecyloxy)phenoxy)butyric acid;
4-(2-(14-Carboxytetradecyloxy)phenoxy)butyric acid;
4-(2-(13-Carboxytridecyloxy)phenoxy)butyric acid;

4-(2-(12-Carboxydodecyloxy)phenoxy)butyric acid;
4-(2-(11-Carboxyundecyloxy)phenoxy)butyric acid;
4-(2-(10-Carboxydecyloxy)phenoxy)butyric acid;
4-(2-(9-Carboxynqnyloxy)phenoxy)butyric acid;
4-(2-(8-Carboxyoctyloxy)phenoxy)butyric acid;
4-(2-(7-Carboxyheptyloxy)phenoxy)butyric acid;
4-(2-(6-Carboxyhexyloxy)phenoxy)butyric acid;
4-(2-(20-Carboxyeicosyloxy)phenylthio)butyric acid;
4-(2-(19-Carboxynonadecyloxy)phenylthio)butyric acid;
4-(2-(18-Carboxyoctadecyloxy)phenylthio)butyric acid;
4-(2-(17-Carboxyheptadecyloxy)phenylthio)butyric acid;
4-(2-(16-Carboxyhexadecyloxy)phenylthio)butyric acid;
4-(2-(15-Carboxypentadecyloxy)phenylthio)butyric acid;
4-(2-(14-Carboxytetradecyloxy)phenylthio)butyric acid;
4-(2-(13-Carboxytridecyloxy)phenylthio)butyric acid;
4-(2-(12-Carboxydodecyloxy)phenylthio)butyric acid;
4-(2-(11-Carboxyundecyloxy)phenylthio)butyric acid;
4-(2-(10-Carboxydecyloxy)phenylthio)butyric acid;
4-(2-(9-Carboxynonyloxy)phenylthio)butyric acid;
4-(2-(8-Carboxyoctyloxy)phenylthio)butyric acid;
4-(2-(7-Carboxyheptyloxy)phenylthio)butyric acid;
4-(2-(6-Carboxyhexyloxy)phenylthio)butyric acid;
4-(2-(20-Carboxyeicosylthio)phenoxy)butyric acid;
4-(2-(19-Carboxynonadecylthio)phenoxy)butyric acid;
4-(2-(18-Carboxyoctadecylthio)phenoxy)butyric acid;
4-(2-(17-Carboxyheptadecylthio)phenoxy)butyric acid;
4-(2-(16-Carboxyhexadecylthio)phenoxy)butyric acid;
4-(2-(15-Carboxypentadecylthio)phenoxy)butyric acid;
4-(2-(14-Carboxytetradecylthio)phenoxy)butyric acid;
4-(2-(13-Carboxytridecylthio)phenoxy)butyric acid;
4-(2-(12-Carboxydodecylthio)phenoxy)butyric acid;
4-(2-(11-Carboxyundecylthio)phenoxy)butyric acid;
4-(2-(10-Carboxydecylthio)phenoxy)butyric acid;
4-(2-(9-Carboxynonylthio)phenoxy)butyric acid;
4-(2-(8-Carboxyoctylthio)phenoxy)butyric acid;
4-(2-(7-Carboxyheptylthio)phenoxy)butyric acid;
4-(2-(6-Carboxyhexylthio)phenoxy)butyric acid;
4-(2-(20-Carboxyeicosylthio)phenylthio)butyric acid;
4-(2-(19-Carboxynonadecylthio)phenylthio)butyric acid;
4-(2-(18-Carboxyoctadecylthio)phenylthio)butyric acid;
4-(2-(17-Carboxyheptadecylthio)phenylthio)butyric acid;
4-(2-(16-Carboxyhexadecylthio)phenylthio)butyric acid;
4-(2-(15-Carboxypentadecylthio)phenylthio)butyric acid;
4-(2-(14-Carboxytetradecylthio)phenylthio)butyric acid;
4-(2-(13-Carboxytridecylthio)phenylthio)butyric acid;
4-(2-(12-Carboxydodecylthio)phenylthio)butyric acid;
4-(2-(11-Carboxyundecylthio)phenylthio)butyric acid;
4-(2-(10-Carboxydecylthio)phenylthio)butyric acid;
4-(2-(9-Carboxynonylthio)phenylthio)butyric acid;
4-(2-(8-Carboxyoctylthio)phenylthio)butyric acid;
4-(2-(7-Carboxyheptylthio)phenylthio)butyric acid;
4-(2-(6-Carboxyhexylthio)phenylthio)butyric acid;
3-(2-(16-Carboxyhexadecyloxy)phenoxy)propionic acid;
3-(2-(15-Carboxyisohexadecyloxy)phenoxy)butyric acid;
3-(2-(14-Carboxytetradecyloxy)phenoxy)butyric acid;
5-(2-(13-Carboxytridecyloxy)phenoxy)valeric acid;
5-(2-(12-Carboxydodecyloxy)phenoxy)valeric acid;
5-(2-(11-Carboxyisododecyloxy)phenoxy)valeric acid;
4-(2-(11-Carboxyundecyloxy)phenoxy)valeric acid;
4-(2-(10-Carboxydecyloxy)phenoxy)valeric acid;
4-(2-(9-Carboxynonyloxy)phenoxy)valeric acid;
6-(2-(9-Carboxynonyloxy)phenoxy)caproic acid;
6-(2-(8-Carboxyoctyloxy)phenoxy)caproic acid;
6-(2-(7-Carboxyisooctyloxy)phenoxy)caproic acid;
7-(2-(7-Carboxyheptyloxy)phenoxy)enanthic acid;
7-(2-(6-Carboxyhexyloxy)phenoxy)enanthic acid;
7-(2-(5-Carboxyisohexyloxy)phenoxy)enanthic acid;

2-(2-(12-Carboxydodecylthio)phenoxy)acetic acid;
2-(2-(11-Carboxydecylthio)phenoxy)acetic acid;
2-(2-(10-Carboxydecylthio)phenoxy)acetic acid;
3-(2-(9-Carboxynonyloxy)phenylthio)propionic acid;
3-(2-(12-Carboxydodecyloxy)phenylthio)propionic acid;
3-(2-(11-Carboxyundecyloxy)phenylthio)propionic acid;
3-(2-(11-Carboxyundecyloxy)phenylthio)butyric acid;
3-(2-(11-Carboxyundecyloxy)-4-methyl-phenylthio)butyric acid;
3-(2-(12-Carboxydodecylthio)phenylthio)butyric acid;
5-(2-(11-Carboxyundecylthio)phenylthio)valeric acid;
5-(2-(10-Carboxydecyloxy)phenylthio)valeric acid;
5-(2-(9-Carboxynonyloxy)phenylthio)valeric acid;
3-(2-(12-Carboxydodecyloxy)phenylthio)valeric acid;
3-(2-(11-Carboxydecyloxy)phenylthio)valeric acid;
3-(2-(10-Carboxydecyloxy)phenylthio)valeric acid;
6-(2-(9-Carboxynonylthio)phenylthio)caproic acid;
6-(2-(12-Carboxydodecyloxy)phenylthio)caproic acid;
6-(2-(11-Carboxyundecyloxy)phenylthio)caproic acid;
6-(2-(11-Carboxyundecyloxy)-3-methylphenylthio)-enanthic acid;
7-(2-(11-Carboxyundecyloxy)-4-methylphenylthio)-enanthic acid;
7-(2-(12-Carboxydodecylthio)phenoxy)enanthic acid;
4-(2-(11-Carboxyundecyloxy)4-methyl-phenoxy)butyric acid;
4-(2-(10-Carboxydecyloxy)3-methylphenoxy)butyric acid;
4-(2-(9-Carboxynonyloxy)5-methylphenoxy)butyric acid;
4-(2-(12-Carboxydodecyloxy)6-methylphenoxy)butyric acid;
4-(2-(12-Carboxydodecyloxy)6-methylphenoxy)butyric acid;
4-(2-(11-Carboxyundecylthio)-3-(methylthio)phenoxy)-valeric acid;
4-(2-(11-Carboxyundecylthio)-3-(methylsulfonyl)phenoxy)butyric acid;
4-(2-(11-Carboxyundecyloxy)-4-(methylsulfonyl)phenoxy)butyric acid;
4-(2-(12-Carboxydodecyloxy)5-ethyl-phenoxy)butyric acid;
4-(2-(11-Carboxyundecyloxy)4-phenylphenoxy)butyric acid;
4-(2-(10-Carboxydecyloxy)-3,5-dimethylphenoxy)butyric acid;
4-(2-(9-Carboxynonyloxy)-4-fluoro-phenoxy)butyric acid;
4-(2-(12-Carboxydodecyloxy)-5-(trifluoromethyl)-phenoy)butyric acid;
4-(2-(12-Carboxydodecylthio)-5-nitrophenoxy)butyric acid;
4-(2-(11-Carboxyundecylthio)-4-methylphenoxy)valeric acid;
4-(2-(11-Carboxyundecylthio)-3,5-di-methylphenoxy)-butyric acid;
4-(2-(12-Carboxydodecyloxy)-4-(dimethylamino)phenoxy)-butyric acid;
4-(2-(11-Carboxyundecyloxy)-5-(ethylamino)phenoxy)-butyric acid;
2-(2-(9-Carboxynonyloxy)phenoxy)propionic acid;
3-(2-(12-Carboxydodecyloxy)phenoxy)-3-methylpropionic acid;
4-(2-(10-Carboxydecyloxy)phenylthio)-3-methoxy-butyric acid;
4-(2-(9-Carboxynonyloxy)phenylthio)-3-ethoxy-butyric acid;
4-(2-(11-Carboxyundecyloxy)phenoxy)but-2-enoic acid;
4-(2-(9-Carboxynonyloxy)phenoxy)-2-butenoic acid;
4-(2-(11-Carboxy-2-methylundecyloxy)phenoxy)butyric acid;

4-(2-(11-Carboxyundecyl-7-ene-oxy)phenoxy)butyric acid;
4-(2-(13-Carboxy-2-methylene-tri-decyloxy)phenoxy)-butyric acid;
4-(2-(11-Carboxyundecyloxy)phenylsulfonyl)butyric acid;
4-(2-(11-Carboxyundecyloxy)phenylsulfinyl)butyric acid;
4-(2-(11-Carboxyundecylsulfinyl)phenoxy)butyric acid;
4-(2-(11-Carboxyundecylsulfonyl)phenoxy)butyric acid;
4-(2-(11-Carboxyundecylsulfinyl)phenylsulfinyl)butyric acid;
4-(2-(11-Carboxyundecylsulfonyl)phenylsulfonyl)butyric acid; and the like.

Also included as a 5α-reductase inhibitor in this invention is an agent for the treatment of prostatic cancer in combination with flutamide is of the following formula:

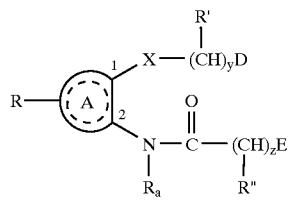

wherein
A is an 1,2-disubstituted aromatic ring selected from
(a) benzene, 1,2-disubstituted naphthalene;
(b) 5-6 membered heteroaromatic ring, containing 1-2 N atoms, 1 S or 0 atom, or combination thereof;
D and E are independently —COOH, —CONH$_2$, CONHR$_b$, COOR$_b$, SO$_2$OH, SO$_3$(OH), SO$_2$NH$_2$, —SSO$_2$ONa, PH(O)(OH), P(O)(OH)$_2$;
X is O, S, SO or SO$_2$;
R is H,
C$_1$–C$_4$ alkyl,
phenyl or substituted phenyl,
halo,
haloalkyl,
hydroxy,
carboxy,
cyano,
C$_1$–C$_4$ alkoxy,
C$_1$–C$_4$ alkylthio,
C$_1$–C$_4$ alkylsulfinyl,
C$_1$–C$_4$ alkylsulfonyl,
nitro,
amino,
C$_1$–C$_4$ mono or di-alkylamino;
R' and R" are independently
H
halo,
C$_1$–C$_4$ alkyl or C$_1$–C$_4$ alkoxy,
amino, or oxo, where CH—R' or CH—R" in the formula become —C=O;
R$_a$ is H, C$_1$–C$_4$ alkyl;
R$_b$ is C$_1$–C$_{12}$ alkyl, phenyl or phenyl C$_1$–C$_4$ alkyl;
y is 1–6;
z is 6–20; and
wherein

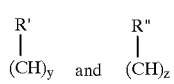

can independently represent substituted or unsubstituted alkyl radicals or alkenyl radicals containing at least one alkene bond;

and pharmaceutically acceptable salts and esters thereof.

The compounds of the instant invention are inhibitors of the human testosterone-5α-reductase The scope of the compounds of the instant invention are described by the above-described formula.

In the description of the formula the following terms are used which are hereby defined:

X is preferably O or S, and particularly preferred is O.

"C$_1$–C$_4$ alkyl" includes linear or branched species, e.g. methyl, ethyl, n-propyl, isopropyl, cyclopropyl, n-butyl, isobutyl, sec-butyl, t-butyl and "C$_1$–C$_{12}$ alkyl" includes, alkyl up to 12 cartons including n-octyl, t-decyl, n-dodecyl.

"Phenyl C$_1$–C$_4$ alkyl" includes benzyl, 2-phenethyl and the like.

"C$_1$–C$_4$ alkoxy" includes linear or branched species, e.g., methoxy, ethoxy, n-propoxy, isopropoxy, n-butoxy, isobutoxy, sec-butoxy, t-butoxy.

"Halo" includes fluoro, chloro, bromo or iodo.

By the term "heteroaromatic ring" as used herein is meant a 5–6 membered ring, containing 1–2 N-atoms, 1 S or O atom, or combination thereof, and includes: pyridine, thiophene, furan, imidazole, 1,3-thiazole, 1,3-oxazole, 1,2,3-thiadiazole, and the like. The limitation here being that the 1,2-disubstitution occurs on only ring carbons of the heteroaromatic ring. Preferred heteroaromatic rings are pyridine, furan and thiophene.

"Substituted phenyl" includes phenyl substituted by one or more of C$_1$–C$_4$ alkyl, C$_1$–C$_4$ alkoxy, or halo, and the like, as defined above; representative examples include o, m-, p-methoxy phenyl; 2,4-dimethoxyphenyl; 2-chloro-4-ethoxyphenyl; 3,5-dimethoxyphenyl; 2,4-dichlorophenyl; 2-bromo-4-methylphenyl, o-fluorophenyl, and the like.

"Haloalkyl" includes C$_1$–C$_4$ alkyl, defined above, substitued with one or more "halo" as defined above and inlcudes: trifluoromethyl, 2,2-dichloroethyl and the like.

"C$_1$–C$_4$ alkylthio" includes C$_1$–C$_4$ alkyl, defined above, substituted with at least one divalent thio (—S—) grouping including; methylthio, ethylthio, isopropylthio, n-butylthio, and the like.

"C$_1$–C$_4$ alkylsulfinyl" includes C$_1$–C$_4$ alkyl, defined above, substituted with at least one —SO— grouping including; methylsulfinyl, ethylsulfinyl; isopropylsulfinyl, and the like.

"C$_1$–C$_4$ alkylsulfonyl" includes C$_1$–C$_4$ alkyl, defined above, substituted with at least one sulfonyl group, —SO$_2$—, including; methylsulfonyl, ethylsulfonyl, isopropylsulfonyl, n-butylsulfonyl, and the like.

"C$_1$–C$_4$ mono or dialkyl amino" includes amino, substituted with one or more C$_1$–C$_4$ alkyl groups as defined hereinabove, including: methylamino, ethylamino, n-butylamino, t-butylamino, dimethylamino, diethylamino, methyl-t-butylamino, and the like.

The R group or groups on the benzene or heteroaromatic ring can be present initially in the process, e.g. phenyl, methyl, methoxy, cyano carbomethoxy, trifluoromethyl, (as in the starting o-nitrophenol 1 in Flow Chart A) or added later by a conventional reaction, e.g. chloro, as by chlorination, nitro by nitration, or created from a starting or added functional group present, e.g. converting a later added nitro group to an amino group by catalytic reduction, then alkylating to a mono or dialkylamine. An amino group can be subjected to diazotization to a hydroxy group, which can be followed by methylation to a methoxy group. Similarly, a hydroxy group can be converted to a thiol by the analogous procedures described in J. Org. Chem. 31, pp 3980–3984 (1966) by Newman and Karnes, and J. Org. Chem. 31, pp 410 (1966) by Kwart, H. and Evans, E. S. The resulting thiol can be alkylated to alkylthio, which can be oxidized to the corresponding sulfoxide or sulfone. Preferred substituents are H, $C_1$–$C_4$ alkyl, $C_1$–$C_4$ alkoxy and phenyl. These reactions and sequences are conventional in the art and it will be obvious to one skilled in the art to modify the benzene ring to arrive at an R radical disclosed herein.

By the term "pharmaceutically acceptable salts and esters thereof" is meant, salts and esters of the acid groups in the final molecule which can be used as part of the human drug delivery system and include the salts: sodium, potassium, calcium, ammonium, substituted ammonium, quaternary ammonium, and esters: ethyl ester, aceturate, besylate, edetate, phenpropionate, acetate, pamoate, and esters which serve as "prodrug" formulations which will hydrolyze in the body at physiological pH's to regenerate the acid, including pivaloylates, e.g. pivoxetil and pivoxil, and Kanebo esters, and the like.

where y is 1–6, preferably 3, can contain at least one R' substituent as defined above, and can be alkyl, e.g.,

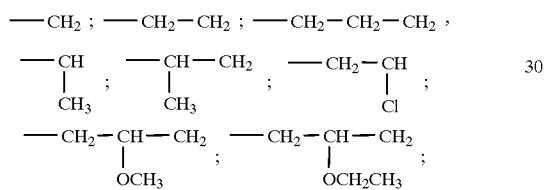

and the like.

An alkene bond can also be present in

e.g., —$CH_2$—CH=CH; —$CH_2$—CH=CH—$CH_2$; —$CH_2$—$CH_2$—CH=CH; —$(CH_2)_3$—CH=CH, and the like.

where z is 6–20, preferably 8–14, can contain at least one R" substituent as defined above, and can be alkyl; e.g.,

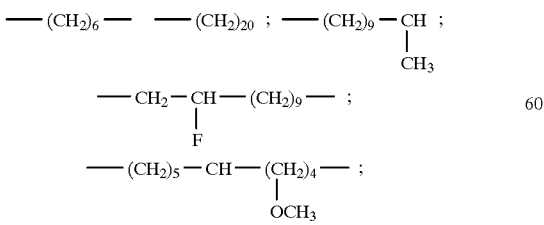

and the like.

An alkene bond can also be present in

e.g., —$CH_2$—CH=CH—$(CH_2)_8$—; —$(CH_2)_8$—CH=CH—$(CH_2)_2$—; —$(CH_2)_9$—CH=CH—$(CH_2)_9$—; $(CH_2)_4$—CH=CH—$(CH_2)_4$—; and the like.

Preferred is where one R' or R" is H and particularly preferred is where both

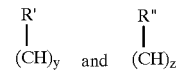

are alkyl.

Representative compounds of the instant invention within the above general formula are given by the following, structures;

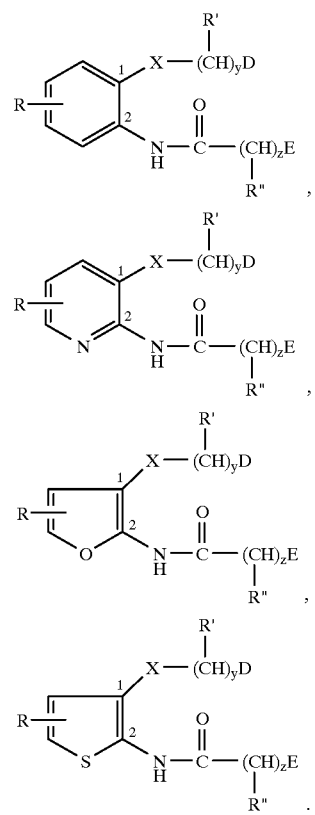

Particularly preferred are the following compounds:

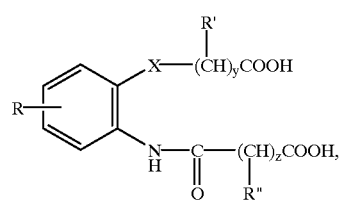

-continued
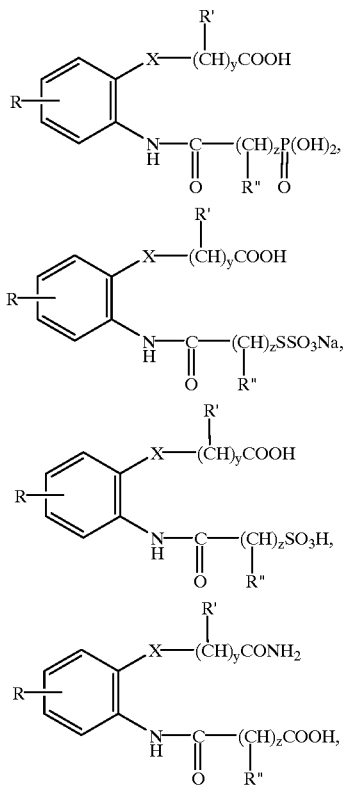
where X is O or S and R, R', R", y and z are as defined above.
Preferred compounds within this class are:
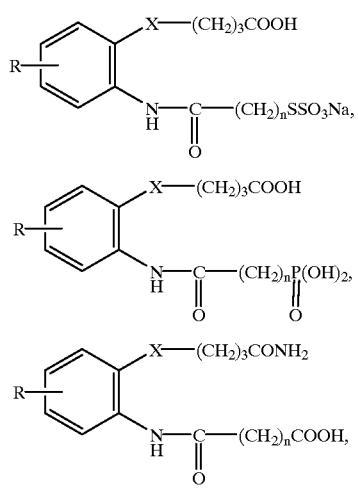
-continued
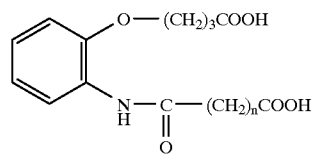
where X is O or S, and n is 8–14.
Also preferred compound are within these classes are:
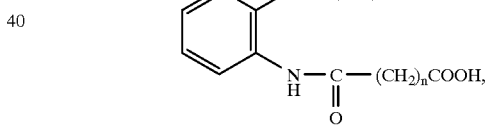
where n is 8–14.
were n is 8–14.
The compounds of the instant invention can be made by the procedures outlined in the following Flowcharts.
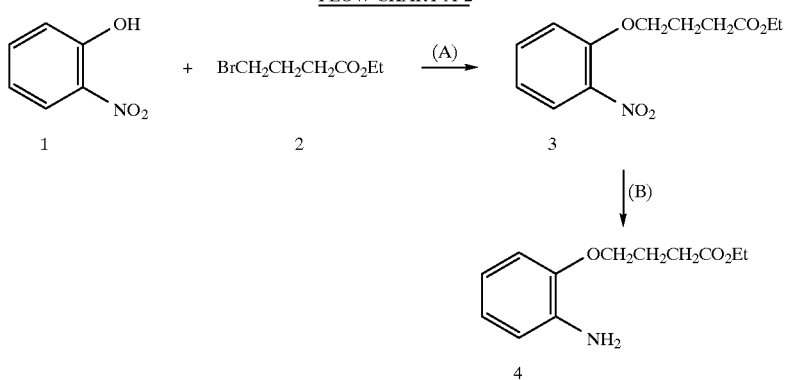
FLOW CHART A-2

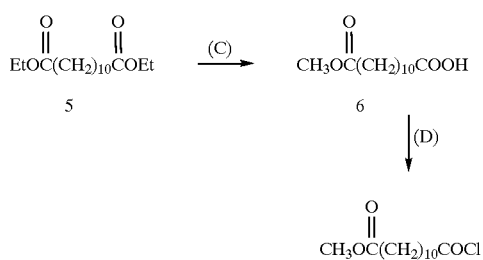
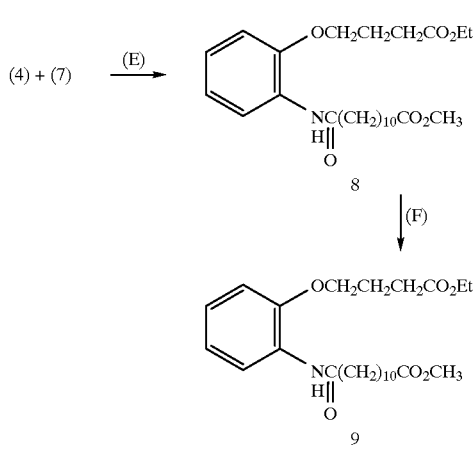
FLOW CHART B-2
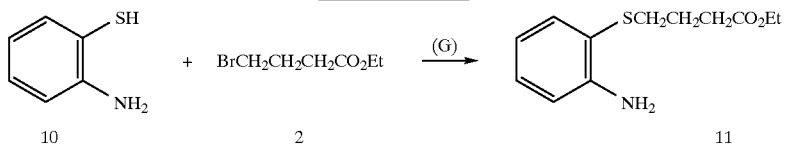
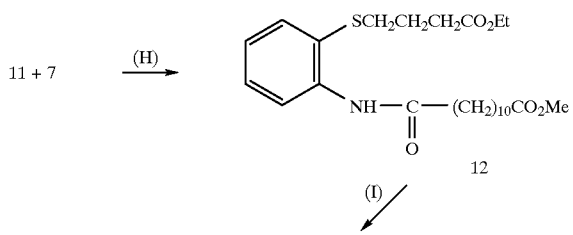
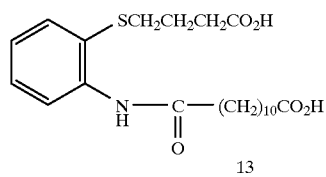
FLOW CHART B-2
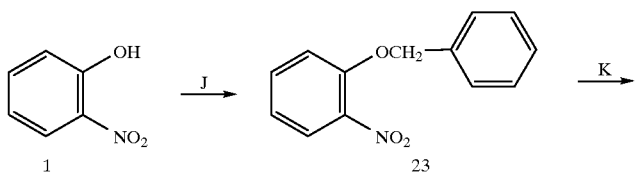

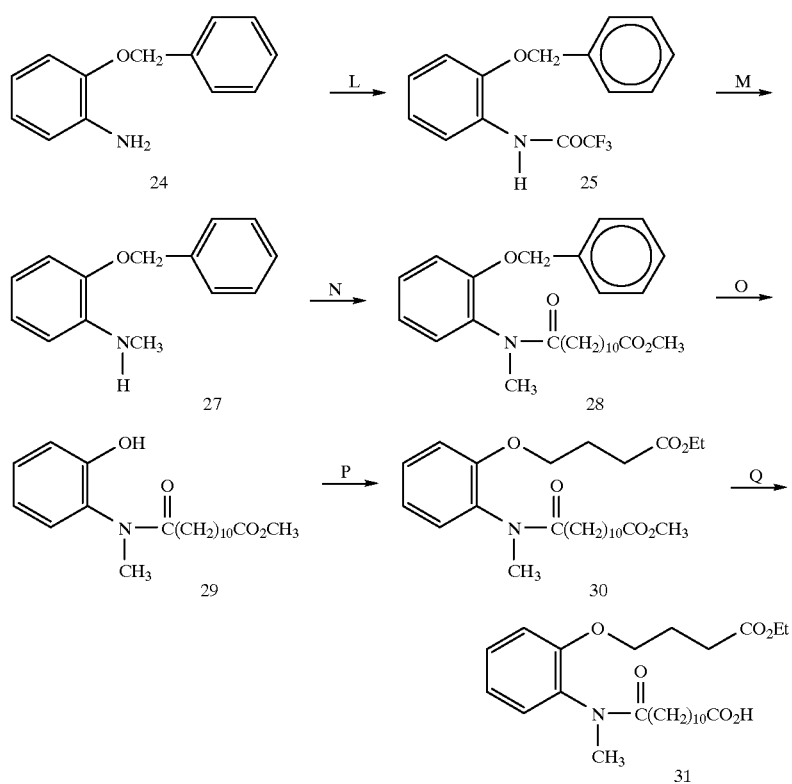
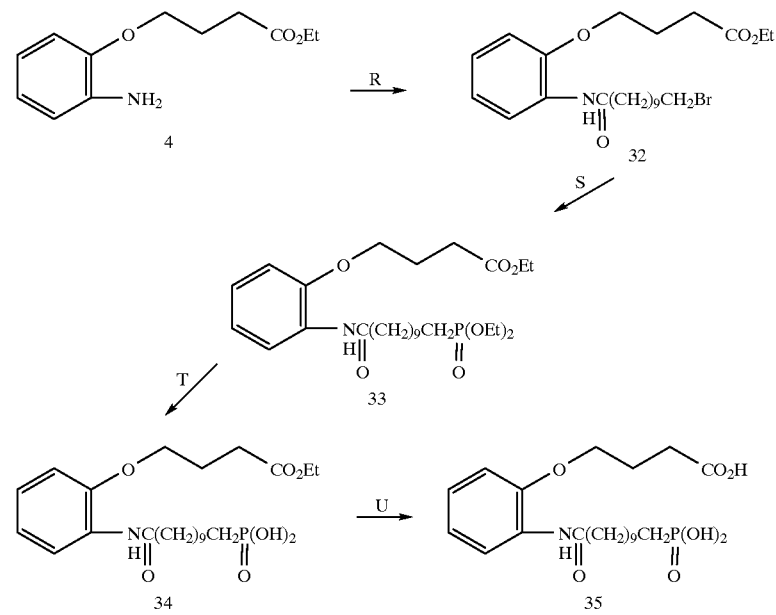
FLOW CHART E-2
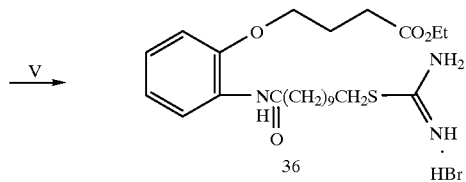

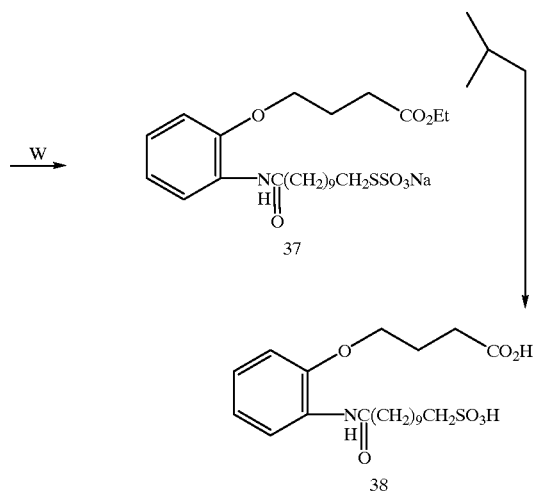

FLOW CHART F-2

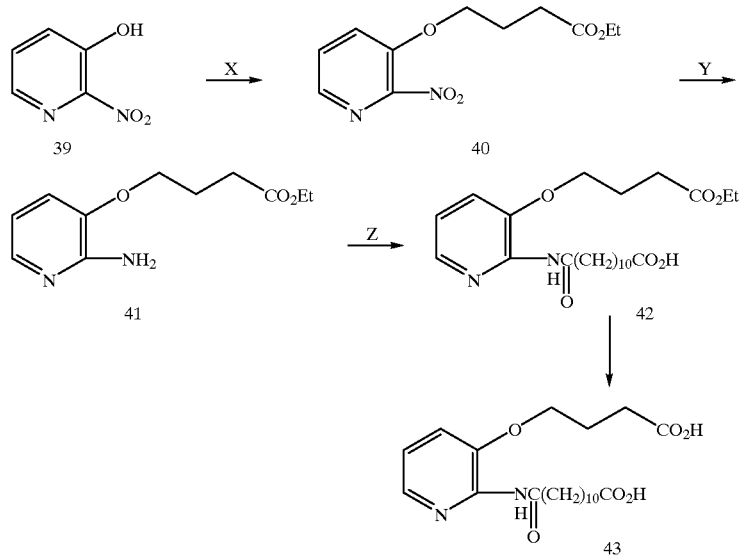

FLOW CHART G-2

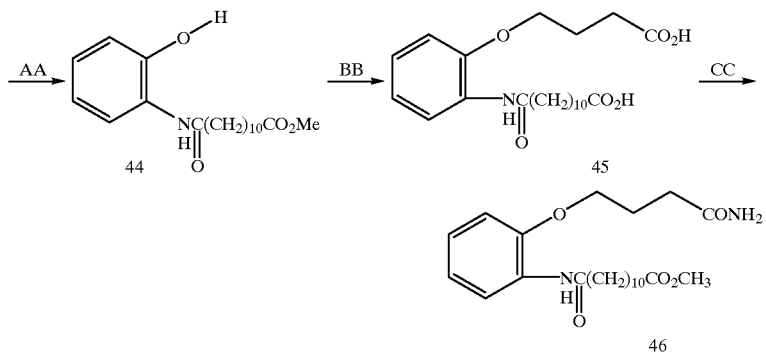

FLOW CHART H-2

As seen in Flow Chart A-2, o-nitrophenol 1, ethyl 4-bromobutyrate 2 and anhydrous $K_2CO_3$ in e.g., dry acetone are heated at reflux or stirred for an extended period of time at room temperature, under a nitrogen atmosphere to product ethyl 4-(2-nitrophenoxy) butyrate 3, in Step (A).

A solution of 3 in e.g., ethyl acetate is catalytically hydrogenated at room temperature under e.g. 40 psig of $H_2$ in the presence of a 5% Pd/C catalyst to yield ethyl 4-(2-aminophenoxy)butyrate 4 in Step (B).

Step (C) comprises reacting diethyl dodecanoate 5 with barium hydroxide octahydrate in methanol at ambient temperature to obtain the monomethyl ester 6.

In Step (D) the mono ester mono acid 6 is refluxed with thionyl chloride for about 5 hours to produce the mono acid chloride, mono methyl ester 7.

Step (E) comprises the reaction of the mono acid chloride 7 with the amine 4 at e.g., 0–10° C. in e.g., dry ether in the presence of a hydrogen acceptor e.g., triethylamine, to produce the amide 8.

In Step (F), the ether-amide diester 8 is de-esterified by e.g., 2.5 N NaOH in MeOH/H$_2$O to yield after acidification the final product, diacid 9.

Flow Chart B-2 illustrates the synthesis of the corresponding thio compounds.

Step (G) illustrates the reaction of o-aminobenzenethiol with ethyl 4-bromobutyrate which can be carried out in e.g., dry dimethoxyethane, under dry N$_2$, in the presence of a proton acceptor, e.g., dry powdered K$_2$CO$_3$, to produce 11.

Step (H) illustrates the acylation of the amino group of 11 with ethyl 11-bromoundecanoate in a dry solvent, e.g., dry ether, at 0° C. in the presence of an acid acceptor, e.g., pyridine.

Step (I) illustrates the hydrolysis of the diester to the final diacid 13, which can be accomplished with, e.g., NaOH/MeOH.

As seen in Flow Chart C-2, o-nitrophenol is benzylated under the same conditions as in Step (A).

Step (K) shows the reduction of the nitro group using e.g., Raney Ni in ethanol/NH$_3$ under 40 psig H$_2$.

Step (L) shows the trifluoroacetylation of 24 using e.g., trifluoroacetic anhydride in dry ether and powdered dry sodium carbonate.

Step (M) shows the N-methylation which can be accomplished using, e.g., methyl iodide in dry acetone and dry powdered KOH followed by removal of the N-trifluoroacetyl group with MeOH/H$_2$O.

Step (N) shows the N-acylation of 27, using an acid chloride, e.g., 7, in e.g., dry methylene chloride and pyridine at 0° C.

Step (O) shows the debenzylation of 28, which can be accomplished by e.g., 10% Pd/C in MeOH under a H$_2$ atmosphere.

Step (P) shows the O-alkylation of 29 using e.g., ethyl 4-bromobutyrate and K$_2$CO$_3$ in anhydrous acetone.

Step (Q) shows hydrolysis of the diester 30 to the diacid 31 by hydrolysis as e.g., described for Step (F).

Flow Chart D-2 shows the production of phosphonate type esters and acids.

Step (R) shows the condensation of 4 with 11-bromoundecanoic acid in anhydrous methylene chloride using N,N'-dicyclohexylcarbodiimide and 4-dimethylaminopyridine to produce the important bromo intermediate 32.

Step (S) shows the reaction of 32 with triethylphosphite at e.g., 180° C. under N$_2$ to produce the phosphonate ester 33.

Step (T) converts 33 via bromotrimethylsilane to the monoacid 34.

Step (U) uses the similar hydrolysis conditions of Step (F) to produce the phosphoniccarboxylic diacid 35.

The corresponding phosphinic acids can be analogously made from 32 by known procedures in the art.

Flow Chart E-2 illustrates the synthesis of the sulfonic acid types of the invention compounds.

Step (V) shows reaction of the intermediate 32 with thiourea in EtOH/H$_2$O under N$_2$ at 90° C. to yield the isothiouronium salt 36.

Step (W) shows the reaction of 32 with sodium thiosulfate under the conditions of Step (V) to yield the thiosulfate ester 37.

Further oxidation of esters 36 or 37 via the Showell or Ziegler procedures described in Step W in the examples yields the corresponding sulfonic acid 38.

The corresponding sulfinic acid can be prepared from 36 by the procedure of J. M. Sprague and T. B. Johnson, JACS 59, 2440 (1937).

The corresponding sulfonamide can be produced from the sulfonic acid 38, by protecting, e.g., the carboxylic acid via an ester, converting the sulfonic acid to a sulfonyl chloride, treating the sulfonyl chloride with ammonia and then hydrolyzing the protected carboxylic ester to the corresponding acid.

Flow Chart F-2 shows the corresponding synthesis of the pyridine analogs of 8 and 9.

In Step (X), the nitrohydroxy pyridine is O-alkylated first using conditions analogous to Step (A) to produce 40.

Step (Y) shows reducing the nitro group in the same manner as described for Step (B).

Step (Z) shows acylating the amino group in the same manner as described for 8 in Step (E) to produce the diester 42. Hydrolysis produces the diacid 43.

Flow Chart G-2 shows the production of some amides 46 of the invention.

In Step (AA), o-aminophenol is reacted directly with 7 under the conditions of Step (E) to produce the N-acylated phenol 44.

In Step (BB), O-alkylation of 44 as carried out using 4-bromobutyronitrile under conditions similar to Step (A), produces 45.

Step (CC) shows the hydrolysis of the nitrile to the amide 46 using MnO$_2$ in methylene chloride.

Flow Chart H-2 illustrates an alternate route to 9 by starting with o-aminophenol, acylating to produce 44, then reacting 44 under the conditions of Step (A) to produce 8, then hydrolysis using Step (F) to yield 9.

Thus, by using the above described methods in the Flow Charts and the reaction starting materials and reagents described herein, all of the compounds described and encompassed by the claim can be synthesized by one skilled in the art.

It is obvious that other nitrophenols can be substituted for 1 in Flow Charts A-2 and C-2 to provide the scope of the compounds covered by this invention and include the following:
2-nitrophenol
2-nitro-6-methylphenol
2-nitro-5-methylphenol
2-nitro-4-methylphenol
2-nitro-3-methylphenol
2-nitro-4-phenylphenol
2-nitro-5-phenylphenol
2-nitro-4-chlorophenol
2-nitro-4-fluorophenol
2-nitro-4-trifluoromethylphenol
2-nitro-4-hydroxyphenol
2-nitro-4-methoxyphenol
2-nitro-6-ethoxyphenol
2-nitro-4-methylthio-phenol
2-nitro-4-methylsulfinylphenol
2-nitro-4-methylsulfonylphenol
4-nitro-3-hydroxypyridine
3-nitro-4-hydroxy-5-methylpyridine
3-nitro-4-hydroxy-6-methylpyridine
2-methyl-3-nitro-4-hydroxypyridine 2-hydroxy-3-nitro-5-phenylpyridine
2-nitro-3-hydroxy-5-phenylpyridine
2-hydroxy-3-nitro-5-chloropyridine
2-nitro-3-hydroxy-5-trifluoromethylpyridine
2-methoxy-4-nitro-5-hydroxypyridine
3-nitro-4-hydroxy-5-ethoxypyridine
2-methylthio-4-nitro-5-hydroxypyridine
2-nitro-3-hydroxy-thiophene
3-nitro-4-hydroxy-thiophene
3-hydroxy-2-nitro-5-methyl-thiophene
3-hydroxy-2-nitro-4-methyl-thiophene
2-hydroxy-3-nitro-5-phenyl-thiophene
2-nitro-3-hydroxy-4-phenyl-thiophene
2-hydroxy-3-nitro-4-chlorothiophene
2-hydroxy-3-nitro-4-fluorothiophene
and the like.

It is obvious that suitable replacement compounds for 2 with other halo alkyl esters, known in the art, and that suitable replacement of 6 with other diesters, available in the art, will yield all of the ether-amide derivatives within the scope of the claims.

Representative examples of 2 useful in the invention process include, but are not limited to:

Br—$CH_2$—COOMe,
Cl—$CH_2CH_2CH_2$COOCH($CH_3$)$_3$,
Br—$CH_2CH_2CH_2CH_2$COOMe,
Br—$CH_2CH_2CH_2CH_2CH_2$COOEt,
Br—$CH_2CH_2CH_2CH_2CH_2CH_2$COOCH$_2$CH$_2$CH$_3$,
Br—$CH_2$CH($CH_3$)COOMe,
Br—$CH_2$CH($CH_3$)$CH_2$COOEt,
Br—$CH_2CH_2CH_2$COOMe,
Br—$CH_2$CH($OCH_3$)$CH_2$COOCH($CH_3$)$_2$,
Cl—$CH_2$CH($OCH_2CH_3$)$CH_2$COOMe,
Br—$CH_2$CH(F)$CH_2$COOMe,
and the like.

Representative examples of other compounds substitutable for 6 and useful in the invention are:

HOOC($CH_2$)$_6$COOMe,
HOOC($CH_2$)$_7$COOMe,
HOOC($CH_2$)$_8$COOMe,
HOOC($CH_2$)$_9$COOMe,
HOOC($CH_2$)$_{10}$COOMe,
HOOC($CH_2$)$_{11}$COOMe,
HOOC($CH_2$)$_{12}$COOEt,
HOOC($CH_2$)$_{13}$COOCH($CH_3$)$_2$,
HOOC($CH_2$)$_{14}$COOCHCH$_2$CH$_3$,
HOOC($CH_2$)$_{15}$COO($CH_2$)$_3$CH$_3$,
HOOC($CH_2$)$_{16}$COOCH$_3$,
HOOC($CH_2$)$_{17}$COOCH$_3$,
HOOC($CH_2$)$_{18}$COOMe,
HOOC($CH_2$)$_{19}$COOEt,
HOOC($CH_2$)$_{20}$COOPh,
HOOC($CH_2$)$_{10}$COOCH$_2$Ph,
HOOCCH($CH_3$)—($CH_2$)$_{10}$COOMe,
HOOC—$CH_2$CH—($CH_3$)($CH_2$)$_{10}$COOMe,
HOOC—$CH_2CH_3$CH($CH_3$)$CH_2$COOEt,

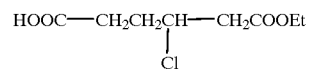

HOOC—$CH_2$CH($OCH_3$)($CH_2$)$_7$COOCH($CH_3$)$_2$,
where Ph is phenyl,
and the like.

Representative examples of compounds produced by this process include those in the following list.

The nomenclature used herein for the acid radicals is:
$P(O)(OH)_2$, phosphono;
—COOH, carboxy;
—$CONH_2$, aminocarbonyl;
—$SO_3H$, sulfo;
—$SO_2H$, sulfino;
—$SSO_3H$, thiosulfato, as the sodium salt.

4-(2-(20-Carboxyeicosanoylamino)phenoxy)butyric acid;
4-(2-(19-Carboxynonadecanoylamino)phenoxy)butyric acid;
4-(2-(18-Carboxyoctadecanoylamino)phenoxy)butyric acid;
4-(2-(17-Carboxyheptadecanoylamino)phenoxy)butyric acid;
4-(2-(16-Carboxyhexadecanoyl-N-methylamino)phenoxy)-butyric acid;
4-(2-(15-Carboxypentadecanoylamino)phenoxy)butyramide;
4-(2-(14-Carboxytetradecanoylamino)phenoxy)butyric acid;
4-(2-(13-Carboxyl-tridecanoylamino)phenoxy)butyric acid;
4-(2-(12-Carboxy-dodecanoylamino)phenoxy)butyric acid;
4-(2-(11-Carboxy-undecanoylamino)phenoxy)butyric acid;
4-(2-(10-Carboxy-decanoylamino)phenoxy)butyric acid;
4-(2-(9-Carboxy-nonanoylamino)phenoxy)butyric acid;
4-(2-(8-Carboxyoctanoylamino)phenoxy)butyric acid;
4-(2-(7-Carboxyheptanoylamino)phenoxy)butyric acid;
4-(2-(6-Carboxyhexanoylamino)butyric acid;
4-(2-(20-Carboxyeicosanoylamino)phenylthio)butyric acid;
4-(2-(19-Carboxynonadecanoylamino)phenylthio)butyric acid;
4-(2-(18-Carboxyoctadecanoylamino)phenylthio)butyric acid;
4-(2-(17-Carboxyheptadecanoyl-N-ethylamino)phenylthio)butyric acid;
4-(2-(16-Carboxyhexadecanoylamino)phenylthio)butyric acid;
4-(2-(15-Carboxypentadecanoylamino)phenylthio)butyric acid;
4-(2-(14-Carboxytetradecanoylamino)phenylthio)butyramide;
4-(2-(13-Carboxytridecanoylamino)phenylthio acid;
4-(2-(12-Carboxy-dodecanoylamino)phenylthio)butyric acid;
4-(2-(11-Carboxy-undecanoylamino)phenylthio)butyric acid;
4-(2-(10-Carboxydecanoylamino)phenylthio)butyric acid;
4-(2-(9-Carboxynonanoylamino)phenylthio)butyric acid;
4-(2-(8-Carboxyoctanoylamino)phenylthio)butyric acid;
4-(2-(7-Carboxyheptanoylamino)phenylthio)butyric acid;
4-(2-(6-Carboxyhexanoylamino)phenylthio)butyric acid;
3-(2-(16-Carboxyhexadecanoylamino)phenoxy)propionic acid;
4-(2-(15-Carboxyisohexadecanoylamino)phenoxy)butyric acid;

4-(2-(14-Carboxytetradecanoylamino)phenoxy)butyric acid;
5-(2-(13-Carboxytridecanoylamino)phenoxy)valeric acid;
5-(2-(12-Carboxydodecanoylamino)phenoxy)valeric acid;
5-(2-(11-Carboxyisododecanoylamino)valeric acid;
4-(2-(11-Carboxyundecanoylamino)isovaleric acid;
4-(2-(10-Carboxydecanoylamino)isovaleric acid;
5-(2-(9-Carboxynonanoylamino)phenoxy)valeric acid;
6-(2-(9-Carboxynpnanoylamino)phenoxy)caproic acid;
6-(2-(8-Carboxyoctanoylamino)phenoxy)caproic acid;
6-(2-(7-Carboxyisooctanoylamino)phenoxy)caproic acid;
7-(2-(7-Carboxyheptanoylamino)phenoxy)enanthic acid;
7-(2-(6-Carboxyhexanoylamino)phenoxy)enanthic acid;
7-(2-(5-Carboxyisohexanoylamino)phenoxy)enanthic acid;
2-(2-(12-Carboxydodecanoylamino)phenoxy)acetic acid;
2-(2-(11-Carboxyundecanoylamino)phenoxy)acetic acid;
2-(2-(10-Carboxydecanoylamino)phenoxy)acetic acid;
3-(2-(9-Carboxynonanoylamino)phenoxy)propionic acid;
3-(2-(12-Carboxydodecanoylamino)phenylthio)propionic acid;
3-(2-(11-Carboxyundecanoylamino)phenylthio)propionic acid;
3-(2-(11-Carboxyundecanoylamino)phenylthio)isobutyric acid;
4-(2-(19-Carboxynonadecanoyl-N-methylamino)phenylthio)butanesulfonic acid;
4-(2-(18-Carboxyoctadecanoylamino)phenylthio)butanesulfonic acid;
4-(2-(17-Carboxyheptadecanoylamino)phenylthio)butanesulfinic acid;
4-(2-(16-Carboxyhexadecanoylamino)phenylthio)butanethiosulfonic acid, sodium salt;
4-(2-(14-Carboxytetradecanoyl N-propylamino)phenylthio)butanephosphonic acid;
4-(2-(13-Carboxytridecanoylamino)phenylthio)butanesulfonic acid;
4-(2-(12-Carboxydodecanoylamino)phenylthio)butanesulfinic acid;
4-(2-(11-Carboxyundecanoylamino)phenylthio)butanethiosulfonic acid, sodium salt;
4-(2-(9-Carboxynonanoylamino)phenylthio)butanephosphonic acid;
4-(2-(8-Carboxyoctanoylamino)phenylthio)butanesulfonic acid;
4-(2-(7-Carboxyheptanoylamino)phenylthio)butanesulfinic acid;
4-(2-(6-Carboxyhexanoylamino)phenylthio)butanethiosulfonic acid, sodium salt;
3-(2-(15-Carboxyisohexadecanoylamino)phenoxy)isobutanephosphonic acid;
3-(2-(14-Carboxytetradecanoylamino)phenoxy)isobutanoic acid;
5-(2-(13-Carboxytridecanoylamino)phenoxy)pentanesulfinic acid;
5-(2-(12-Phosphonododecanoylamino)phenoxy)valeramide;
5-(2-(11-Sulfoundecanoylamino)valeric acid;
5-(2-(10-Sulfinodecanoyl N-methylamino)phenoxy valeric acid;
5-(2-(9-Thiosulfatononanoylamino)phenoxy)valeric acid, sodium salt;
6-(2-(9-Phosphonononanoylamino)phenoxy)caproic acid;
6-(2-(7-Sulfoisooctanoyl-N-methylamino)phenoxy)caproic acid;
7-(2-(7-Sulfinoheptanoyl-N-ethylamino)phenoxy)enanthic acid;
7-(2-(6-Thiosulfatohexanoylamino)phenoxy)enanthamide, sodium salt;
7-(2-(5-Phosphonoisohexanoylamino)phenoxy)enanthic acid;
2-(2-(11-Sulfoundecanoylamino)phenoxy)acetic acid;
2-(2-(10-Sulfodecanoyl-N-propylamino)phenoxy)acetic acid;
3-(2-(9-Sulfinononanoylamino)phenoxy)propionic acid;
3-(2-(12-Thiosulfatododecanoylamino)phenylthio)propionamide, sodium salt;
3-(2-(11-Phosphonoundecanoylamino)phenylthio)propionic acid;
3-(2-(11-Sulfoundecanoylamino)-4-methyl-phenylthio)isobutyric acid;
3-(2-(12-Sulfinododecanoylamino)phenylthio)isobutyramide;
5-(2-(11-Thiosulfoundecanoyl-N-butylamino)phenylthio)valeric acid, sodium salt;
5-(2-(10-Phosphonodecanoylamino)phenylthio)valeric acid;
5-(2-(12-Phosphonododecanoylamino)phenylthio)pentanesulfonic acid;
5-(2-(11-Carboxydecanoylamino)phenylthio)pentane sulfinic acid;
5-(2-(10-Phosphonodecanoylamino)phenylthio)pentanethiosulfonic acid;
6-(2-(12-Phosphonododecanoylamino)phenylthio)hexanephosphonic acid;
4-(2-(11-Sulfinoundecanoylamino)4-methyl-phenoxy)butane-thiosulfonic acid, sodium salt;
4-(2-(12-Sulfododecanoylamino)6-methylphenoxy)butane sulfonic acid;
4-(2-(11-Sulfodecanoylamino)3-chloro)phenylthio)-butanesulfinic acid;
4-(2-(10-Sulfodecanoylamino)4-methylphenoxy)butanethiosulfonic acid, sodium salt;
4-(2-(12-Sulfododecanoylamino)6-methylphenoxy)-butanephosphonic acid;
5-(2-(11-Sulfinoundecanoylamino)-3-methylphenylthio)pentane-sulfonic acid;
4-(2-(11-Sulfinoundecanoylamino)-3-methylsulfonylphenoxy)butane-sulfinic acid;
4-(2-(11-Sulfinoundecanoylamino)-4-methylsulfonyl)phenylthio)butanesulfonic acid;
4-(2-(12-Sulfinododecanoylamino)5-ethyl-phenoxy)-butane-phosphonic acid;
4-(2-(10-Sulfinodecanoylamino)-3,5-dimethylphenoxy)-butane-sulfonic acid;
4-(2-(9-Thiosulfatononanoylamino)-4-fluoro-phenoxy)butane-sulfinic acid, sodium salt;
4-(2-(12-Thiosulfatododecanoylamino)-5-trifluromethylphenyl)butane-thiosulfonic acid, sodium salt;
4-(2-(10-Thiosulfatodecanoylamino)-4-hydroxyphenylthio)butane-phosphbnic acid, sodium salt;
4-(2-(9-Phosphonononanoylamino)-3,5-dimethoxyphenylthio)butyric acid;
5-(2-(11-Sulfoundecanoylamino)-4-nitrophenoxy)-valeric acid;
4-(2-(11-Sulfinoundecanoylamino)-5-amino-3-methylphenoxy)butyric acid;
4-(2-(11-Thiosulfatoundecanoylamino)-5-amino-4-methylphenylthio)butyric acid, sodium salt;
4-(2-(12-Phosphonododecanoylamino)-4-dimethylaminophenoxy)butyric acid;
4-(2-(10-Sulfodecanoylamino)-phenoxy)butyric acid;
3-(2-(9-Sulfinononanoylamino)phenoxy)propionic acid;
3-(2-(12-Thiosulfatododecanoylamino)phenoxy)-3-methylpropionic acid, sodium salt;

3-(2-(11-Phosphonodecanoylamino)thienyloxy)-2-chloropropionic acid;
4-(2-(9-Sulfononanoylamino)thienyloxy-3-ethoxybutyric acid;
4-(2-(12-Sulfinododecanoylamino)phenoxy)-2-fluorobutyric acid;
7-(2-(11-Thiosulfatoundecanoylamino)phenoxy)6-aminoenanthic acid, sodium salt;
5-(2-(11-Phosphonoundecanoylamino)-3-methylphenoxy)-4-oxo-valeric acid;
4-(2-(12-Sulfododecanoylamino)phenoxy)but-2-enoic acid;
4-(2-(11-Sulfinodecanoylamino)phenoxy)but-2-enoic acid;
4-(2-(10-Thiosulfatodecanoylamino)phenoxy)-4-methylene valeric acid, sodium salt;
4-(2-(9-Phosphonononanoylamino)phenoxy)-4-fluoro-2-butenoic acid;
4-(2-(11-Sulfo-3-methylbutanoylamino)thienyloxy)-butyric acid;
4-(2-(4-Sulfino-3-chlorobutanoylamino)thienyloxy)-butyric acid;
4-(2-(9-Thiosulfato-2-methoxynonanoylamino)thienyloxy) butyric acid, sodium salt;
4-(2-(4-Phosphono-2-ethoxybutanoylamino)phenoxy) butyric acid;
4-(2-(14-Sulfo-14-fluoro-2-acetamidotetradecanoylamino)-3-methylphenoxy)butyric acid;
4-(2-13-Sulfino-2-oxotridecanoylamino)-4-methylthio)-phenyloxy)butyric acid;
4-(2-(12-Thiosulfatododecanoyl-3-en-amino)phenoxy) butyric acid;
4-(2-(11-Phosphonoundecanoyl-7-ene-amino)phenoxy) butyric acid;
4-(2-(4-Sulfo-2-fluoro-2-butenoylamino)phenoxy)-butyric acid;
4-(2-(12-Sulfinododecanoylamino)-4-methyl-3-pyridyloxy) butyric acid;
4-(2-(11-Thiosulfatoundecanoylamino)-4-methyl-3-pyridyloxy)butyric acid;
4-(2-(10-Phosphonodecanoylamino)-5-methyl-3-pyridyloxy)butyric acid;
4-(2-(11-Sulfinodecanoylamino)-4-nitro-3-pyridylthiobutyric acid;
4-(2-(10-Thiosulfatodecanoylamino)-6-methylsulfonyl-3-pyridyloxy)butyric acid, sodium salt;
4-(2-(9-Phosphonononanoylamino)5-chloro-3-pyridylthio) butyric acid;
4-(2-(11-Sulfoundecanoylamino)5-methylsulfonyl-3-pyridylthio)butyric acid;
4-(2-(11-Sulfinoundecanoylamino)-6-methyl-3-pyridylthio) butyric acid;
4-(2-(11-Thiosulfatoundecanoylamino)-4,6-dimethyl-3-pyridyloxy)butyric acid, sodium salt;
4-(2-(12-Phosphonododecanoylamino)-5-(methylthio)-3-pyridyloxy)butyric acid;
4-(2-(10-Sulfodecanoylamino)-5-methoxy-3-pyridyloxy) butyric acid;
4-(2-(9-Sulfinononanoylamino)-4-fluoro-6-methyl-3-pyridyloxy)butyric acid;
4-(2-(12-Thiosulfatododecanoylamino)5-(methylamino)-3-pyridyloxy)butyric acid, sodium salt;
4-(2-(11-Phosphonoundecanoylamino)4-phenyl-3-pyridylthio)butyric acid;
4-(2-(9-Sulfounonanoylamino)6-methoxy-3-pyridylthio) butyric acid;
4-(2-(12-Sulfinododecanoylamino)-6-trifluoromethyl-3-pyridyloxy)butyric acid;
5-(2-(11-Thiosulfatoundecanoylamino)-4-methyl-3-thiophenyloxy)valeric acid, sodium salt;
4-(2-(11-Phosphonoundecanoylamino)-4-methyl-3-thiophenyloxy)butyric acid;
4-(2-(12-Sulfododecanoylamino)-5-methyl-3-thiophenylthio)butyric acid;
4-2(-(11-Sulfinoundecanoylamino)-4-methyl-3-thiophenylthio)butyric acid;
4-(2-(10-Thiosulfatodecanoylamino)-5-methyl-3-thienylthio)butyric acid, sodium salt;
4-(2-(9-Phosphonononanoylamino)-4-hydroxy-3-thienyloxy)butyric acid:
4-(2-(11-Sulfodecanoylamino)-4-methylthio-3-thienyloxy) butyric acid;
4-(2-(10-Sulfinodecanoylamino)-4-methylsulfonyl-3-thienyloxy)butyric acid;
4-(2-(9-Thiosulfatononanoylamino)-4-methylsulfonyl-3-thienyloxy)butryic acid, sodium salt;
4-(2-(12-Phosphonododecanoylamino)-5-trifluoromethyl-3-thienyloxy)butyric acid;
4-(2-(11-Sulfoundecanoylamino)-4-methyl-5-phenyl-3-thienyloxy)butyric acid;
4-(2-(11-Sulfinoundecanoylamino)-5-methylamino-3-thienyloxy)butyric acid;
4-(2-(12-Thiosulfatododecanoylamino)-5-dimethylamino-3-thienyloxy)butyric acid, sodium salt;
4-(2-(11-Phosphonoundecanoylamino)-4-amino-3-thienyloxy)butyric acid;

Preferred compounds in the invention include:
4-(2-(11-Carboxyundecanoylamino)phenoxy)butyric acid,
4-(2-(11-Carboxyundecanoylamino)phenylthio)butyric acid,
4-(2-(9-Carboxynonanoylamino)phenoxy)butyric acid,
4-(2-(10-Carboxydecanoylamino)phenoxy)butyric acid,
4-(2-(12-Carboxydodecanoylamino)phenoxy)butyric acid,
4-(2-(13-Carboxytridecanoylamino)phenoxy)butyric acid,
4-(2-(15-Carboxypentadecanoylamino)phenoxy)butyric acid,
4-(2-(11-Carboxyundecanoylamino)-4-methylphenoxy)-butyric acid,
4-(2-(11-Carboxyundecanoylamino)-5-methylphenoxy)-butyric acid.

Also included as a 5α-reductase inhibitor in this invention is an agent of the following formula:

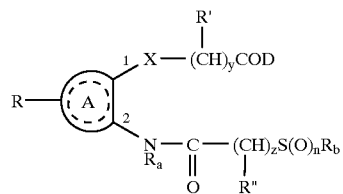

wherein
A is an 1,2-disubstituted aromatic ring, preferably a benzene ring;
D is OH, $NH_2$, $NHR_c$, $OR_c$;
X is O, S, SO, or $SO_2$;
R is H,
$C_1$–$C_4$ alkyl,
phenyl or substituted phenyl,
halo,
haloalkyl,
hydroxy,
carboxy,
cyano,
$C_1$–$C_4$ alkoxy,
$C_1$–$C_4$ alkylthio, C$_1$–C$_4$ alkylsulfinyl,
C$_1$–C$_4$ alkylsulfonyl,
nitro,
amino,
C$_1$–C$_4$ mono or di-alkylamino;
R' and R" are independently
  H,
  halo,
  C$_1$–C$_4$ alkyl or C$_1$–C$_4$ alkoxy,
  amino, or oxo, where CH—R' or CH—R" in the formula become —C=O;
R$_a$ is H, C$_1$–C$_4$ alkyl;
R$_b$, R$_c$ are independently, C$_1$–C$_{12}$ alkyl, phenyl, phenyl-C$_1$–C$_4$ alkyl;
n is 0–2;
y is 1–6;
z is 6–20; and
wherein

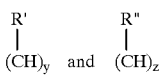

can independently represent substituted or unsubstituted alkyl radicals or alkenyl radicals containing at least one alkene bond;
and pharmaceutically acceptable salts and esters thereof.

The compounds of the instant invention are inhibitors of the human testosterone 5α-reductase.

The scope of the compounds of the instant invention are described by the above-described formula.

In the description of the formula the following terms are used which are hereby defined:

X can be O or S, preferably one X being O, and particularly preferred wherein both Xs are O, i.e., the catechol structure.

"C$_1$–C$_4$ alkyl" includes linear or branched species, e.g. methyl, ethyl, n-propyl, isopropyl, cyclopropyl, n-butyl, isobutyl, sec-butyl, t-butyl; and "C$_1$–C$_{12}$ alkyl" includes alkyl up to 12 carbons including n-octyl, t-decyl, n-dodecyl.

"Phenyl C1–C4 alkyl" includes benzyl, 2-phenethyl, and the like;

"C$_1$–C$_4$ alkoxy" includes linear or branched species, e.g., methoxy, ethoxy, n-propoxy, isopropoxy, n-butoxy, isobutoxy, sec-butoxy, t-butoxy;

"Halo" includes fluoro, chloro, bromo or iodo;

"Substituted phenyl" includes phenyl substituted by one or more of C$_1$–C$_4$ alkyl, C$_1$–C$_4$ alkoxy, or halo, and the like, as defined above; representative examples include o, m-, p-methoxy phenyl; 2,4-dimethoxyphenyl; 2-chloro-4-ethoxyphenyl; 3,5-dimethoxyphenyl; 2,4-dichlorophenyl; 2-bromo-4-methylphenyl, o-fluorophenyl, and the like.

"Haloalkyl" includes C$_1$–C$_4$ alkyl, defined above, substituted with one or more "halo" as defined above and includes: trifluoromethyl, 2,2-dichloroethyl and the like.

"C$_1$–C$_4$ alkylthio" includes C$_1$–C$_4$ alkyl, defined above, substituted with at least one divalent thio (—S—) grouping including; methylthio, ethylthio, isopropylthio, n-butylthio, and the like.

"C$_1$–C$_4$ alkylsulfinyl" includes C$_1$–C$_4$ alkyl, defined above, substituted with at least one —SO— grouping including; methylsulfinyl, ethylsulfinyl; isopropylsulfinyl, and the like.

"C$_1$–C$_4$ alkylsulfonyl" includes C$_1$–C$_4$ alkyl, defined above, substituted with at least one sulfonyl group, —SO$_2$—, including; methylsulfonyl, ethylsulfonyl, isopropylsulfonyl, n-butylsulfonyl, and the like;

"C$_1$–C$_4$ mono or dialkyl amino" includes amino, substituted with one or more C$_1$–C$_4$ alkyl groups as defined hereinabove, including: methylamino, ethylamino, n-butylamino, t-butylamino, dimethylamino, N,N-diethylamino, methyl-t-butylamino, and the like.

The R group or groups on the benzene ring can be present initially in the process, e.g. phenyl, methyl, methoxy, cyano, carbomethoxy, trifluoromethyl, (present as in the starting 6-nitrophenol 1 in Flow Chart A) or added later by a conventional reaction, e.g. chloro, as by chlorination, nitro by nitration, or created from a starting or added functional group present, e.g. converting a later added nitro to an amino group by catalytic reduction, then alkylating to a mono or dialkylamine. An amino group can be subjected to diazotization to a hydroxy group, which can be followed by methylation to a methoxy group. Similarly, a hydroxy group can be converted to a thiol by the analogous procedures described in J. Org. Chem. 31, pp 3980–3984 (1966) by Newman and Karnes, and J. Org. Chem. 31, pp 410 (1966) by Kwart, H. and Evans, E. S. The resulting thiol can be alkylated to alkylthio, which can be oxidized to the corresponding sulfoxide or sulfone. Preferred substituents are H, C$_1$–C$_4$ alkyl, C$_1$–C$_4$ alkoxy and phenyl. These reactions and sequences are conventional in the art and it will be obvious to one skilled in the art to modify the benzene ring to arrive at an R radical disclosed herein.

By the term "pharmaceutically acceptable salts and esters thereof" is meant salts and esters of the acid groups in the final molecule which can be used as part of the human drug delivery system and include the salts: sodium, potassium, calcium, ammonium, substituted Ammonium, quaternary ammonium, and esters: ethyl ester, aceturate, besylate, edetate, phenpropionate, acetate, pamoate, and esters which serve as "prodrug" formulations which will hydrolyze in the body at physiological pH's to regenerate the acid, including pivaloylates, e.g. pivoxetil and pivoxil, and Kanebo esters, and the like.

where y is 1–6, preferably 3, can contain at least one R' substituent as defined above, and can be, e.g.,

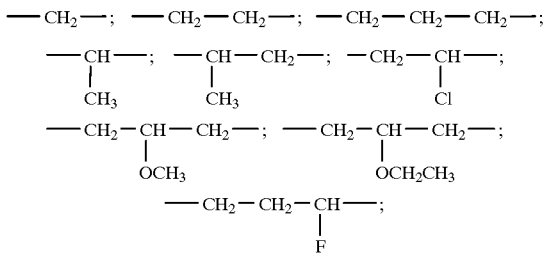

and the like.

An alkene bond can also be present in

e.g., CH$_2$—CH=CH—; CH$_2$—CH=CH—CH$_2$—; —CH$_2$—CH=CH—; —(CH$_2$)$_3$—CH=CH— and the like.

where z is 6–20, preferably 8–14, can contain at least one R" substituent as defined above, and can be completely alkyl; e.g., $(CH_2)_n$-COOH, where n is 8–14 preferably and the like.

An alkene bond can also be present in

e.g., $-(CH_2)_4-CH=CH-(CH_2)_4-$, and the like.

Preferred is where one R' or R" is H and particularly preferred is where both

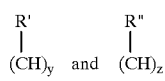

are alkyl.

Preferred compounds of the instant invention are given by the following formulas;

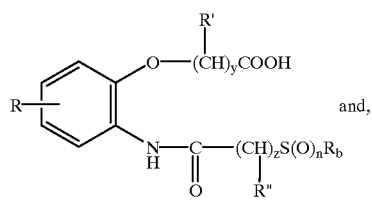

and,

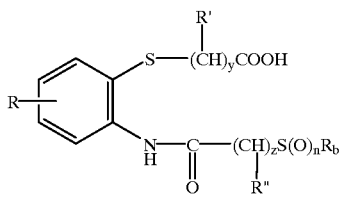

wherein R, R', R", Y, Z, $R_b$ are defined above; and particularly preferred are:

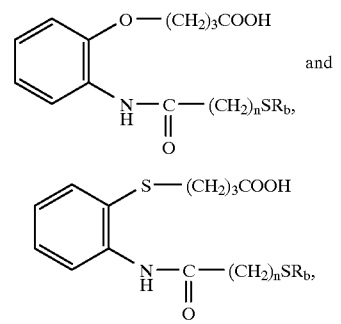

where n is 8–14, and $R_b$ is methyl, ethyl, cyclopropyl, isopropyl, n-propyl, t-butyl, phenyl or benzyl.

The compounds of the instant invention can be made by the procedures outlined in the following Flowcharts.

FLOW CHART A-3

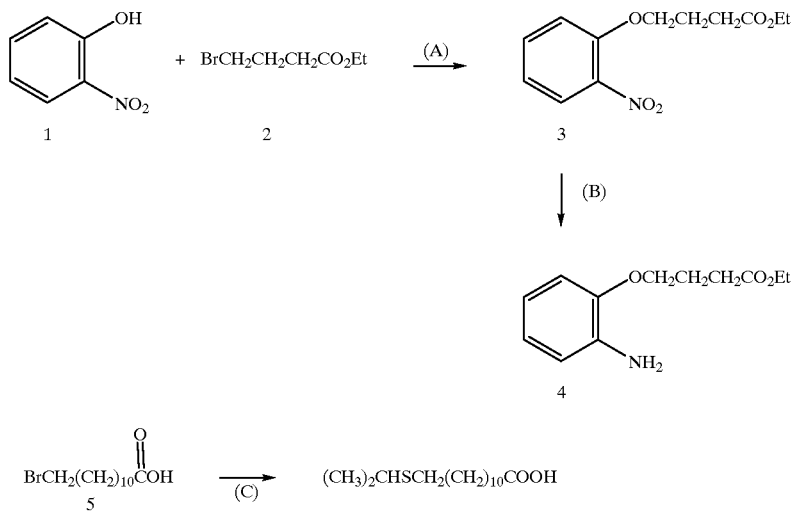

-continued
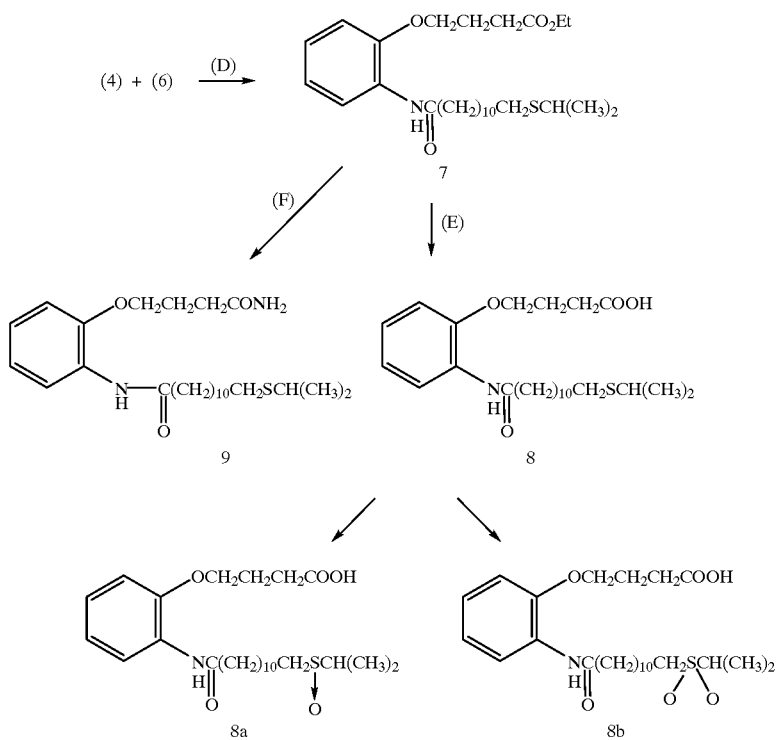
FLOW CHART B-3
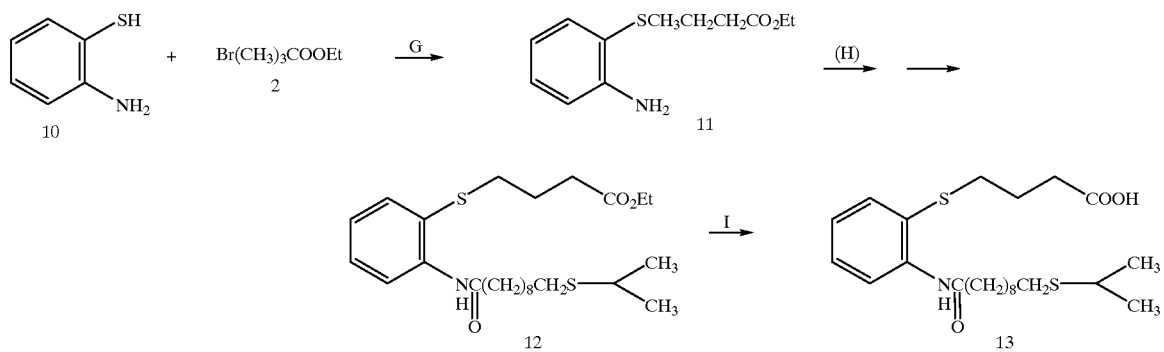
FLOW CHART C-3
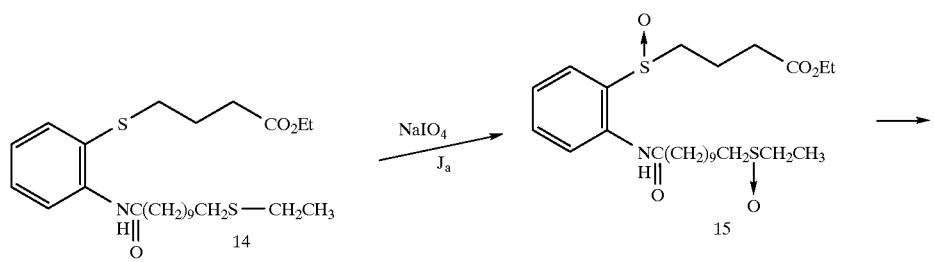

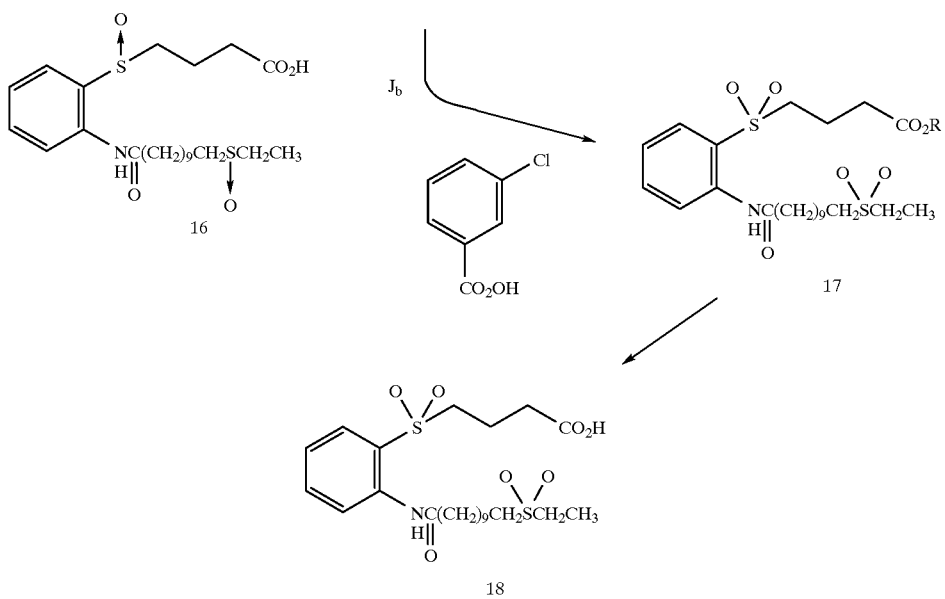

As seen in Flow Chart A-3, o-nitrophenol 1, ethyl 4-bromobutyrate 2 and anhydrous $K_2CO_3$ in e.g., dry acetone are heated at reflux e.g. for 12–100 hours, or stirred for an extended period of time at room temperature, under a nitrogen atmosphere to product ethyl 4-(2-nitrophenoxy) butyrate 3, in Step (A).

A solution of 3 in e.g., ethyl acetate is catalytically hydrogenated at room temperature under e.g. 40 psig of $H_2$ in the presence of a 5% Pd/C catalyst to yield ethyl 4-(2-aminophenoxy)butyrate 4 in Step (B).

Step (C) comprises reacting the 12-bromo dodecanoic acid 5 with isopropyl mercaptan in a suitable solvent, e.g., dimethoxyethane, at about 80–85° C. to obtain the acid 6.

In Step (D) the mono acid 6 is reacted with the amine 4 and N'N'-dicyclohexylcarbodiimide (DCC) at e.g., room temperature in e.g., dry methylene chloride, optionally in the presence of 4-dimethylaminopyridine, to produce the amide 7.

In Step (E), the ether-amide 7 is de-esterified by e.g., 2.5 N NaOH in $MeOH/H_2O$ to yield the final product, monoacid 8.

The monoacid 8 can be treated with $NaIO_4$ in (acetone/water) at room temperature for (4–24 hours) to produce the corresponding sulfoxide 8a. Additionally, 8 can be treated with meta-chlorobenzoic acid in ($CH_2Cl_2$) at a temperature of about 0° to 25° C. for (1–24 hours) to produce the corresponding sulfone 8b.

In Step (F) the ester 7 is treated with ammonia in (methanol) at room temperature for, e.g., 1–7 days to produce the amide 9.

Flow Chart B-3 illustrates the synthesis of the sulfur analogs of the invention compounds.

In Step G, the orthoaminothiophenol is reacted with the bromoester 2 under conditions similar to Step A to produce the thioether 11.

In Step (H), the thiother 11 is reacted with an alkylthio-alkanoic acid under similar conditions using DCC analogously as in Step D to produce the acylated ester 12.

In Step I, the ester 12 is hydrolyzed to produce the free thio acid 13, which has the 5-α-reductase activity described herein.

As seen in Flow Chart C-3, the compound 13 can further be oxidized to the sulfoxide in Step $J_a$, starting with the thio compound 14 to produce the sulfoxide 15, which can be hydrolyzed, analogous to the conditions in Step I to produce the active acid 16.

In a similar manner, 14 can be converted to the sulfone-ester 17, which can then be hydrolyzed analogous to the conditions in Step I to the corresponding acid 18.

Alternatively, the sulfur in o-nitrobenzene thiol as a separate starting material analogous to 1, can be coupled to yield the ester alkylthio compound corresponding to 3 which can be oxidized to the corresponding sulfoxide or sulfone, then followed by reduction of the nitro group to the amino and then coupled with a suitable reagent e.g., 6, to yield the linear amide containing unoxidized sulfur analogous to 7. A further modification is where the sulfuracylating agent is first oxidized to the corresponding sulfoxide or sulfone, then coupled with the amino group of e.g., 11 to yield e.g. 13 containing only an oxidized sulfur in the amide chain.

It is obvious that other nitrophenols can be substituted for 1 in Flow Chart A-3 to provide the scope of the compounds covered by this invention and include the following:

2-nitrophenol
2-nitro-6-methylphenol
2-nitro-5-methylphenol
2-nitro-4-methylphenol
2-nitro-3-methylphenol
2-nitro-4-phenylphenol
2-nitro-5-phenylphenol
2-nitro-4-chlorophenol
2-nitro-4-(trifluoromethyl)phenol
2-nitro-4-methoxyphenol
2-nitro-6-ethoxyphenol, and the like.

Starting materials for Flow Charts B-3 and C-3 in addition to 10 are commercially available and readily made by prior art procedures and include all of the above listed compounds where —SH is substituted for —OH, ortho to the nitro group.

Other starting materials for 2 in both Flow Charts A-3 and B-3 include the following:

Br—CH$_2$—COOMe,
Cl—CH$_2$CH$_2$CH$_2$COOCH(CH$_3$)$_3$,
Br—CH$_2$CH$_2$CH$_2$CH$_2$COOMe,
Br—CH$_2$CH$_2$CH$_2$CH$_2$CH$_2$COOEt,
Br—CH$_2$CH$_2$CH$_2$CH$_2$CH$_2$CH$_2$COOCH$_2$CH$_2$CH$_2$CH$_3$,
Br—CH$_2$CH(CH$_3$)COOMe,
Br—CH$_2$CH(CH$_3$)CH$_2$COOEt,
Br—CH$_2$CH$_2$CH$_2$COOMe,
Br—CH$_2$CH(OCH$_3$)CH$_2$COOCH(CH$_3$)$_2$,
Cl—CH$_2$CH(OCH$_2$CH$_3$)CH$_2$COOMe,
Br—CH$_2$CH(F)CH$_2$COOMe, and the like.

Other starting materials for the acid 6 to produce the acid for acylating the amino group in 4 or 11 include the following:

MeS—(CH$_2$)$_6$COOH,
MeS—(CH$_2$)$_7$COOH,
(CH$_3$)$_2$CHS—(CH$_2$)$_8$COOH,
EtS—(CH$_2$)$_9$COOH,
CH$_3$CH$_2$CH$_2$S(CH$_2$)$_{10}$COOH,
(CH$_3$)$_2$CHS(CH$_2$)$_{11}$COOH,
MeS—(CH$_2$)$_{12}$COOH,
EtS—(CH$_2$)$_{13}$COOH,
CH$_3$CH$_2$CH$_2$S—(CH$_2$)$_{14}$COOH,
(CH$_3$)$_2$CHS—(CH$_2$)$_{15}$COOH,
CH$_3$(CH$_2$)$_3$S—(CH$_2$)$_{16}$COOH,
(CH$_3$)$_2$CH—CH$_2$S—(CH$_2$)$_{17}$COOH,
CH$_3$—CH$_2$—CH$_2$—S—(CH$_2$)$_{18}$COOH,
(CH$_3$)$_2$CHS—(CH$_2$)$_{19}$COOH,
EtS—(CH$_2$)$_{20}$COOH,
MeS—CH(CH$_3$)—(CH$_2$)$_{10}$COOH,
(CH$_3$)$_2$CHS—CH$_2$CH$_2$CH(CH$_3$)CH$_2$COOH, $$\text{MeS}-\text{CH}_2\text{CH}_2\text{CH}-\text{CH}_2\text{COOH}$$
$$|$$
$$\text{Cl}$$

EtS—CH$_2$CH(OCH$_3$)(CH$_2$)$_7$COOH,
CH$_3$CH$_2$CH$_2$S—CH$_2$CH(OCH$_2$CH$_3$)CH$_2$CH$_2$COOH,
CH$_3$(CH$_2$)$_7$—S—CH$_2$—COOH
(CH$_3$)$_2$CH(CH$_2$)$_5$—S—CH$_2$—COOH
CH$_3$(CH$_2$)$_9$—S—CH$_2$—COOH
CH$_3$(CH$_2$)$_{11}$S—CH$_2$COOH, and the like.

Representative compounds of the instant invention include, but are not limited to:

4-(2-(20-Isopropylthioeicosanoylamino)phenoxy)butyric acid;
4-(2-(19-Methylthiononadecanoylamino)phenoxy)butyric acid;
4-(2-(18-Ethylthiolooctadecanoylamino)phenoxy)butyric acid;
4-(2-(17-Isopropylthioheptadecanoylamino)phenoxy)-butyric acid;
4-(2-(16-Methylthiohexadecanoylamino)phenoxy)butyric acid;
4-(2-(15-Methylsulfinylpentadecanoylamino)phenoxy)-butyric acid;
4-(2-(14-Methylsulfinyltetradecanoylamino)phenoxy)-butyric acid;
4-(2-(13-n-Propylthiotridecanoylamino)phenoxy)-butyric acid;
4-(2-(12-n-Butylsulfinyldodecanoylamino)phenoxy)-butyric acid;
4-(2-(11-sec-Butylthioundecanoylamino)phenoxy)-butyric acid;
4-(2-(10-phenylthiodecanoylamino)phenoxy)-butyric acid;
4-(2-(10-benzylthiodecanoylamino)phenoxy)-butyric acid;
4-(2-(10-iso-Butylsulfonyldecanoylamino)phenoxy)-butyric acid;
4-(2-(9-t-Butylthiononanoylamino)phenoxy)butyric acid;
4-(2-(8-Ethylsulfonyloctanoamino)phenoxy)butyric acid;
4-(2-(7-Isopropylthioheptanoylamino)phenoxy)butyric acid;
4-(2-(6-Methylthiohexanoylamino)butyric acid;
4-(2-(20-Ethylsulfonyleicosanoylamino)phenylthio)-butyric acid;
4-(2-(19-Isopropylthiononadecanoylamino)phenylthio)-butyric acid;
4-(2-(18-Methylthiooctadecanoylamino)phenylthio)-butyric acid;
4-(2-(17-Ethylthioheptadecanoylamino)phenylthio)-butyric acid;
4-(2-(16-Isopropylhexadecanoylamino)phenylthio)-butyric acid;
4-(2-(15-Methylthiopentadecanoylamino)phenylthio)-butyric acid;
4-(2-(14-Methylsulfinyltetradecanoylamino)phenylthio-butyric acid;
4-(2-(13-Methylsulfonyltridecanoylamino)butyric acid;
4-(2-(12-n-Propylthiododecanoylamino)phenylthio)-butyric acid;
4-(2-(11-n-Butylsulfinylundecanoylamino)phenylthio)-butyric acid;
4-(2-(10-sec-Butylthiodecanoylamino)phenylthio)-butyric acid;
4-(2-(10-phenylthiodecanoylamino)phenylthio)-butyric acid;
4-(2-(10-benzylthiodecanoyiamino)phenylthio)-butyric acid;
4-(2-(9-iso-Butylsulfonylnonanoylamino)phenylthio)-butyric acid;
4-(2-(8-t-Butylthiooctanoylamino)phenylthio)butyric acid;
4-(2-(7-Ethylsulfinylheptanoylamino)phenylthio butyric acid;
4-(2-(6-Isopropylthiohexanoylamino)phenylthio butyric acid;
3-(2-(16-Methylsulfinylhexadecanoylamino)phenoxy)-propionic acid;
4-(2-(15-Methylsulfonylisohexadecanoylamino)phenoxy)-butyric acid;
3-(2-(14-n-Propylthiotetradecanoylamino)phenoxy)-isobutyric acid;
5-(2-(13-n-Butylsulfinyltridecanoylamino)phenoxy)-valeric acid;
5-(2-(12-sec-Butylthiododecanoylamino)phenoxy)-valeric acid;
5-(2-(11-iso-Butylsulfonylisododecanoylamino)-valeric acid;
5-(2-(11-t-Butylthioundecanoylamino)valeric acid;
5-(2-(10-Ethylsulfinyldecanoylamino)valeric acid;
5-(2-(9-Isopropylthiononanoylamino)phenoxy)valeric acid;
6-(2-(9-Methylthiononanoylamino)phenoxy)caproic acid;
6-(2-(8-Ethylthiooctanoylamino)phenoxy)caproic acid;
6-(2-(7-Isopropylthioisooctanoylamino)phenoxy)caproic acid;
7-(2-(7-Methylheptanoylamino)phenoxy)enanthic acid;

7-(2-(6-Methylsulfinylhexanoylamino)phenoxy)enanthic acid;
7-(2-(5-Methylsulfonylisohexanoylamino)phenoxy)-enanthic acid;
2-(2-(12-n-Propylthiododecanoylamino)phenoxy))acetic acid;
2-(2-(11-n-Butylsulfinylundecanoylamino)phenoxy)acetic acid;
2-(2-(10-sec-Butylthiodecanoylamino)phenoxy)acetic acid;
3-(2-(9-iso-Butylsulfonylnonanoylamino)propionic acid;
3-(2-(12-t-Butylthiododecanoylamino)phenylthio)-propionic acid;
3-(2-(11-Ethylsulfinylundecanoylamino)phenylthio)-propionic acid;
4-(2-(11-Isopropylthioundecanoylamino)phenylthio)-butyric acid;
4-(2-(11-Methylthioundecanoylamino)-4-methylthiophenoxy)butyric acid;
4-(2-(12-Ethylthiododecanoylamino)phenylthio)-butyric acid;
5-(2-(11-Isopropylthioundecanoylamino)phenylthio)-valeric acid;
5-(2-(10-Methylthiodecanoylamino)phenylthio)valeric acid;
5-(2-(9-Methylsulfinylnonanoylamino)phenylthio)-valeric acid;
5-(2-(12-Methylsulfonyldodecanoylamino)phenylthio)-valeric acid;
5-(2-(11-n-Propylthiodecanoylamino)phenylthio)-valeric acid;
5-(2-(10-n-Butylsulfinyldecanoylamino)phenylthio)-valeric acid;
6-(2-(9-sec-Butylthiononanoylamino)phenoxy)caproic acid;
6-(2-(12-iso-Butylsulfonyldodecanoylamino)phenylthio) caproic acid;
6-(2-(11-t-Butylthioundecanoylamino)phenylthio)-caproic acid;
7-(2-(11-Ethylsulfinylundecanoylamino)-3-methylphenylthio)enanthic acid;
7-(2-(11-Isopropylthioundecanoylamino)-4-methylphenylthio)enanthic acid;
7-(2-(12-Methylthiododecanoylamino)phenoxy)enanthic acid;
4-(2-(11-Phenylthioundecanoylamino)4-methyl-phenoxy)butyric acid;
4-(2-(10-Benzylthiodecanoylamino)3-methylphenoxy)-butyric acid;
4-(2-(9-Methylthiononanoylamino)5-methylphenoxy)-butyric acid;
4-(2-(12-Methylsulfinyldodecanoylamino)6-methylphenoxy)butyric acid;
4-(2-(11-Methylsulfonyldecanoylamino)3-phenylthio)butyric acid;
4-(2-(10-n-Propylthiodecanoylamino)4-methylphenoxy)-butyric acid;
4-(2-(9-n-Butylsulfinylnonanoylamino)5-fluoromethylphenylthio)butyric acid;
4-(2-(12-sec-Butylthiododecanoylamino)6-methylphenoxy) butyric acid;
5-(2-(11-iso-Butylsulfonylundecanoylamino)-3-methylphenylthio)valeric acid;
4-(2-(11-t-Butylthioundecanoylamino)-3-methylsulfonylphenoxy)butyric acid;
4-(2-(11-Ethylsulfinylundecanoylamino)-4-methylsulfonylphenylthio)butyric acid;
4-(2-(12-Isopropylthiododecanoylamino)5-ethylphenoxy) butyric acid;
4-(2-(11-Methylthioundecanoylamino)4-phenylphenoxy)-butyric acid;
4-(2-(10-Ethylthiodecanoylamino)-3,5-dimethylphenoxy)-butyric acid;
4-(2-(9-Isopropylthiononanoylamino)-4-fluoro-phenoxy)-butyric acid;
4-(2-(12-Methylthiododecanoylamino)-5-trifluoromethylphenoxy)butyric acid;
4-(2-(11-Isopropylthio)undecanoylamino)phenoxy)butyric acid,
4-(2-(11-Ethylthio)undecanoylamino)phenylthio)butyric acid,
4-(2-(9-Isopropylthio)nonanoylamino)phenoxy)butyric acid,
4-(2-(10-Isopropylthio)decanoylamino)phenoxy)butyric acid,
4-(2-(12-Isopropylthio)dodecanoylamino)phenoxy)butyric acid,
4-(2-(13-Butylthio)tridecanoylamino)phenoxy)butyric acid,
4-(2-(15-t-Butylthio)pentadecanoylamino)phenoxy)butyric acid,
5-(2-(11-Isopropylthio)undecanoylamino)phenoxy)valeric acid,
4-(2-(11-Ethylsulfinyl)undecanoylamino)-phenoxy)butyric acid,
4-(2-(11-Isopropylsulfonyl)undecanoylamino)-4-methylphenoxy)butyric acid,
4-(2-(11-Ethylsulfinyl)undecanoylamino)-5-methylphenoxy)butyric acid.

All of the compounds described above in the present invention, prepared in accordance with the methods described above, are, as already described, can be used to treat prostatic cancer in combination with an antiandrogen, i.e. flutamide, by oral, parenteral or topical administration.

In this invention, the antiandrogen, and the 5α-reductase inhibitor are administered in combination as separate or one single combined pharmaceutical composition via parenteral or oral means. Preferably the antiandrogen and the 5α-reductase inhibitor are administered orally as separate compositions.

The amount of each component administered is determined by the attending clinicians taking into consideration the etiology and severity of the disease, the patient's condition and age, the potency of each component and other factors.

The antiandrogen compositions are generally administered in a dosage range of about 0.20 to 40 mg/kg (body weight) per day with 250 to 750 mg per day, in equally divided doses, three (3) being preferred.

The 5α-reductase inhibitor compositions are generally administered in a dosage range of about 0.01 to 1.0 mglkg (body weight) per day with one to 70 mg per day in one daily dose being preferred.

In the preferred aspect of this invention, the antiandrogen is 4'-nitro-3'-trifluoromethylisobutyranilide, i.e. flutamide, which is administered orally in a daily dose of about 750 mg/kg; the 5α-reductase inhibitor is finasteride, which is administered orally in a daily dose of about 10 mg/kg.

The antiandrogen and the 5α-reductase inhibitor may be compounded into a single dosage form suitable for oral or parenteral administration. A tablet or capsule or caplets are particularly convenient forms for oral administration. Such compositions useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such a magnesium stearate, sodium lauryl sulfate, "Carbowax" or polyethylene glycols. Of course, taste improving substances can be added in the case of oral administration forms.

As further forms of administration, one can use plug capsules, e.g. hard gelatin, as well as closed softgelatin capsules comprising a softener or plasticizer, e.g. glycerine. The plug capsules contain the active substance preferably in the form of a granulate, e.g., in mixtures with fillers, such as lactose, saccharose, mannitol, starches such as potato starch or amylopectin, cellulose derivatives or highly-dispersed silicic acids. In softgelatin capsules, the active substance is preferably dissolved or suspended in suitable liquids, such as vegetable oils or liquid polyethylene glycols.

The active ingredient components used in accordance with the present invention may also be formulated into once-a-day or even longer sustained release composition by conventional techniques well known in the art.

In place of oral administration, the active compounds may be administered parenterally. In such case, one can use a solution of the active substance, e.g., in sesame oil or olive oil.

The compositions when administered separately can be contained in a suitable "kit" housing both pharmaceutical compositions in clearly-marked sections and indicating dosage regimens. The kit can be made of conventional materials.

Following the above treatment using the described regimen, prostate cancer can be significantly inhibited, and in some cases reversed into remission, when treating such androgen-dependent diseases in accordance with this invention.

To assist in determining the effect of the prostatic cancer treatment, blood plasma concentrations of testosterone (T), dihydrotestosterone (DHT), and prostate acid phosphatase (PAP) as well as prostate volume are measured. Lowered concentrations of DHT and prostatic PAP, and reduction in prostate volume, are indicative of successful treatment. The concentrations of the above-listed components in plasma can be measured by standard methods well known to those skilled in the art. (See, for example, R. Neri and M. Monahan, Invest. Urology (1972), 10, 123–130 for prostatic AP staining and E. Nieschlay and D. L. Loriaux, Z. Klin Chem. Klin Biochem (1972), 4, 164 for radioimmunoassay determinations of T.

The prostate volume is measured by rectal examination and/or by transrectal ultrasonography. Objective assessment of the effect of treatment is also measured by physical methods well known to these skilled in the art of nuclear magnetic resonance imaging, as well as by physical examination.

Further, and more desirably the effect of the combination therapy can be quantified and evaluated by measuring the changes in serum concentrations of prostate specific antigen (PSA). This is a 35K dalton glycoprotein antigen, associated only with prostatic tissue, discovered by Wang in 1979. (See *Invest Urol*, Vol. 17, p. 159 (1979.) Since that discovery, described in *Supplement to Biology*, Vol. 37, No. 5, pp. 11–16 (May 1989) the clinical importance of this new tumor marker has been recognized and is now widely accepted as representing a significantly more effective and reliable tumor marker than prostatic acid phosphatase (PAP).

Protocols for the clinical use of PSA marker in screening tests for prostate cancer to determine staging and to monitor response to therapy are published in the art. (See *Journal of Urology*, Vol. 142, pp. 1011–1017 (October 1989) by M. A. Hudson, et al.)

Using a protocol similar to that described in the above Hudson paper, in which PSA was monitored, clinical trials on the effect of finasteride were conducted. This study is the first clinical trial to evaluate its efficacy in prostate cancer. Twenty-eight hormone-naive patients with stage D prostate cancer were randomized in a double-blinded fashion to receive MK-906 (10 mg/day) or placebo. Patients were evaluated at 3 week intervals by rectal examination and serum PSA, and at 6 week intervals by bone scan and transrectal ultrasound. Patients were discontinued at the investigators discretion when PSA levels increased from baseline. After 12 weeks patient on placebo were switched to finasteride.

Thirteen patients received MK-906 and 15 patients received placebo. A statistically significant decrease in the median percentage change from baseline in PSA at weeks 3 and 6 occurred in the MK-906 group compared to the placebo group (−22.9% vs. −2.9%, and −15.1% vs. +9.9%, respectively). Patients who remained on continuous therapy for 24 weeks had 35–40% suppression in PSA. Serum testosterone was not affected while dihydrosterosterone was markedly lowered by MK-906 to castrate levels. Three patients in each treatment group progressed on bone scan while none demonstrated regression.

In summary, a decrease in serum PSA in the MK-906 treatment group suggests that MK-906 exerts a tumor suppressive effect on prostate cancer cells. While the magnitude of this effect does not appear similar to medical or surgical castration, it has an excellent safety profile and potential for preservation of sexual potency.

The combination a 5α-reductase inhibitor and antiandrogen, i.e. of finasteride and flutamide, will exhibit an even greater effect on suppression of prostate cancer cells/tumors in patients with stages (A to D) of prostatic adenocarcinoma, in which the tumors are still androgen-dependent.

The method of preparing the compounds of the present invention, already described above in general terms, may be further illustrated by the following examples which should not be construed as being limitations on the scope or spirit of the instant invention.

CHAPTER 1

Example 1

Methyl 3-oxo-4-aza-5α-androst-1-ene-17β-carboxylate

A suspension of 83.7 g of methyl 3-oxo-4-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO$_3$ solution and saturated NaCl solution, then dried and evaporated to leave 172.4 g. This material was chromatographed on 2.56 kg of silica gel eluting first with dichloromethane (5 l) and then with 4:1 dichloromethane acetone. The desired product eluted after 8 l and amounted to 53.4 g. It was rinsed with diethyl ether and dried to leave 49.5 g, of the title compound m.p. 278–280° C. In a similar fashion the following compounds were converted to their corresponding 1,2-unsaturated derivatives:

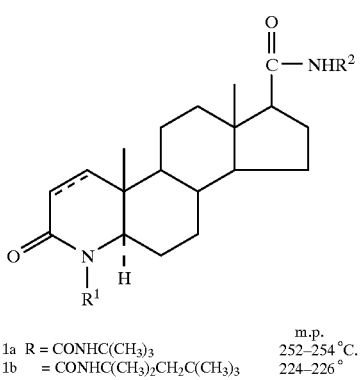

II

1a R = CONHC(CH3)3    m.p. 252–254 °C.
1b   = CONHC(CH3)2CH2C(CH3)3    224–226°

\* Rasmusson Johnston and Arth. U.S. Pat. No. 4,377,584, Mar. 22, 1983.

Example 2
Methyl 4-methyl-3-oxo-4-aza-5α-androst-1-ene-17-carboxylate

A suspension of 25 g of the product of Example 1 and 2.25 g of sodium hydride in 500 ml of dry dimethylformamide was stirred under nitrogen for 15 minutes. Methyl iodide (15 ml) was added dropwise and the mixture was stirred for 30 minutes at room temperature. Additional (5 ml) methyl iodide was added and the mixture was heated at 50° C. for 2 hours. After cooling the mixture was diluted with water to a volume of 2 liters. The solid was separated after cooling and amounted to 25.4 g, m.p. 159–161° C.

In a similar fashion the following compounds were converted to their corresponding 4-methyl derivatives:

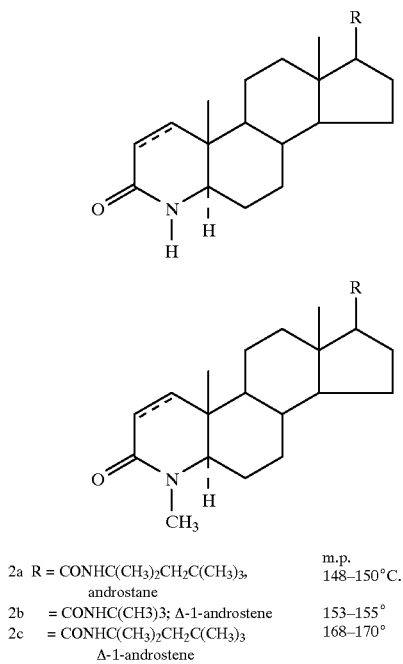

2a R = CONHC(CH3)2CH2C(CH3)3, androstane    m.p. 148–150°C.
2b   = CONHC(CH3)3; Δ-1-androstene    153–155°
2c   = CONHC(CH3)2CH2C(CH3)3 Δ-1-androstene    168–170°

Example 3
S-(2-Pyridyl) 4-methyl-3-oxo-4-aza-5α-androst-1-ene-17β-thiocarboxylate A suspension of 25 g of the product of Example 2 in 125 ml of methanol was treated with a solution of KOH (*12.5 g) in 12.5 ml of water. After refluxing for 4 hours, the solution was acidified with 6 NHCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218–220° C.

Continued elution with acetone gave 5.2 g of the methanol addition product, S-(2-pyridyl) 1α-methoxy-4-methyl-3-oxo-4-aza-5α-androstane-17β-thiocarboxylate, m.p. 221–223° C. as a by-product.

3A. In a similar fashion the product of Example 1 was converted into S-(2-pyridyl) 3-oxo-4-aza-5α-androst-1-ene-17β-thiocarboxylate, m.p. 230–232° C.

3B. In a similar manner methyl 3-oxo-4-aza-5α-androstane 17β-carboxylate was converted into S-(2-pyridyl) 3-oxo-4-aza-5α-androstane-17β-thiocarboxylate, m.p. 232–234° C.

Example 4
N-t-butyl 4-methyl-3-oxo-4-aza-5α-androst-1-ene-17β-carboxamide

Anhydrous t-butylamine was added to a suspension of 2.5 g of the pyridylthioester of Example 3 in 70 ml of tetrahydrofuran. After 60 minutes exposure, the resulting solution was evaporated and the residue was chromatographed on 125 g of silica gel. Elution with 20:1 ethyl acetate dichloromethane afforded 1.5 g of the product, m.p. 152–154° C.

When the example is repeated using an appropriate amine and an appropriate pyridylthioester, the following products were obtained:

4b: N-t-butyl 3-oxo-4-aza-5α-androstane-17β-carboxamide, m.p. 275–276° C.

4c: N-(2,4,4-trimethyl-2-pentyl) 4-methyl-3-oxo-4-aza-5α-androst-1-ene-17β-carboxamide, m.p. 168–170° C.

Example 5
5-Oxo-3,5-secoetian-3,20-dioic acid

To a solution of 200 g of 3-oxo-4-etien-17β-oic acid in 3.5 l of t-butanol at 80° was added a solution of 198.4 g of sodium carbonate in 474 ml of water. A warm (65° C.) solution of 948.5 g of sodium metaperiodate and 6.95 g of permanganate in 3.5 l of water was added at such a rate that the reaction mixture was maintained at 80° C. After addition the mixture was heated at reflux for one hour. The mixture stood at room temperature overnight. The inorganic salts were removed by filtration and the cake was washed with 225 ml of water. A solution of 5% aqueous sodium bisulfite was added to reduce the iodine that was present. The t-butanol was removed under reduced pressure and the aqueous residue was acidified with conc. hydrochloric acid. The separated gum was extracted into dichloromethane and was washed with 5% aqueous sodium bisulfite, saturated sodium chloride solution, then dried and concentrated to an off-white residue (214 g). Crystalline material was obtained by suspending the residue in ether and diluting with hexane to give 152 g, m.p. 189–192° C.

Example 5B
3-Oxo-4-aza-5-etien-20-oic acid

A suspension of 64.7 g of the dioic acid of Step 5 in 350 ml of ethylene glycol was treated with 80 ml of liquid ammonia. The resulting solution was heated at a rate of 3°/min. up to 180° C. and was held at that temperature for 15 minutes. After cooling, 1 liter of water was added and the mixture was acidified with 10% hydrochloric acid to a pH of 1.5. The product was removed and washed with water, then air dried to leave 57.5 g of the product, m.p. 310° C.

Example 5C
3-Oxo-4-aza-5α-etian-20-oic acid

A solution of 136 g of the 5-acid of Example 5B in 16.32 ml of acetic acid was hydrogenated at 60° C. in the presence of platinum catalyst (from 16.32 g of $PtO_2$) at 40 psig for 3 hours. The catalyst was removed and the solution concentrated to give 128.2 g of crude product. The material was washed well with 3 l of water then filtered an air dried to leave 125 g of the white solid, m.p. 310°.

This material is also obtained by saponification of methyl 3-oxo-4-aza-5α-androstane-17β-carboxylate (methyl 3-oxo-4-aza-5α-etien-17β-oate) in 7% methanolic potassium hydroxide followed by an acidic work-up.

Example 5D
N-(2,4,4-trimethyl-2-pentyl)3-oxo-4-aza-5α-androstane-17β-carboxamide A solution of 5.0 g of the product of Example 5C, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 2,4,4-trimethyl-2-pentylamine (t-octylamine). This solution stood at room temperature for 64 hours. A small amount of solid was removed and the solution was washed successively with 10% aqueous sodium hydroxide, water, 10% hydrochloric acid and saturated aqueous sodium chloride. After drying and concentration the crude product was eluted through 240 g of silica gel with 3:7 acetone-dichloromethane to give 5.5 g of the product, m.p. 250–251° C.

Example 5E

Example 5D is repeated using t-butylamine in place of 2,2,4-trimethyl-2-pentylamine to obtain N-t-butyl 3-oxo-4-aza-5α-androstane-17β-carboxamide, m.p. 274–276° C.

Example 6
Synthesis of 17β(N-1-adamantyl-carbamoyl)-4-aza-5α-androst-1-en-3-one 100 mg of the 17-methyl ester (0.305 mmoles) from Example 1 was suspended in 3.0 ml of THF (dried over molecular sieves 3A), and then was added 183.0 mg of 1-adamantanamine (1.2 mmoles). The suspension was cooled to 5–10° C. and then 590 μl of 2.0 M solution, of EtMgBr in THF was added. The resulting mixture was allowed to stir for 10 minutes, and then refluxed for 1–2 hours under $N_2$. The mixture was cooled to 0° C. and then quenched with saturated solution of $NH_4Cl$ (about 10 ml.). The organic layer was separated and the aqueous layer extracted with three volumes $CH_2Cl_2$.

The organic layers were combined, washed 2 times with $H_2O$, twice with saturated sodium chloride, and dried over $MgSO_4$, filtered and evaporated to dryness in vacuum. Crystallization from EtOAc afforded 75.0 mg of product. Recrystallization from MeOH and drying at 110° C. for 2 hours/0.1 mm gave product, mpt. 305–306° C. Molecular weight (by FAB) showed $M^+=451$; Calculated=451.

Anal. Calcd. for $C_{29}H_{42}N_2O_2$: C,77.28; H,9.40; N,6.21. Found: C,76.84; H,9.73; N,5.93.

Example 7
Synthesis of 17β(N-2-adamantyl-carbamoyl)-4-aza-5α-androst-1-en-3-one Following the above-described general procedure of Example 6 but utilizing 2-adamantamine (prepared by aqueous neutralization of the hydrochloride and EtOAc extraction and isolation) in place of 1-adamantamine, and carrying out the reflux for 7 hours rather than 1–2 hours, the title compound is prepared, mpt. 284–285° C.

Example 8
Synthesis of 17β(N-1-adamantylcarbamoyl)-4-aza-5α-androstane-3-one 100.0 mg of the adamantyl derivative produced in Example 6 was dissolved in 5.0 ml of dry THF. 300 mg of 5% Pd/C was added and the mixture was hydrogenated for 6.0 hrs. at R.T. at 40 psi. The mixture was filtered through celite, the cake washed with THF (3 times) and solvent evaporated under vacuum to yield 97.0 mg. of crude above-titled product. NMR showed absence of olefins. The crude material was placed on 15.0 g silica gel column, and eluated with 1:1($CH_2Cl_2$: acetone).

Collected fractions afforded a single spot material by TLC weighing 77.98 mg. NMR was in excellent agreement with the proposed structure. Recrystallized from EtOAc to yield 65.59 mg of the above-titled product, mp. 323–324° C.

Anal. Calcd. for $C_{29}H_{44}O_2N_2$ 1/4 $H_2O$: C,76.18; H,9.81; N,6.13. Found: C,75.91; H,9.97; N,6.06.

Example 9
Synthesis of 17β(N-1-adamantylcarbamoyl)-4-methyl-4-aza-5α-androst-1-en-3-one 120 mg of the thiopyridyl ester of Example 3 was suspended in 20 ml of dry THF, to the suspension was added 175.0 mg of 1-adamantanamine under $N_2$. The reaction was carried out at R.T. for 16 hours under $N_2$. The reaction was monitored by silica gel TLC, using 1:1 acetone: hexane. The product was separated on TLC 20 cm×20 cm, 1000 μm silica gel plate, eluted with 1:1 (acetone/hexane). The product was crystallized from ethyl acetate, to give 50.0 mg of pure material m. pt. 202–205° C. Molecular Weight (FAB) showed 465; Calc: 465. Recrystallization afforded 19.14 mg of the above-titled product, m.pt. 202–202.5° C.

Anal. Calcd for $C_{30}H_{44}N_2O_2.H_2O$: C,74.64; H,9.60; N,5.80. Found: C,74.32; H,9.47; N,5.89

Example 10
Hydrolysis of Methyl-3-oxo-4-aza-5α-androstane-17β-carboxylate

The 17β-androstane carboxylate starting material of Example 1 was hydrolyzed with 7% KOH in isopropanol or aqueous methanol, followed by an acidic work-up to give the corresponding 17β carboxylic acid which was utilized in Example 11.

Example 11
N-(1-adamantyl)-3-oxo-4-aza-5α-androstane-17β-carboxamide

A solution of 5.0 g of the product of Example 10, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 1-adamantamine. This solution stood at room temperature for 64 hours, then filtered, and the solution was washed successively with 10% hydrochloric acid and saturated aqueous sodium chloride. After drying with $MgSO_4$, it was filtered and concentrated. The crude product was eluted through 240 g of silica gel with 3:7 (acetone-dichloromethane) to give 5.5 g of the above-titled product, m.p. 323–324° C.

Example 12

Synthesis of Benztriazol-1-yl-3-oxo-4-methyl-4-aza-5α-androstan-17β-carboxylate

A suspension of 83.7 g of methyl-3-oxo-4-methyl-4-aza-5α-androstane-17β-carboxylate. (See Rasmusson, et al. J. Med. Chem 29, 2298–2315, 1986) was hydrolyzed with 7% KOH in aqueous methanol, followed by an acidic work up to give the corresponding 17β-carboxylic acid.

The acid was readily converted into benzotriazyl-1-yl-3-oxo-4 methyl-4-aza-5α-androstane 17β carboxylate as described in Example 13. The activated ester (the benzotriazoyl derivative) was purified on TLC (4 plates, 20 cm×20 cm×20 cm×1000 μm silica gel) eluted with 4:96 (MeOR-CHCl$_3$). The isolated product was washed with ether to give the active ester m.pt. 198–200° C. with decomposition.

Example 13

Synthesis of 17β (N-1-adamantylcarbamoyl)-4-methyl-4-aza-5α-androstan-3-one 100.0 mg of the 4-methyl-4-aza-benzotriazole derivative prepared as described in Example 12, was dissolved in 20.0 ml CH$_2$Cl$_2$. To the clear solution was added 127 mg of 1-adamantamine. The reaction mixture was stirred overnight at R.T./N$_2$.

Crystallization from EtOAc after filtering the solution through Teflon Acrodisc CR afforded 26.32 mg, m.pt. 210–217° C. The product was further purified on 1.0 g silica gel column (EM silica gel) with 1:1 (acetone-hexane) as eluant to give after recrystallization (ethyl acetate) 21.75 mg of white needles of the above-titled product, m.pt. 203–205° C.

Anal. Calcd. for C$_{30}$H$_{46}$N$_2$O$_2$.1.5 H$_2$O: C,73.58; H,9.68; N,5.62; Found: C,73.15; H,9.30; N,5.67.

Example 14

Diastereomeric Synthesis of 17β(N-exo-2-norbornanylcarbamoyl)-4-aza-5α-androst-1-en-3-one)

100.0 mg of the corresponding 4-H thiopyridyl ester of Example 3, prepared by the procedure of Example 3, but utilizing the 4-H methyl ester product of Example 1, (See Rasmusson et al. J. Med. Chem. Vol. 29, pp. 2298–2315 (1986), was dissolved in 3.0 ml of dry THF under N$_2$. To the clear solution was added 477 μl of (±) racemic exo-2-aminonorbornane. Allowed the reaction to proceed for 16 hours at R.T./N$_2$. The reaction mixture was evaporated to dryness in vacuum. The residue was dissolved in chloroform. The organic layer was washed with 2.5 N HCl acid (3 times); 3 times with water; 3 times with saturated NaCl solution, dried over MgSO$_4$, filtered and evaporated to dryness in vacuum to afford 56.3 mg of a racemic diastereomeric mixture.

The crude product was chromatographed on TLC (2 plates, 20 cm×20 cm×500 μm silica gel) eluted with 70:30 (CHCl$_3$:acetone) to yield 43.4 mg of the above-titled product. Recrystallization from EtOAc yielded 30 mg product, m.pt 245–245.9° C.

NMR (CDCl$_3$) confirmed the above structure. FAB mass spectrum calcd. for C$_{26}$H$_{38}$O$_2$N$_2$: m/e 411; Found: 411. Anal. Calcd. for C$_{26}$H$_{38}$O$_2$N$_2$.H$_2$O: C,72.82; H,9.40; N,6.58. Found: C,73.21; H,9.20; N,6.25.

Example 15

Synthesis of 17β(N-1-adamantylmethylcarbamoyl)-4-aza-5α-androst-1-en-3-one 200.0 mg of the 4-H thiopyridyl aza steroid, used in Example 14, was suspended in 2.0 ml of dry THF.

To the suspension was added 400 μl of 1-aminomethylene adamantane via syringe at R.T./N$_2$. After several minutes, a yellow clear solution resulted and after ½ hr., precipitation occurred. The reaction was allowed to proceed overnight/N$_2$. Diluted with CH$_2$Cl$_2$, washed with 10% NaOH, two times, then with H$_2$O two times, followed by 10% HCl (two times), H$_2$O (two times), and finally two times with satd. NaCl solution.

The organic layer was dried over MgSO$_4$, filtered, concentrated in vacuo to obtain the product, as shown by NMR, recrystallized from EtOAc, to yield 149.0 mg product, m.pt 255–257° C. with decomposition.

FAB Mass Spectrum, Calcd: m/e 464+1=465: Found 465.

Example 16

Synthesis of 17β(N-2-adamantylcarbamoyl)-4-aza-5α-androstan-3-one

A mixture of 1.09 grams 17β-(N-2-adamantylcarbamoyl)-4-aza-5α-androst-1-en-3-one (See Example 10 for preparation), 150 ml of ethanol, and 1.0 g. of 30% Pd/C was hydrogenated overnight with shaking under 45 psig. hydrogen pressure. The suspension was filtered to remove catalyst, and evaporated to dryness to yield a grey residue. This was chromatographed by elution on a 200 ml silica gel column with 40:60 acetone/methylene chloride eluant to yield 1.0 g of solid, mp. 294–296° C.

Anal. Calcd. for C$_{29}$H$_{44}$N$_2$O$_2$.0.2H$_2$O; Calcd. C, 76.33; H, 9.80; N, 6.14; Found C, 76.23; H, 9.86; N, 5.92; Mass Spec. Analysis by electron impact showed MW of 452.

Example 17

Synthesis of 17β-(N-2-adamantylcarbamoyl)-4-aza-4-methyl-5α-androst-1-en-3-one

A suspension of 500 mg of 17β-(N-2-adamantylcarbamoyl)-4-aza-5α-androst-1-en-3-one, as prepared in Example 16, 10 ml sieve-dried DMF, 140 mg NaH, were heated and stirred at 70° C. under a nitrogen atmosphere for 18 hours. Cooled to room temperature and then added 0.4 ml methyl iodide dropwise with stirring which was continued at 50° C. for 3 hours. The reaction mixture was then treated by cooling to room temperature, followed by the addition of 15 ml water. The mixture was extracted with 3×20 ml of CH$_2$Cl$_2$. The organic layers were combined, washed with brine, dried and evaporated to yield a white crystalline residue. Recrystallization from ethyl acetate/CH$_2$Cl$_2$ yielded a pure white solid, mp 246–248° C.

Analysis calculated for C$_{30}$H$_{44}$N$_2$O$_2$.0.3H$_2$O; Calcd. C, 76.65; H, 9.56; N, 5.95; Found C, 76.50; H, 9.75; N. 5.84 ; Mass spectroscopy showed a molecular weight of 464.

Example 18

Synthesis of 17β-(N-2-adamantylcarbamoyl)-3-oxo-4-methyl-4-aza-5α-androstane

17β-(N-2-adamantylcarbamoyl)-4-methyl-4-aza-androsten-1-en-3-one, (200 mg) as prepared in Example 17, were placed into 25 ml absolute ethanol with 200 mg 30% Pd/C hydrogenation catalyst. The suspension was rocked overnight under 40 psig hydrogen pressure.

The suspension was filtered, and the filtrate evaporated to dryness. The residue was recrystallized from hot ethyl acetate to give a white crystalline solid, mp. 113–115° C. Calcd. for C$_{32}$H$_5$ON$_2$O$_3$.0.5 EtOAc

Example 19
Synthesis of 17β-(N-methyl-N-2-adamantyl) carbamoyl-4-methyl-4-aza-androst-1-en-3-one 17β-(N-2-adamantyl)carbamoyl-4-aza-androst-1-en-3-one (5.0 g) and 1.5 g sodium hydride in 100 ml dry DMF were stirred under dry nitrogen for 3 hours at 40° C. The reaction was cooled to room temperature and about 4 ml of methyl iodide was added dropwise and allowed to stir at room temperature for one hour. The reaction was cooled in an ice bath and a large excess of about 250 ml, water was added. The aqueous mixture was extracted with $CH_2Cl_2$ (3×100 ml), the organic extracts combined, washed with $H_2O$, brine, and then evaporated to dryness to yield crude product. The crude product was eluted on an HPLC column (Si gel) with 10/1 acetone/$CH_2Cl_2$ to yield 2 peaks having retention times of 3 CV(B) and 3.8 CV(A). Peak (A) was analyzed as per the 4-methylaza titled product of Example 15. The second product (B) was analyzed as the 4-methylaza-17β-(N-methyl-N-2-adamantyl/carbamoyl analog, i.e. the titled compound, mp. 163–165.

Calcd. for $C_{31}H_{46}N_2O_2$; Calcd. C, 77.77; H, 9.68; N, 5.85; Found C, 77.29; H, 9.79; N, 5.77; Mass spectrometry showed a molecular weight of 478.

Example 20
Synthesis of 17β-(N-methyl-N-2-adamantylcarbamoyl) 4-aza-4-methyl-androstan-3-one The crude reaction mixture from Example 19 (4.6 g) was dissolved in 200 ml ethanol and together with 1.0 g 30% Pd/C was hydrogenated under 40–45 Psig a hydrogen atmosphere at room temperature overnight. The mixture was filtered, residue washed with ethanol. The ethanol solution was evaporated to dryness to yield a crude mixture. Recrystallized from $CH_2Cl_2$/diethyl ether/hexane to yield 800 mg of the pure monomethyl androstane compound of Example 16, mp 113–115° C. Second and third crops were combined with mother liquor and treated by HPLC as in Example 17 to yield the dimethylated title compound, mp 180–182° C.

Anal. Calcd. for $C_{31}H_{48}N_2O_2$; Calcd. C, 77.45; H, 10.06; N, 5.83; Found C, 77.26; H, 9.87; N, 5.82; Mass spectrometry showed a molecular weight of 480.

Example 21
N-t-Butyl Androst-3,5-diene-17β-carboxamide-3-Carboxylic Acid (a) N-t-butyl androst-3,5-diene-3-bromo-17β-carboxamide To a solution of oxalic acid (0.0011 mol, 0.1 g) and oxalyl bromide (0.0211 mol, 3 ml) in 15 ml of sieve dried toluene was added over a one hour period 1 g (0.003 mol) of androst-4-ene-3-one 17β-carboxylic acid. The reaction was stirred at room temperature for 2 hours and then it was concentrated in vacuo. The excess oxalyl bromide was removed by azetoroping with toluene. The resulting brown oil was redissolved in toluene, cooled to 0° C. and then 10 ml t-butylamine (7.0 g) in 30 ml of toluene was added dropwise over 15 minutes. Once the addition was complete, the reaction was stirred at 0° C. for 15 minutes and then it was kept at −20° C. for 19 hours. The reacton mixture was allowed to warm to room temperature and then stirred at 25° C. for one hour. The volatiles were removed in vacuo. The residue was partitioned between chloroform/water, the layers were shaken together and separated and then the aqueous phase was back-extracted twice with chloroform. The combined organic extracts were washed with water (2×) and then dried with anhydrous magnesium sulfate. The crude product was purified by flash chromatography on silica, eluting with 20% ethyl acetate in hexane, to give 1.06 g of the title compound, a white solid.

(b) N-t-Butyl Androst-3,5-diene-17β-carboxamide-3-carboxylic acid

To a solution of N-t-Butyl Androst-3,5-diene-3-bromo-17β-carboxamide (0.5 g, 0.00115 mol) in 5 ml of tetrahydrofuran, cooled to −78° C. (dry ice/acetone bath) under argon, was added dropwise 1.5 ml (0.00375 mol) of a 2.5 M solution of n-butyl lithium in hexane. The reaction mixture was stirred at this temperature for one hour and then carbon dioxide was bubbled into the reaction for 45 minutes, via a concentrated sulfuric acid tower. The reaction mixture was allowed to warm to room temperature and then it was diluted with water, aqueous HCl solution and chloroform. The layers were shaken together and separated, with the aqueous phase being back-extracted with chloroform (2×). The combined organic extracts were washed with water (2×), and brine (1×) and then dried with anhydrous magnesium sulfate. The solvents were removed under reduced pressure give 0.6 g of a crude solid. This material was slurried with hexane and a white solid was isolated (0.43 g). The title compound was recrystallized from acetonitrile, m.p. 247–250°.

CHAPTER 2

Example 1
Methyl 3-oxo-4-aza-5α-androst-1-ene-17β-carboxylate

A suspension of 83.7 g of methyl 3-oxo-aza-5α-androstane-17β-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous $NaHCO_3$ solution and saturated NaCl solution, then dried and evaporated to leave 172.4 g. This material was chromatographed on 2.56 kg of silica gel eluting first with dichloromethane (5 liters) and then with 4:1 dichloromethane-acetone. The desired product was eluted with 8 liters of the above-mixed solvent and evaporated to dryness in vacuo to yield 53.4 g solid. It was washed with diethyl ether and dried to leave 49.5 g of the above-titled product, m.p. 278–280° C.

*Rasmusson Johnston and Arth. U.S. Pat. No. 4,377,584, Mar. 22, 1983.

Example 2
S-(2-Pyridyl)-3-oxo-4-aza-5α-androst-1-ene-17β-thiocarboxylate

A suspension of 25.0 g of the above product from Example 1 was saponified with 12.5 g of KOH in 150.0 ml of 5:1 $CH_3OH$—$H_2O$ under reflux conditions for 4 hours/$N_2$. The mixture was cooled to 25° C. and acidified to pH<2. Water (175 ml) was added gradually with stirring to leave a crystalline precipitate which was collected and washed with water.

After drying, the product amounted to 25 g., m.pt 313–315° C. with decomposition.

The crude dry acid (23.0 g) was suspended in 210 ml of toluene, and to the suspension was added triphenylphosphine (56.0 g) and 2,2'-dipyridyl disulfide (48.3 g), and the mixture was stirred at 24° C. overnight/$N_2$. The reaction mixture was placed on a column of silica gel (1.3 kg) and was eluted with 1:1 (acetone/$CH_2Cl_2$). The desired thioester eluted slowly, and after rinsing with ether, yielded 36.8 g of the above-titled product, m.p. 232–235° C.

Example 3

22-Methyl-4-aza-21-nor-5α-chol-1-ene-3,20-dione

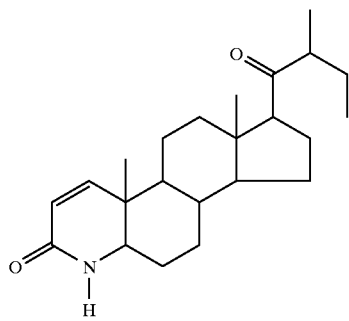

To a solution of 7.2 g of S-(2-pyridyl)-3-oxo-4-aza-5α-androst-1-ene-17α-thiocarboxylate in 288 ml of tetrahydrofuran was-added at −78° C. 33.6 ml of 1.3M S-butylmagnesium chloride. After 30 minutes at −78° C. the solution came to room temperature and was treated with saturated aqueous NaCl solution. The product was extracted into dichloromethane and was washed with saturated aqueous NaCl solution and 10% aqueous NaOH solution, then dried and concentrated. The residue was eluted through 430 g of silica gel with 9:1 dichloromethane-acetone to give 4.5 g of the product, m.p. 246–249° C.

When the procedure is repeated using the following reagents, the indicated product is obtained.

| Starting Material | Reagent | Product |
|---|---|---|
| S-(2-pyridyl)3-oxo-4-aza-5α-androst-1-ene-17β-thiocarboxylate | 2-pyrrolyl magnesium chloride | 17β-(2-pyrrolyl-carbonyl)-4-aza-5α,-androst-1-ene-3-one m.p. 294–296° C. |
| S-(2-pyridyl)3-oxo-4-methyl-5α-androst-1-ene-17β-thiocarboxylate | sec-butyl magnesium chloride | 4,22-dimethyl-4-aza-21-nor-5α-chol-1-ene-3,20-dione m.p. 134–136° C. |
| S-(2-pyridyl)3-oxo-4-methyl-4-aza-5α-androst-1-ene-17β-thio-carboxylate | 2-pyrrolyl magnesium chloride | 4-methyl-17β-(2-pyrrolylcarbonyl)-4-aza-5α-androst-1-ene-3-one m.p. 234–238° C. |
| S-(2-pyridyl)3-oxo-4-aza-5α-androst-ene-17β-thiocarboxylate | isobutyl magnesium chloride | 23-methyl-4-aza-21-nor-5α-cholane-3,20-dione m.p. 220–222° C. |

Example 4
22-Methyl-4-aza-21-nor-5α-chol-1-ene-3,20-dione

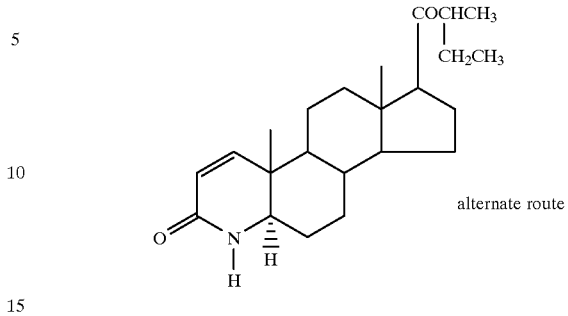

alternate route

A solution of 21 g of 22-methyl-4-aza-21-nor-5α-cholane-3,20-dione and 29.49 g of benzeneseleninic anhydride in 552 ml of chlorobenzene was refluxed with water separation for 4 hours. The mixture was concentrated and the residue was redissolved in dichloromethane. After washing with 10% aqueous sodium hydroxide, then 10% hydrochloric acid and saturated aqueous sodium chloride the solution was dried and concentrated to 45 g of yellow residue. This was chromatographed on 1.5 kg of silica gel packed in dichloromethane and eluted with ethyl acetate to give 10.6 g of the product, m.p. 248–251° C.

When the procedure is repeated using 23-methyl-4-aza-21-nor-5α-cholane-3,20-dione as starting material the product obtained is 23-methyl-4-aza-21-nor-5α-chol-1-ene-3,20-dione, m.p. 283–286° C.

Example 5
17β-(phenylcarbonyl)-4-aza-5α-androst-1-ene-3-one

To a stirred suspension of 43 g of S-(2-pyridyl)-3-oxo-4-aza-5-alpha-androst-1-ene-17-beta-thiocarboxylate in 500 ml of anhydrous tetrahydrofuran (THF) was added at −78° C. a THF solution of 157 ml of 2N phenylmagnesium chloride over 60 minutes. After stirring at −78° C. for 60 minutes, the mixture was brought to −30° C. and was quenched by addition of 10% HCl while maintaining the temperature below −20° C. After warming to 0° C., the mixture was diluted with 2000 ml of water and extracted with 4000 ml of dichloromethane in portions. The organic layer was washed sequentially with water, 1N sodium hydroxide, water and saturated sodium chloride solution. Drying with MgSO4 and concentration afforded 37.5 g of crude product. Recrystallization from dichloromethane/ethyl acetate gave the title phenyl ketone (30.4 g, 77% yield). m.p. 290–291° C.

|   | Calc | Found |
|---|---|---|
| N | 3.61 | 3.56 |
| C | 77.48 | 77.16 |
| H | 8.26 | 8.19 |

Example 6
17-beta-4-fluorophenycarbonyl-4-aza-5-alpha-androst-1-ene-3-one

The procedure of Example 5 was repeated except using p-fluorophenylmagnesium bromide as the Grignard reagent and the title compound was obtained. m.p. 315–315.5° C.

Example 7
17β-(cyclohexylcarbonyl)-4-aza-5α-androst-1-ene-3-one

To a suspension of 34.8 g of the thiopyridyl ester of Example 2 in 700 ml of anhydrous THF was added at −65 degrees C. 130 ml of a 2 M ether solution of cyclohexyl magnesium chloride over a period of 20 minutes. After stirring at −70 degrees C. for 60 minutes the solution was warmed and stirred at −10 degrees C. for 60 minutes. The mixture was diluted with 500 ml of dichloromethane and then dropwise with dichloromethane, the phases were separated and the organic layer was treated sequentially with water, 1 N sodium hydroxide, water and saturated sodium chloride solution. The organic solution was decolorized with charcoal, filtered and concentrated to a residue which was crystallized from ethyl acetate to give 28.2 of the title compound, m.p. 271.5–277 degrees C.

Example 8

The title compound of Example 7 was also prepared by the following procedure.

To a mixture of 150 g of methyl 3-oxo-4-aza-5-alpha-androst-1-ene-17-beta-carboxylate in 2800 ml of anhydrous THF was added with stirring at less than 0 degrees C. internal temperature 678 ml of a 2 N ether solution of cyclohexyl magnesium chloride. The solution was then refluxed for 6 hours. The cooled (less than 10 degrees C.) reaction mixture was acidified with 10% HCl solution and was extracted with dichloromethane. The organic layer was washed sequentially with water, saturated NaHCO3 solution and saturated NaCl solution. Drying (MgSO4) and evaporation left 163 g of crude cyclohexyl ketone. Recrystallization from dichloromethane/ethylacetate gave 131 g of the pure material.

m.p. 269–270 degrees C.

|   | % Calc. | Found |
|---|---------|-------|
| N | 3.61    | 3.61  |
| C | 77.37   | 77.37 |
| H | 9.74    | 10.13 |

Example 9

17-beta-(cyclopentylcarbonyl)-4-aza-5-alpha-androst-1-ene-3-one

When the procedure of Example 7 or 8 was repeated using cyclopentylmagnesium chloride, the title compound was obtained:

m.p. 272–273 degrees C.

|   | Calc. | Found |
|---|-------|-------|
| N | 3.66  | 3.78  |
| C | 75.25 | 74.89 |
| H | 9.60  | 9.54  |

Example 10

17-beta-(cyclobutylcarbonyl)-4-aza-5-alpha-androst-1-ene-3-one

When the procedure of Example 7 or 8 was repeated using cyclobutylmagnesium chloride, the title compound was obtained:

m.p. 288–289 degrees C.

|   | % Calc | Found |
|---|--------|-------|
| N | 3.94   | 3.87  |
| C | 77.71  | 78.06 |
| H | 9.36   | 9.61  |

Example 11

Synthesis of 17-β-(4-Phenylbenzoyl)-4-aza-5α-androst-1-en-3-one

To a suspension of 258.0 mg of dry activated magnesium chips in 5.0 ml of dry THF was added 932.0 mg of 4-bromobiphenyl in 5.0 ml of dry THF under $N_2$. The reaction was run in an ultrasonic bath at a temperature range of 24–30° C. To the well-agitated mixture was added dropwise 30 μl of 1,2-dibromoethane/$N_2$. The reaction was allowed to proceed for 1–1½ hours at 28° C./$N_2$. The concentration of the Grignard reagent was 4.0 mmoles in 10.0 ml of dry THF.

The steroid from Example 2 (205.0 mg, 0.5 mmol of thiopyridyl ester) was suspended in 2.0 ml of dry THF, cooled to −80° C. and the above Grignard 3.80 ml was added via syringe to the steroidal suspension over 5–10 minutes/$N_2$. The reaction was allowed to proceed for 1 hour at −80° C./$N_2$ and then at −10° C. for an additional hour/$N_2$. The solution was diluted with 10.0 ml of methylene chloride and quenched with saturated aqueous solution of $NH_4Cl$ to pH=4. The organic layers were separated, washed 3 times with water, 3 times with saturated sodium chloride, dried over $MgSO_4$, filtered, and evaporated under vacuum to afford 156.2 mg of crude product. Crystallization from EtOAc gave the above-titled product in 98.58 mg, m.pt. 290° C.–290.5° C.

Anald. Calcd. for $C_{31}H_{35}NO_2$: C,82.08; H,7.78; N,3.09; Found: C,81.84; H,8.01; N,3.06. FAB: Calc. for $C_{31}H_{35}NO_2$: 453; Found: 453.

Example 12

17-β-(3-Phenylbenzoyl)-4-aza-5α-androst-1-en-3-one

To a suspension of 258.0 mg of dry activated magnesium chips in 8.0 ml of dry THF was added 932.0 mg of 3-bromobiphenyl in 2.0 ml of dry THF under $N_2$. The reaction was run in an ultrasonic bath at a temperature range of 24–30° C. To the well-agitated mixture was added dropwise 30 microliters of 1,2-dibromoethane/$N_2$. The concentration of the Grignard reagent was 4 mmoles in 10.0 ml of dry THF.

The steroid from Example 2, 205.0 mg (0.5 mmoles) was suspended in 2.0 ml of dry THF, cooled to −80° C. and the above prepared Grignard, 3.80 ml, was added via syringe to the steroidal suspension over 5–10 minutes/$N_2$. The reaction was allowed to proceed for 1 hour at −80° C./$N_2$ and then at −10° C. for an additional hour/$N_2$. The solution was diluted with 10.0 ml of methylene chloride and quenched with a saturated aqueous solution of $NH_4Cl$ to pH=4. The organic layers were separated, washed 3 times with water, 3 times with saturated sodium chloride, dried over $MgSO_4$, filtered, and evaporated under vacuum. Crystallization from ethyl acetate afforded 122.84 mg of product. The material was purified on 20.0 g of silica gel column using 70:30 ($CHCl_3$-acetone) as eluant, to give a single spot material 117.0 mg of the above-titled compound, m.pt. 184–185° C.

Anald. Calcd. for $C_{31}H_{35}NO_2$: C,82,08; H,7.78; N,3.09; Found: C,82.28; H,8.04; N,2.98. FAB: Calcd. for $C_{31}H_{35}NO_2$: 453; Found: 453.

Example 13
Synthesis of 17-β-(4-Methylthiobenzoyl)-4-aza-5-α-androst-1-en-3-one To a suspension of 250.0 mg of dry activated magnesium chips in 8.0 ml of dry THF was added 812.0 mg of p-bromophenyl methyl sulfide in 3.0 ml of dry THF under $N_2$. The reaction was run in an ultrasonic bath at a temperature range of 24–30° C. To the well-agitated mixture was added dropwise 40 µl of 1,2-dibromoethane/$N_2$. The reaction was allowed to proceed for 1 to 1½ hours at 28° C./$N_2$. The concentration of the Grignard reagent was 4.0 mmoles in 10 ml of dry THF.

The steroid from Example 2, i.e. the pyridylthio ester, 205 mg, was suspended in 2.0 ml of dry THF, cooled to -80° C. and the above prepared Grignard was added via syringe to the steroidal suspension in 5–10 minutes/$N_2$. The reaction was allowed to proceed for 1 hour at -80° C./$N_2$ and then at -10° C. for an additional hour/$N_2$. The solution was diluted with 10.0 ml of methylene chloride, and quenched with saturated aqueous solution of $NH_4Cl$ to pH=4. The organic layers were separated, washed 3 times with water; 3 times with saturated sodium chloride, dried over $MgSO_4$, filtered, and evaporated under vacuum to afford 105.0 mg of crude product.

The crude product was chromatographed on TLC (one plate, 20 cm×20 cm×20 cm×1000 µm silica gel) eluted with 80:20 ($CH_2Cl_2$-acetone) to afford 66.0 mg of single spot material. Crystallization from EtOAc afforded 45.0 mg of the above-titled compound, m.pt. 286–287° C.

FAB for $C_{26}H_{33}NO_2S$ (Calcd.) 424; Found 424.

Example 14
Synthesis of 17-β-(4-methylsulfinylbenzoyl) and -(4-methylsulfonylbenzoyl)-4-aza-5α-androst-1-en-3-one A. Oxidation 19.91 mg of the methylthio product from Example 13 was dissolved in 2.5 ml of $CH_2Cl_2$, cooled to 0–(-2)° C. and was treated with a solution 9.6 mg of m-chloroperbenzoic acid in 1.0 ml of $CH_2Cl_2$ over a period of 4 minutes. After stirring for 1 hour at 0–(-2)° C., the reaction was diluted with 10 ml. $CH_2Cl_2$. The layers were washed subsequently with 2.5% $NaHCO_3$, $H_2O$ and saturated NaCl solutions. The organic layer was dried over $MgSO_4$ overnight, filtered and evaporated in vacuo to yield 17 mg product. Crystallization from EtOAc gave 11.8 mg of the above-titled compound, a solid, mp. 313–313.5° C. (with dec.).

Anal. Calcd. for $C_{26}H_{33}NO_3S.1/4H_2O$: C,70.31; H,7.60; N,3.15; Found: C,70.47; H,7.70; N,3.00. FAB for $C_{26}H_{33}NO_3S$ (Calcd. 440); Found 440.

Sulfone

Fifteen percent (15%) of the corresponding sulfone, 17β-(4-methylsulfonyl benzoyl) derivative, was isolated by chromatography from the reaction as a byproduct. Recrystallized from EtOAc to yield a solid, mp. 279–279.5° C. Molecular weight by FAB showed 456; calculated 456.

Anal. for $C_{26}H_{33}NO_4S.0.25 H_2O$ Calc: C,67.87; H,7.28; N,3.04. Found: C,67.96; H,6.72; N,2.95.

Example 15
Synthesis of 17-β-(4-acetoxymethylthiobenzoyl)-4-aza-5α-androst-1-en-3-one Trifluoroacetic anhydride (165 µl) was dissolved in 780 µl of acetic anhydride and kept for 5 hours at room temperature (RT).

To 300 µl of the above solution of mixed anhydrides was added 34.15 mg pure sulfoxide from Example 14 with stirring. A few minutes later 54.0 µl of 2,6-lutidine was added and the reaction was allowed to stir at RT/$N_2$ for 17 hours.

The liquid anhydrides were removed under reduced pressure and the remaining residue extracted (4 times with $CHCl_3$). The $CHCl_3$ extracts were washed subsequently with dilute HCl; 5% $NaHCO_3$ solution, 3 times; 3 times with $H_2O$; and finally with saturated NaCl solution, and then dried over $MgSO_4$ filtered and evaporated the solution to dryness in vacuo to yield 42.1 mg of crude product.

The crude product from Step A was purified by chromatography on silica gel using 95:5 ($CHCl_3$-acetone) as eluant and then crystallizing the obtained solid from EtOAc to yield 17.8 mg of the above-titled compound as crystals, m.pt. 235–236° C. (dec.).

Anal. Calcd. for $C_{28}H_{35}O_4NS.1/4 H_2O$: C,68.57; H,7.40; N,2.86; Found: C,69.02; H,7.39; N,2.73. FAB for $C_{28}H_{28}O_4NS$ calcd.: 482; Found 482. The NMR (proton) was in agreement with the assigned product structure.

Example 16
Synthesis of 17β(4-mercaptobenzoyl)-4-aza-5α-androst-1-en-3 one 40.0 mg of the acetoxy-methyl-thio derivative from Example 15 was suspended in 3.0 ml of isopropanol. The reaction mixture was flushed several times with $N_2$, and with vacuum, and the system kept under nitrogen atmosphere. To the above mixture was added 40.0 mg of $K_2CO_3$ in 2.00 ml of water (free of oxygen) via syringe, and the temperature of the reaction mixture was allowed to rise to 80° C. under gentle reflux under slight vacuum for 10 minutes, and then under $N_2$ for 1 hour. After 1 hour, the reaction mixture was a clear yellow solution. It was brought to R.T., cooled to 0–5° C. and quenched with 2.5 N HCl acid/$N_2$. The reaction mixture was extracted 4 times with $CH_2Cl_2$. The organic layer was washed with $H_2O$ 4 times; 3 times with saturated salt solution, and finally dried over $MgSO_4$. Filtered and evaporated to dryness in vacuo to yield 36.9 mg of crude product. The crude product was dissolved in 2.0 ml of $CHCl_3$, filtered through Teflon (Acrodisc CR) and purified by preparative HPLC on silica gel and eluted with 60:40 ($CH_2Cl_2$-acetone). Crystallization, from EtOAc afforded a single spot material, 20.7 mg of the above-titled compound, m.pt. 285–286° C.

Anal. Calcd. for $C_{25}H_{31}O_2NS.1/2 H_2O$: C,72.19; H,7.69; N,3.24; Found: C,71.82; H,7.43; N,3.26. FAB: Calcd. for $C_{25}H_{31}O_2NS$: 410; Found: 410.

Example 17
Synthesis of 17-β-(4-Dimethylaminobenzoyl)-4-aza-5-α-androst-1-en-3-one To a suspension of 291.0 mg of dry activated magnesium chips in 8.0 ml of dry THF was added 800.0 mg of 4-bromo-N,N-dimethylaniline in 2.0 ml of dry THF under $N_2$. The reaction was run in an ultrasonic bath at a temperature range of 24–30° C. To the well-agitated mixture was added dropwise 30 µl of 1,2-dibromoethane/$N_2$. The reaction was allowed to proceed for 1 to 1½ hours at 28° C./$N_2$. The concentration of the Grignard reagent was 4.0 mmoles in 10.0 ml of dry THF.

The steroid from Example 2 (205 mg of pyridyl thioester) was suspended in 2.0 ml of dry THF, cooled to -80° C. and the above Grignard 3.8 ml (3 equivalents) was added via syringe to the steroidal suspension over 5–10 minutes/$N_2$. The reaction was allowed to proceed for 1 hour at -80° C./$N_2$ and then at -10° C. for an additional hour/$N_2$. The solution was diluted with 10.0 ml of methylene chloride and quenched with a saturated aqueous solution of $NH_4Cl$ to pH=4. The organic layers were separated, washed 3 times with water 3 times with saturated sodium chloride, dried over $MgSO_4$, filtered, and evaporated under vacuum to afford 151.3 mg of crude product. Crystallization from ethyl acetate gave 124.5 mg of the above-titled compound, m.pt. 268.5–269° C.

FAB: Calcd. $C_{27}H_{36}N_2O_2$: 421; Found: 421. The NMR (proton in $CDCl_3$) confirmed the assigned structure.

Example 18
General Procedure for Preparing Protected Silyl Derivatives 1.0 mole of phenol or its derivatives, or 1 mole of alcohol is treated with 1.5 liters of dry methylene chloride. To the clear solution is added dry 3.0 moles of imidazole/$N_2$. The clear solution is cooled to 0° C./$N_2$, and 2.0 moles of t-butyl dimethyl chlorosilane in 300.0 ml of dry methylene chloride is added dropwise at 0° C./$N_2$. Towards the end of the addition, precipitation occurs. The ice bath is removed, and the reaction is allowed to proceed overnight at R.T./$N_2$. Filter, wash the cake with cold $CH_2Cl_2$ solution, and the solvent is evaporated in vacuo to afford crude product. The crude product was readily purified by filtering through a silica gel column. (1 gr. of crude product per 100 g of silica gel, using $CH_2Cl_2$ as eluant) This method gives about 99% of pure silyl derivatives of phenols and alcohols.

Example 19
Synthesis of 17-β-(4-Hydroxybenzoyl)-4-aza-5-α-androst-1-ene-3-one
A. Grignard Reaction To a suspension of 1.22 g of dry activated magnesium chips in 20.0 ml of dry THF was added 5.6 g of 1-bromo-4-(tertiary-butyl dimethyl silyloxy)benzene (prepared from p-bromophenol by the General Procedure detailed above) in 10.0 ml of THF under $N_2$. The reaction was run in an ultrasonic bath at a temperature range of 24–30° C. To the well-agitated mixture was added dropwise 150 μl–200 μl of 1,2-dibromoethane/$N_2$. The reaction was allowed to proceed for 1–1½ hours at 28° C./$N_2$. The concentration of the Grignard reagent formed was 19.5 mmoles in 30.0 ml of dry THF.

The steroid from Example 2 (1.02 g, 2.49 mmoles) was suspended in 20.0 ml of dry THF, cooled to −80° C. and the above-prepared Grignard (11.5 ml) was added via syringe to the steroidal suspension in 5–10 minutes/$N_2$. The reaction was allowed to proceed for 1 hour at −80° C./$N_2$, and then at −10° C. for an additional hour/$N_2$. The reaction solution was diluted with 10.0 ml of methylene chloride and quenched with a saturated aqueous solution of $NH_4Cl$ to pH=4. Organic layers were separated, washed 3 times with $H_2O$, 3 times with saturated sodium chloride, dried over $MgSO_4$, filtered, and evaporated under a vacuum to a yellow color solid. Crystallization from ethyl acetate afforded 607 mg of product m.p. 248–249° C.

Anal. Calcd. for $C_{31}H_{45}O_3NSi$: C,73.32; H,8.93; N,2.75 Found: C,73.27; H,8.99; N,2.75. FAB: Found 508; Calc. 508.
B. Desilylation Dissolved 1.3 g of product from above step A in 20.0 ml of dry THF. Cooled to −5° C. and added 437 μl of glacial acetic acid/$N_2$. To the cold solution at −5° C. was added via syringe 3.0 ml tetra-n-butylammonium fluoride dropwise under $N_2$ atmosphere. Allowed the reaction to proceed under stirring for 1½–2 hours at 0° to −5° C./$N_2$. The reaction mixture was poured into a 2-layer mixture of ethyl acetate/sodium bicarbonate saturated solution at 0° C. The water layer was separated and further extracted with EtOAc 3 times and with $CH_2Cl_2$ (3 times).

The organic layers were combined, washed 3 times with $H_2O$, 1 time with saturated sodium chloride solution, and dried over $MgSO_4$, filtered and evaporated to dryness under vacuum. The crude product was crystallized from ethyl acetate to afford 977.9 mg, and further recrystallized from methanol to afford 842.3 mg of the above-titled product, m.pt. 296–297° C.

Anal. Calcd. for $C_{25}H_{31}NO_3.1/3$ $H_2O$: C,75.15; H,7.98; N,3.51. Found: C,75.13; H,7.76; N,3.54. (Mass Spec.) FAB: Found 394; Calcd. 394.

Example 20
17-β-(3,5-dimethyl-4-hydroxybenzoyl)-4-aza-5α-androst-1-ene-3-one
A. Preparation of Grignard Reagent To a suspension of 260.0 mg of dry activated magnesium chips in 6.0 ml of dry THF was added 628.0 mg of 1-bromo-3,5-dimethyl-4-tertiary-butyl-dimethylsilyloxybenzene (prepared from 4-bromo-2,6-dimethylphenol by the General Procedure described above) in 4.0 ml of THF/$N_2$. The reaction was conducted in an ultrasonic bath at a temperature range of 24° C.–30° C. To the well-agitated mixture was added dropwise 40 μl of 1,2-dibromoethane/$N_2$. The reaction was allowed to proceed for 2 hours/$N_2$. The concentration of the Grignard reagent thus formed was 2 mmoles in 10.0 ml of dry THF.

The steroid from Example 2 (205.0 mg (0.5 mmoles) was suspended in 3.0 ml of dry THF, cooled to −80° C., and 7.5 ml (1.50 millieq.) of the above-prepared Grignard was introduced via syringe to the steroidal suspension over a period of 5–10 minutes/$N_2$. The reaction was allowed to proceed for 1 hour at −80° C./$N_2$ and then at −10° C. for additional hour/$N_2$.

The reaction was quenched with 1N HCl, and then diluted with chloroform. The organic layers were combined, washed 3 times with $H_2O$, 3 times with saturated sodium chloride and dried over $MgSO_4$, filtered and concentrated in vacuo. The crude residue was washed with ether to afford 121.7 mg of product.

The crude product was dissolved in 70:30 ($CHCl_3$-acetone), filtered through Teflon (Acrodisc CR) and purified by preparative HPLC (Waters Prep-pak) on silica gel and eluted with 70:30 ($CHCl_3$-acetone).

The major component was recrystallized from ethyl acetate to give 52.0 mg of product m.pt 245–245.5° C.

Anal. Calcd. for $C_{33}H_{49}O_3NSi$: C,73.96; H,9.23; N,2.61; Found: C,74.06; H,9.33: N,2.64; (Mass Spec.) FAB: Found: 536; Calc.: 536
B. Deblocking the Silyl Derivative Dissolved 54.0 mg of the above product from A in dry THF (1.3 ml). The clear solution was cooled to 0° C., and 29 μl of glacial HOAc was added via syringe/$N_2$. To the above solution was added dropwise 172 μl of tetra-n-butylammonium fluoride at 0° C. dropwise via syringe/$N_2$. Allowed the reaction to proceed at 0° C./$N_2$ for 1½ hours. The reaction mixture was poured into ice/saturated $NaHCO_3$ solution and EtOAc. Stirred for several minutes. Allow the layers to separate, and the $H_2O$ layer was extracted 3 times with EtOAc and 3 times with $CHCl_3$.

Combined the organic layers and washed 3 times with $H_2O$, then 3 times with saturated NaCl, and then dried over $MgSO_4$, filtered and evaporated to dryness in vacuum to afford 52.2 mg.

The product was crystallized from EtOAc to give 22.5 mg of the above-titled product m.pt 305–306° C.

Calc. for $C_{27}H_{35}O_3N.H_2O$: C, 73.77; H, 8.49; N, 3.10. Found: C, 73.62; H, 7.90; N, 3.44. (Mass Spec.) FAB: Calc: 422; Found: 422

Example 21
Synthesis of 17-β-(4-Methoxybenzoyl)-4-aza-5-α-androst-1-ene-3-one

A. Grignard Reaction

To a suspension of 258.0 mg of dry activated Mg chips in 8.0 ml of $THF/N_2$ was added 748.0 mg p-bromoanisole in 2.0 ml of dry THF. The reaction was run in an ultrasonic bath at a temperature range of 24–30° C./$N_2$. To the well-agitated mixture was added dropwise 30.0 μl of 1,2-dibromoethane as a catalyst. The reaction was allowed to progress for 1–2 hours at 28° C. The formed Grignard reagent had a concentration of 4 mmoles in 10.0 μl of dry THF.

The steroid from Example 2 (205.0 mg (0.50 mml) was suspended in 2.0 ml of THF, cooled to −78° C. and the above-prepared Grignard reagent (3.75 ml; 14 milliequivalents) was added via syringe to the steroidal suspension over 5–10 minutes/$N_2$ and then at −10° C. for an additional hour/$N_2$. The resulting reaction mixture was a clear solution, which was cooled to 0–5° C., diluted with chloroform and quenched with 1N HCl acid. The organic layers were separated, washed with $H_2O$ 2 times, followed with saturated NaCl solution, dried over $MgSO_4$, filtered and evaporated in vacuo. The crude product was washed with ether, and crystallized from EtOAc to give 110 mg of product m.pt 305–306° C.

Further purification was carried out by chromatographic isolation on a TLC. plate, (20 cm×20 cm×1000 μm), using as eluant, 70:30 ($CHCl_3$: acetone). Recrystallization from EtOAc yielded 78.56 mg of the above-titled product, m.pt 305–306° C. (dec.).

(Mass Spec) FAB: Calcd.,408; Found 408.

Example 22
Synthesis of 17-β-(3-hydroxybenzoyl)-4-aza-5α-androst-1-ene-3 one

A. Preparation of Grignard Reagent

To a suspension of 230.0 mg of dry activated Mg chips in 2.0 ml of dry THF was added 722.4 mg of 1-bromo-3-tertiary-butyl dimethyl-silyloxybenzene (prepared from 3-bromophenol by the General Procedure described above) in 8.0 ml of dry $THF/N_2$. The reaction was run in an ultrasonic bath at a temperature range of 24–30° C./$N_2$. To the well-agitated mixture was added dropwise 20.0 μl of 1,2-dibromoethane/$N_2$. Allowed the reaction to progress for 2½ hours at 28° C./$N_2$. The formed Grignard reagent had a concentration of 2.52 mmoles in 10.0 ml of dry THF.

The steroid from Example 2 (205.0 mg (0.5 mmoles) was suspended in 2.0 ml of THF, cooled to −78° C. and the above-prepared Grignard reagent (6.0 ml, (1.5 milliequivalents) was added via syringe to the steroidal suspension over 5–10 minutes/$N_2$, and then stirred for an additional hour at −10° C./$N_2$. The clear reaction mixture was quenched at 0 to −5° C. with 1N HCl acid for 10.0 minutes and diluted with $CHCl_3$. The combined organic layers were washed 3 times with $H_2O$, 3 times with saturated NaCl, and then dried over $MgSO_4$, filtered and concentrated in vacuo to afford crude product. The product was purified on silica gel column and was eluted with 70:30 ($CHCl_3$-acetone). The desired product amounted to 58.0 mg, as the silyl derivative, 17β-(3-tertiary-butyldimethylsilyloxybenzoyl)-4-methyl-4-aza-5α-androst-1-en-3-one.

B. Deblocking 57.6 mg of the above silyl derivative was dissolved in 3.0 ml of dry THF. The solution was cooled to 0° C., and 20 μl of glacial acetic acid was introduced via syringe. To the clear solution was added 130.0 μl of (n-butyl)$_4$NF via syringe, and allowed the reaction to proceed for 1 hour/$N_2$ at 0° C. The reaction mixture was poured into EtOAc/$NaHCO_3$ sat. solution @ 0° C. The water layer was separated, extracted 3 times with EtOAc and then 3 times with chloroform. The organic layers were combined and washed 3 times with $H_2O$, 3 times with saturated NaCl solution, dried over $MgSO_4$, filtered and evaporated in vacuo to give 57.11 mg of crude product. The crude product was chromatographed by TLC (one plate, 20 cm×20 cm×250 μm silica gel), eluted with 70:30 ($CHCl_3$-acetone) to afford 44.5 mg of the above-titled product. Recrystallization from EtOAc gave 29.30 mg m.pt 279–280° C.

Anal. Calcl. for $C_{25}H_{31}NO_3$: 8$H_2O$: C,73.60; H,8.06; N,3.43. Found: C,73.26; H,8.22; N,3.28. (Mass Spec.) FAB: Calcd: 394; Found 394.

Example 23
Synthesis of 17-β-(4-hydroxymethyl-benzoyl)-4-aza-5α-androst-1-en-3-one

A. Preparation of Grignard solution

To a suspension of 100.0 mg (4 mmoles) of dry activated Mg chips in 5.0 ml of dry $THF/N_2$, was added 753.0 mg (2.5 moles) of 1-bromo-4-tertiary-butyl dimethyl silyloxy methyl benzene (prepared from 4-bromobenzyl alcohol by the General Procedure described above). The reaction was conducted in an ultrasonic bath at a temperature range of 24–30° C./$N_2$. To the well-agitated mixture was added 20 μl of 1,2-dibromoethane/$N_2$. Allowed the reaction to progress for 2 hours at 28° C./$N_2$. The concentration of formed Grignard was 2.5 mmoles in 5.0 ml of dry THF.

B. Grignard Reaction

The steroid from Example 2 (205.0 mg (0.5 mmoles) was suspended in 2.0 ml of THF, cooled to −78° C., and the above-prepared Grignard (3.0 ml, 3.75 milliequivalents) was introduced via syringe into the steroidal suspension over 5–10 minutes/$N_2$. Allowed the reaction to progress for 1 hour at −80° C./$N_2$, and then for an additional hour at −10° C./$N_2$. The clear reaction solution was quenched with saturated $NH_4Cl$ at 0° to −5° C., and then diluted with $CH_2Cl_2$. The organic layers were separated and washed 3 times with water, 3 times with saturated NaCl, dried over $MgSO_4$, filtered and evaporated in vacuo to dryness. Crude product was crystallized from EtOAc to give 137.8 mg of silyl product.

(Mass Spec.) FAB: Calcd for $C_{30}H_{41}O_3NSi$: 521.75 Found: 522.0.

C. Deblocking of Silyl Derivative

The product from Step B above (23.67 mg) was dissolved in 0.5 ml of THF and 0.5 ml of MeOH and cooled to 0° C./$N_2$. To the cold solution was added 10 μl of concentrated sulfuric acid (98%). The reaction was stirred for 45 minutes at 0° C./$N_2$. To the cold solution at 0° C. was slowly added a saturated solution of $NaHCO_3$ and chloroform. Extracted 3 times with $CHCl_3$. The organic layers were washed 3 times with water, 3 times with saturated NaCl, solution dried over $MgSO_4$, filtered and evaporated to dryness in vacuo, to afford 10.18 mg. After chromatography on a TLC plate (elution with 1:1 $CHCl_2$: acetone) The crude product was crystallized from EtOAc to give 6.0 mg of the above-titled product, m.pt 318–320° C.

Anal. Calcd. for $C_{26}H_{33}O_3N.1/3H_2O$: C,75.41: H,7.94; N,3.38. Found: C,75.61; H,7.84; N,3.12. (Mass Spec.) FAB: Calc.: 408; Found: 408

Example 24
Synthesis of 17-β-(4-Carboxybenzoyl)-4-aza-5α-androst-1-en-3-one

A. Oxidation 90.2 mg of the product from Example 23 was dissolved in 2.63 ml of glacial acetic acid and to the clear solution was added 69.0 mg of $CrO_3$ (previously dried over $P_2O_5$ at R.T. for 2 days in vacuo). After stirring overnight, the reaction mixture was diluted with water and allowed to age overnight in the refrigerator. The reaction mixture was filtered and the mother liquor and washes were extracted overnight using a liquid-liquid extractor, ($H_2O$-EtOAc) under reflux conditions. The organic layer was dried over $MgSO_4$, filtered and evaporated in vacuo. The residue was dissolved in hot MeOH, filtered and evaporated in vacuo to afford a product weighing 32.0 mg.

FAB: Calc. for $C_{26}H_{31}O_4N$: 422.0; Found: 422.

B. Purification

The above free acid was purified by dissolving the above product in 1N sodium hydroxide solution. The clear solution was extracted 3 times with EtOAc. The aqueous basic solution was cooled and acidified with 1N HCl acid dropwise to pH=4 with stirring. The reaction mixture was allowed to age for 1 hour at 0° C. It was. filtered and the residue was washed with cold water. Dried overnight to 100° C. in vacuum <0.2 mm pressure.

Yield of the above-titled free acid was 9.85 mg. FAB: Calc. for $C_{25}H_{31}O_4N$: 422; Found 422. NMR analysis indicated the product to be an acid.

C. Sodium Salt of Above Acid 4.9 mg of the above product acid B was dissolved in 2.0 ml of hot methanol. To the clear solution, was added 11.6 μl of 1N NaOH(aq). To solution after methanol evaporation in vacuo, was added water to reach pH 7.21. The aqueous solution was freeze dried to give 6.3 mg of the sodium salt of the above-titled product.

Example 25

Synthesis of 17-β-(4-hydroxyethylbenzoyl)-4-aza-5α-androst-1-en-3-one

A. Grignard Reagent

To a suspension of 252 mg of dry activated Mg chips in 10.0 ml of dry THF was added 1.26 g (4 mmoles) of 1-bromo-4 tertiary-butyl dimethyl silyloxy ethyl benzene (prepared from 2-(p-bromophenyl) ethanol by the General Procedure described above). The reaction mixture was vigorously stirred using an ultrasonic vibrator/$N_2$. To the well-agitated mixture was added 40 μl of 1,2-dibromoethane to catalyze the above reaction. Allowed the reaction to progress for 3½–4 hours/$N_2$. The concentration of formed Grignard reagent was 4 mmoles in 10 ml of THF.

B. Grignard Reaction 205.0 mg (0.5 mmoles) of the aza-steroid of Example 2 was suspended in 2.0 ml of dry THF/$N_2$, cooled to −80° C., and the above-prepared Grignard (3.75 ml, 1.5 milliequivalents) via syringe was introduced into the steroidal suspension over 5–10 minutes/$N_2$. The reaction was run at −80° C. for 1 hour/$N_2$ and then for an additional hour at −10° C. The reaction was quenched with a saturated solution of $NH_4Cl$ at 0–5° C. and diluted with 10.0 ml of $CH_2Cl_2$. The organic layers were washed with water (3 times), saturated NaCl solution (3 times), dried with $MgSO_4$, filtered and evaporated in vacuo to dryness. The crude product was crystallized from EtOAc overnight to give 152.0 mg of product m.pt. 233–234° C.

Anal. Calcd. for $C_{33}H_{49}O_3NSi$:1/4 $H_2O$: C,73.55; H,9.18, N,2.59. Found: C,73.45; H,8.94; N,3.21 FAB: Calc. 536; Found 536

C. Desilylation 70.8 mg of product from Step B, was dissolved in 1.45 ml of methanol and 1.45 ml of THF. The solution was cooled to 0–5° C. and 29 μl of conc. $H_2SO_4$ was added via syringe under $N_2$. The reaction was allowed to proceed for 45 minutes/$N_2$. The reaction was carefully quenched at 0° C. with a saturated solution of $NaHCO_3$, and extracted 3 times with $CH_2Cl_2$. The organic layers were separated, washed with water (3 times), then with saturated NaCl solution, dried over $MgSO_4$, filtered and evaporated in vacuo to give 43.0 mg of crude product. The crude product was placed on a column of silica gel and was eluted with 1:1 acetone-$CH_2Cl_2$. The isolated product was crystallized from anhydrous methanol to afford 20.0 mg of the above-titled product m.pt 292–293° C. with dec.

Anal. Calcd. for $C_{27}H_{35}O_3N.1/4$ $H_2$: C,75.31; H,8.25; N,3.25. Found: C,75.49; H,8.29; N,3.45. FAB: Calcd 422; Found 422.

Example 26

Synthesis of 17-β-(4-carboxymethylbenzoyl)-4-aza-5α-androst-1-en-3-one

A. Oxidation 13.0 mg of the product from Example 25 was dissolved in 1 ml of glacial acetic acid. To the clear solution was added 10.0 mg of $CrO_3$ (previously dried over $P_2O_5$ in vacuum at R.T.). Allowed the reaction to progress overnight at R.T., and then at 0° C. for 48 hours. The addition of 7.0 ml of water caused the product to crystallize overnight in a refrigerator. The crude product was isolated, washed with cold water and dried in a vacuum at 110° C. below 1 mm pressure.

The dried crude product was dissolved in 1N sodium hydroxide and the basic solution was extracted 3 times with methylene chloride (The organic layers were separated, and the aqueous basic solution was cooled and acidified with 1.5 N hydrochloric acid. The precipitate was filtered, washed with water dried at 110° C. under vacuum at 0.1 mm pressure.

Yield of above-titled product=7.0 mg. FAB Calc. $C_{27}H_{33}O_4N$: 436; Found 436.

Example 27

Synthesis of 17-β-(3,4-dihydroxybenzoyl)-4-aza-5α-androst-1-en-3-one

A. Grignard

To a suspension of 258.5 mg of dry activated magnesium chips in 10.0 ml of dry THF, was added 482 mg. of 4-bromo-1,2-methylenedioxybenzene/$N_2$. (The starting material is commercially available from Aldrich Chemical) The reaction was conducted in an ultrasonic water bath at a temperature range of 24°–30° C. To the well-agitated mixture was added 40 μl of 1,2-dibromoethane as a catalyst/$N_2$, and the reaction was allowed to progress for 1½–2 hours at 28° C./$N_2$. The concentration of the formed Grignard reagent was 3.75 mmoles in 10 ml of dry THF.

The steroid from Example 2 (410 mg, 1 mmole) was suspended in 4.0 ml of dry THF/$N_2$ and cooled to −80° C. and 8.0 ml of the above-prepared Grignard (3.04 milliequivalents) was added via syringe to the steroidal suspension/$N_2$ over a period of 5–10 minutes. The reaction was allowed to proceed for 1 hour at −80° C., and then at −10° C. for an additional hour/$N_2$. The reaction mixture was diluted with $CH_2Cl_2$, and then quenched with 1N HCl at −5° C.

The organic layers were collected and washed with water 3 times, saturated NaCl solution 3 times, dried over $MgSO_4$, filtered and evaporated in vacuo to dryness. Purification of the crude product was carried out on 50.0 g of silica gel using as eluant 1:1($CH_2Cl_2$-acetone) to give 347.0 mg. FAB showed 422; Calcd. 422.

62.4 mg of the above product was crystallized from EtOAc to afford 11.39 mg of product m.pt.324–325° C.

Anal. Calcd. for $C_{26}H_{31}O_4N.3/4$ $H_2O$: C,71.78; H,7.53; N,3.22. Found: C,71.90; H,7.54; N,3.25. FAB for $C_{26}H_{31}O_4N$ showed 422; Calcd: 422.

B. Cleavage of Methylene Dioxylan Group 70.0 mg of the product from Step A was dissolved in dry 25.0 ml of 1,2-dichloroethane at R.T./$N_2$. The solution was allowed to cool to -10° C., and 1.03 ml of $BBr_3$ (1.0 M solution in dichloromethane) was added dropwise under $N_2$ atmosphere. The reaction was allowed to proceed at R.T. for 3½–4 hours/$N_2$. After 4 hours/$N_2$, the reaction was cooled to (-10° C.) and quenched with 10.0 ml of methanol for 10 minutes at 0° C., and then gradually the temperature was allowed to rise to R.T./$N_2$. The reaction mixture was evaporated in vacuo to dryness. The residue was extracted 3 times with EtOAc. The organic layers were washed with water 3 times, 2 times with saturated $NaHCO_3$ solution, 3 times with water and finally with a saturated solution of NaCl. The organic layers were dried over magnesium sulfate, filtered and concentrated in vacuo. The crude material was chromatographed on 2 silica gel plates, (20 cm×20 cm×20 cm×250 μm) eluted with 1:1 (acetone-methylene chloride). Recrystallization from EtOAc afforded 5.0 mg of the above-titled product m.p. 222–222.5° C.

Anal. Calcd. for $C_{25}H_{31}O_4N.1/2$ $H_2O$: C,71.78; H,7.66; N,3.35. Found: C,71.71; E,7.71; N,3.33. FAB: Calcd. for $C_{25}H_{31}O_4N$: 410; Found 410.

Example 28

Synthesis of 17-β-(2 methoxybenzoyl)-4-aza-5α-androst-1-ene-3-one

A. Grignard

To a suspension of 258.0 mg of dry activated magnesium chips in 8.0 ml of dry THF was added 771.0 mg of o-bromoanisole in 2.0 ml of dry THF/$N_2$. The reaction was conducted in an ultrasonic water bath at a temperature range of 24–30° C. To the well-agitated mixture was added 30 μl of 1,2-dibromoethane/$N_2$, and the reaction was allowed to progress for 2 hours at 28° C./$N_2$. The concentration of the formed Grignard reagent was 4 mmoles in 10.0 ml of dry THF.

The steroid from Example 2 (205 mg, 0.5 mmoles) was suspended in 2.0 ml of dry THF/$N_2$, cooled to -79° C., and 4.0 ml of the above-prepared Grignard (1.6 milli-equivalents) was added via syringe to the steroidal suspension/$N_2$ over a period of 5–10 minutes. The reaction mixture was allowed to proceed for 1 hour at -80° C., and then at 0–2° C. for an additional hour/$N_2$. The reaction mixture was diluted with $CH_2Cl_2$ and then quenched with 1N HCl solution at 0° C.

The organic layers were combined, washed 3 times with water, 3 times with saturated NaCl solution; and dried over $MgSO_4$. Filtered and evaporated in vacuum to dryness. The crude material was crystallized from EtOAc to give 124.5 mg of product m.pt 228–230° C. Purification on silica gel column using 70:30 ($CHCl_3$-acetone) gave a single spot material in a yield of 83.0 mg m.pt. 241–241.5.

Anal. Calcd. for $C_{26}H_{33}O_3N$: C,76.91; H,8.19; N,3.45 Found: C,76.36; H,8.26; N,3.35. FAB calcd. for $C_{26}H_{33}O_3N$: 406; Found: 406.

B. Cleavage of Methoxy Group 12.7 mg (0.03 mmoles) of the product from Step A was dissolved in 5.0 ml of dry methylene chloride/$N_2$. To clear solution at -79° C./N, was added 50 μl of 1 mmole/ml of $BBr_3$ in $CH_2Cl_2$ via syringe dropwise. Allowed the reaction to proceed at R.T. overnight/$N_2$ with rapid stirring. Next day, a clear yellow solution was obtained. The reaction mixture was cooled to 0–2° C. and quenched with water, to hydrolyze excess of $BBr_3$. The organic phase was washed 3 times with dilute sodium hydroxide, 3 times with water, 3 times with dilute HCl, 3 times with water, 3 times with saturated NaCl solution, and dried the organic layer over $MgSO_4$. Filtered, concentrated in a vacuum to dryness. The crude product crystallized from EtOAc to afford 7.0 mg of a pure single spot material being 17-β-(2-hydroxymethyl-benzoyl)-4-aza-5-α-androst-1-en-3-one.

FAB for $C_{25}H_{31}NO_2$; Calcd: 394; Found: 394.

Example 29

17β(α-hydroxybenzyl)-4-aza-5α-androst-1-ene-3-one 570 milligrams of 17β-benzoyl-4-aza-5α-androst-1-ene-3-one (prepared from the thiopyridyl ester of Example 2 and commercially available phenyl magnesium bromide, analogously via the procedure in Example 5, to produce the 17-benzoyl derivative, mp. 295–296° C. crystallized from EtOAc) was suspended in 80 ml of anhydrous isopropanol. To the suspension was added 500.0 mg of $NaBH_4$ in 5 portions. When all the hydride was added, 20.0 ml of dry THF was carefully added, so that the reaction mixture became a clear solution. Allowed the reaction to proceed at R.T./$N_2$ overnight. The reaction was quenched carefully with 1N HCl, and allowed to stir under $N_2$ for an additional hour at R.T. It was then diluted with water, and extracted 3 times with $CHCl_3$. The organic layers were combined, washed 3 times with $H_2O$; 3 times with saturated NaCl solution, and dried over $MgSO_4$. Filtered and evaporated to a white solid weighing 495.0 mg.

The crude material was crystallized from EtOAc to afford 349.5 mg of material. Further purification on a silica gel column, using as eluant, 70:30 ($CHCl_3$-acetone) gave a single spot material, 221 mg, of the above-titled compound, m.pt 296–297° C.

Anal. Calcd. for $C_{25}H_{33}NO_2$: C,79.17; H,8.78; N,3.70. Found: C,79.24; H,8.85; N,3.48. FAB Calcd. for $C_{25}H_{33}NO_2$: 380; Found: 380.

Example 30

17β-hydroxymethyl-4aza-5α-androst-1-ene-3-one 500.0 mg of S-2-pyridyl-3-oxo-4-aza-5α-androst-1-ene-3 one (Example 2) was dissolved in 40.0 ml of dry THF at R.T./$N_2$. The solution was cooled to -78° C./$N_2$ and 5.5 ml of 1 M dibutyl aluminium hydride in THF was slowly added via syringe to the solution, with rapid stirring. Allowed the reaction to proceed at -76 to -78° C. for half an hour under $N_2$. The temperature was gradually brought to R.T. and the reaction mixture kept for 2–½ hours/$N_2$. The reaction was then quenched at 0° to 5° C. with 2N HCl acid, and then diluted with $CHCl_3$. The organic layers were separated, washed with $H_2O$ 3 times, then with saturated NaCl solution, and finally dried over $MgSO_2$. Filtered, and the organic phase was evaporated under vacuum to give 216.0 mg of crude product.

The crude product was chromatographed on 20.0 g of E.M. silica gel column, using 70:30($CHCl_3$-acetone) as eluant.

Yield of single spot material was 126.3 mg of the above-titled compound, m.pt. 271–271.5° C.

Calcd. for $C_{19}H_{29}O_2N$: FAB 304; Found 304. NMR in $CDCl_3$ confirmed the above structure.

Example 31

17β-Formyl-4-aza-5α-androst-1-ene-3-one

Into a 100.0 ml dry flask was placed 1.3 ml of oxalyl chloride (2 M in $CH_2Cl_2$) with 50.0 ml of dry $CH_2Cl_2/N_2$. The above solution was cooled to -78° C. and 338 μl of DMSO was added dropwise via syringe/$N_2$. The mixture was stirred at -78° C./$N_2$ for 30 minutes, and a solution of above-prepared alcohol from Example 15, i.e. 17β hydroxymethyl-4-aza-5α-androst-1-ene-3-one (256.9 mg in 15.0 ml of dry $CH_2Cl_2/N_2$ was added via syringe. The reaction was allowed to progress for one hour at −78° C./N$_2$. After an hour at −78° C., was added 1 ml of dry triethylamine at a rapid rate. Reaction was raised slowly to R.T./N$_2$ with stirring, the resulting yellow solution was then poured into 50.0 ml of cold water. The organic layers were washed with a saturated solution of NaHCO$_3$, and then with a saturated solution of NaCl. Dried over MgSO$_4$, evaporated the solvent under vacuum to give 172.4 mg of crude product. The crude product was chromatographed on 60.0 g silica gel column using 70.30 (CHCl$_3$-acetone), to give a single spot material. Crystallization from EtOAc afforded the above-titled compound, 37.7 mg, m.pt. 258–259° C.

Example 32

Synthesis of diastereoisomeric 17β(α-hydroxybenzyl)-4-aza-5α-androst-1-ene-3-ones 26.3 of above-prepared formyl derivative from Example 31) was dissolved in 7.0 ml of dry THF/N$_2$. The solution was cooled to −78° C./N$_2$, and 131 μl of phenyl magnesium bromide (Aldrich reagent) 0.393 milliequivalents) in dry THF was added dropwise via syringe/N$_2$. Allowed the reaction to proceed for 1 hour/N$_2$ at −78° C. and then at R.T. for addition hour/N$_2$.

The reaction was quenched at 0–5° C. with 2.5N HCl, and then diluted with CHCl$_3$. Organic layers were separated, washed 3 times with water; 3 times with saturated NaCl solution, dried over MgSO$_4$. Filtered and evaporated in vacuum to dryness to afford 28.6 mg of crude product. Analysis of the NMR spectra and peak heights from HPLC indicated this product to be a 1:1 mixture of diastereoisomers. The crude product was filtered through a 1 μm Teflon filter and purified by HPLC on a Whitman Portisil 10 column using 70:30(CHCl$_3$-acetone). The FAB mass spectrum indicated the same M$^+$+1 for both isomers, being 380 mass units. The faster eluting isomer, m.pt. 289–289.5° C., was crystallized from EtOAc and showed a single spot material on TLC.

Anal. Calcd. for C$_{25}$H$_{33}$NO$_2$.1/4 H$_2$O; C,78.39; H,8.81; N,3.65. Found: C,78.11; H,8.65; N,3.58.

The slower eluting isomer, m.pt. 300–301° C. showed a single spot material on TLC. The faster isomer showed by NMR(CDCl$_3$): CH$_3$ at C-18 was deshielded (0.89δ) as compared to the slower isomer CH$_3$ at C-18 at (0.69δ). The benzilic proton for the faster isomer was also deshielded (4.5δ) versus (4.95δ). The olefinic proton at C-1 showed deshielding effects for the faster isomer at (6.81δ) to (6.62δ). From the above data, the two isomers showed distinctly different physical properties.

CHAPTER 3

Example 1

Preparation of 4-(2-(11-carboxyundecanoylamino)-phenoxy)butyric acid

Step A: Ethyl 4-(2-nitrophenoxy)butyrate(3)

To a stirred solution of 2-nitrophenol (1.4 g, 10 mM) and ethyl 4-brombbutyrate (2.1 g, 1.57 mL, 11 mM) in 35 mL of dry acetone is added 2 g (14.5 mM) of anhydrous, ground potassium carbonate. The resultant colored mixture is then heated under a nitrogen atmosphere at gentle reflux until the color due to the phenol anion has dissipated and a yellow mixture remains. Concentration of the cooled and filtered mixture yields an oil which on flash chromatography (silica gel, ethyl acetate/hexane or methylene chloride as eluant) yields 2.4 g (96% yield) of the title compound (3) as an oily liquid. When substituted ortho-nitrophenols are used in place of 2-nitrophenol in the above example, the corresponding substituted 2-nitrophenoxybutyrate is obtained.

Likewise, when ethyl 4-bromobutyrate is replaced by other halo esters the corresponding 2-nitrophenoxyalkanoate is obtained.

Step B: Ethyl 4-(2-aminophenoxy)butyrate (4)

A solution of 3 (1.27 g, 5.0 mM) in 15 mL ethyl acetate containing 200 mg of 5% palladium on carbon is reacted in a hydrogen atmosphere (40 psig.) at room temperature until hydrogen uptake ceases. The mixture is then filtered and concentrated in vacuo to yield 1.0+g of (4) as an oil/low melting solid.

Step C: 12-(Isopropylthio)dodecanoic acid (6)

A mixture of 12-bromododecanoic acid (5) (0.558 g, 2.0 mM) and sodium isopropylthiolate (1.1 g, 11.2 mM) in 1,2-dimethoxyethane (50 mL) was deaerated (N$_2$), heated to 85° C. (bath temperature), and kept at this temperature for 72 hours. The cooled mixture was filtered, the collected solid dissolved in water and filtered. The stirred solution was acidified with dilute hydrochloric acid, aged, filtered, the solid washed well with water and dried. There was obtained product 6 (0.54 g) as a white solid.

When other halo-acids are used in place of 12-bromododecanoic acid in the above example, the corresponding (isopropylthio)-acid is obtained.

Likewise, when other mercaptan salts are used in place of sodium isopropylthiolate in the above example, the corresponding (alkylthio)alkanoic acids are obtained.

Representative of, but not limited to, the acids obtained by this procedure are:

8-(Isopropylthio)octanoic acid
10-(Isopropylthio)decanoic acid
10-(Ethylthio)decanoic acid
11-(t-Butylthio)undecanoic acid
14-(n-Propylthio)tetradecanoic acid
9-(Methylthio)nonanoic acid Step D: Ethyl 4-(2-(12-(Isopropylthio)dodecanoylamino)-phenoxy)-butyrate (7)

To a solution of (4) (0.25 g, 1.14 mM) and (6) (0.274 g, 1.0 mM) in dry methylene chloride (10 mL) at room temperature was added 4-dimethylaminopyridine (0.122 g, 1.0 mM) followed within one minute by a solution of N,N'-dicyclohexylcarbodiimide (0.22 g, 1.06 mM) in methylene chloride (1 mL), 3×1 mL rinses with methylene chloride. After 2 days, the filtered mixture was concentrated in vacuo and the residue flash chromatographed on silica gel using 15–20% ethyl acetate in hexane as eluant to give product 7 (0.22 g) as an oil that solidified readily in a short time.

Step E 4-(2-(12-(Isopropylthio)dodecanoylamino) phenoxy)-butyric acid (8)

A stirred solution of ester (7) (0.124 g, 0.258 mM) in methanol (10 mL) was treated at room temperature under a nitrogen atmosphere with 2.5N sodium hydroxide solution (0.6 mL). Methanol (2×2 mL) was used to clear the mixture, and the reaction allowed to continue until TLC analysis showed no ester remained. The filtered mixture was concentrated in vacuo and the residue obtained stirred with water (30 mL). After aging, the mixture was filtered (The cake is the sodium salt of the product (100 mg), and the stirred filtrate acidified with dilute hydrochloric acid, aged, filtered, washed with water and dried to give product 8 (0.02 g) as a white solid. M.P. 82–84° C., with softening from 66° C.

Treatment of 8 with NaIO$_4$ as in Step J$_a$ will produce the corresponding sulfoxide, and treatment of 8 with m-chloroperbenzoic acid with Step J$_b$ will produce the corresponding sulfone.

Step F: 4-(2-(12-(Isopropylthio)dodecanoylamino)phenoxy)-butyramide (9)

To a stirred solution of (7) (20 mg, 0.041 mM) in methanol (10 mL) is added methanol saturated with ammonia (5 mL) and the stoppered mixture allowed to stir at ambient temperatures until TLC analysis shows little or no (D) remains. Concentration of the reaction mixture followed by preparative thin layer chromatography (silica gel; 3% methanol/methylene chloride as eluant) yields product 9 (11 mg) as a waxy solid.

Step G: Ethyl 4-(2-Amino-phenylthio)butyrate (11)

To a stirred deaerated ($N_2$) solution of 2-aminothiophenol (10) (1.25 g., 10 mM) and ethyl 4-bromobutyrate (2.14 g., 11 mM) in 40 mL. of dry 1,2-dimethoxyethane is added 8.3 g. of solid ground anhydrous potassium carbonate, the resultant mixture deaerated 3× under nitrogen and allowed to stir at room temperature until TLC analysis indicates the reaction is complete. The filtered mixture is then concentrated and the residue flash chromatographed on silica gel (85 g.) using 15% ethyl acetate/hexane as eluant to give 1.8 g. of (11) as a pale tan oil.

Step H: Ethyl 4-(2-(10-(Isopropylthio)decanoylamino)-phenylthio)butyrate (12)

When (11) and 10-(Isopropylthio)decanoic are reacted together analogously as per the conditions in Step (D) above, the title compound 12 is obtained.

Step I: 4-(2-(10-(Isopropylthio)decanoylamino)phenylthio)-butyric acid (13)

When (12) is hydrolyzed as per the conditions of Step (E) the title compound 13 is obtained.

Step J: 4-(2-(11-(ethylsulfinyl)undecanoylamino)phenoxy)-butyric acid

When the subject esters or acids are treated with sodium metaperiodate (Step $J_a$) in a suitable solvent (e.g. acetone/water) the corresponding sulfoxides are obtained. Treatment with meta-chloroperbenzoic acid (Step $J_b$) yields the corresponding sulfones. For example, when ethyl 4-(2-(11-(ethylthio)undecanoylamino)phenoxy)-butyrate 14 (0.045 g, 0.1 mM) in acetone (10 mL) is reacted with sodium metaperiodate (0.072 g, 0.33 mM) in water (2 mL) at room temperature the corresponding sulfoxide 15 is obtained. Hydrolysis as per Step (E) yields product 16 as an off-white solid. Additionally, treatment of 14 with m-chloroperbenzoic acid will produce the sulfone 17, which yields the acid 18 upon hydrolysis using the hydrolysis conditions of Step E.

The method of preparing the novel compounds of the present invention, already described above in general terms, may be further illustrated by the following examples which should not be construed as being limitations on the scope or spirit of the instant invention.

Example 1

Synthesis of 4-(2-(11-Carboxyundecyloxy)phenoxy)-butyric acid (7)

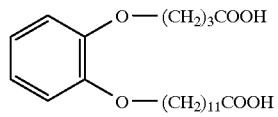

7

A. Ethyl 4-(2-Benzyloxyphenoxy)-butyrate (3)

To a stirred solution of 2-benzyloxyphenol (1) (4.0 g, 20 nM) and ethyl 4-bromobutyrate (2) (5.6 g, 28.7 mM) in dried acetone (100 mL) was added anhydrous ground potassium carbonate (6.0 g, 44 mM) and the resultant mixture heated at reflux under nitrogen until TLC analysis showed the absence of the starting phenol. Flash chromatography (silica gel, 15% ethyl acetate/hexane as eluant) of the filtered and concentrated mixture yielded 3.0 g of product (3) as a clear oil.

When the ethyl 4-bromobutyrate is replaced by haloesters in the above example, the corresponding ether-ester is obtained. Likewise, when the above phenol is replaced by other substituted 2-benzyloxyphenols, the corresponding 2-substituted ethers are obtained. Substitution of a 2-benzyloxy- or a 2-benzylthio-thiophenol for the 2-benzyloxyphenol yields the corresponding thioether-ester.

B. Ethyl 4-(2-Hydroxyphenoxy)-butyrate (4)

A mixture of (3) (1.57 g, 5.0 mM), ethanol (50 mL), glacial acetic acid (7 drops) and 10% palladium on carbon (0.7 g) was reacted in a hydrogen atmosphere (40 p.s.i.) at room temperature until hydrogen uptake ceased. Concentration of the filtered mixture yielded the product (4) as an oil.

C. Ethyl 4-(2-11-(Carbomethoxy)undecyloxyphenoxy) butyrate (6)

When (4) (0.224 g, 1.0 mM) and methyl 12-bromododecanoate (5) (0.32 g, 1.1 mM) were reacted with potassium carbonate in acetone as per Example (A), there was obtained product 6 (0.3 g) as a colorless oil.

When methyl 12-bromododecanoate is replaced by other halo esters in the above example, the corresponding diester is obtained.

D. 4-(2-(11-Carboxyundecyloxy)phenoxy)butyric acid (7)

To a stirred solution of (6) (0.102 g, 0.23 mM) in methanol (4 mL) and water (3 drops) was added 2.5 N sodium hydroxide solution (0.55 mL, 1.37 mM) dropwise, and the resultant mixture cleared with additional methanol (2 mL). When TLC analysis (2% methanol in methylene chloride (10 mL) containing glacial acetic acid (4 drops) indicated no mono- or diester remained, the methanol was removed in vacuo, the residue stirred with water (10 mL), and the solution filtered and acidified with 2N hydrochloric acid. Filtration of the resultant precipitate followed by washing with water and drying yielded product 7 (88 mg) as a white solid; M.P. collapses at 95° C., all melted at 105° C. (uncorr.; A.O. Spencer Hot Stage).

Calculated for $C_{22}H_{34}O_6$: C. 66.98; H. 8.69. Found: C. 67.32; H. 8.45.

Compounds (1)–(7) all had NMR and Mass Spectral data consistant with their assigned molecular formulas.

4-(2-(11-Carboxyndecyloxy)phenylsulfinyl)butyric acid (7B)

When the subject thioethers, e.g., Compound 7A in Flow Sheet C, as the ester or acid, are treated with sodium metaperoidate in a suitable solvent (e.g., acetone/water) the corresponding sulfoxides are obtained. Likewise, reaction of the subject thioethers with m-chloroperbenzoic acid yields the corresponding sulfones. For example, when 4-( 2-(11-carboxyundecyloxy)phenylthio butyric acid 7A (0.41 g, 1.0 mM) in acetone (25 mM) is reacted with sodium metaperiodate (0.72 g, 3.3 mM) in water at room temperature, the title sulfoxide 7B is obtained. When the same starting material in methylene chloride is reacted with excess m-chlorobenzoic acid, the corresponding sulfone is obtained.

Compounds (3)–(16) all had NMR and Mass Spectral data consistent with their assigned molecular structures.

Example 1

Preparation of 4-(2-(11-carboxyundecanoylamino)-phenoxy)butyric acid

Step A: Ethyl 4-(2-nitrophenoxy)butyrate (3)

To a stirred solution of 2-nitrophenol. (1) (1.4 g, 10 mM) and ethyl 4-bromobutyrate (2.1 g, 1.57 mL, 11 mM) in 35 mL of dry acetone is added 2 g (14.5 mM) of anhydrous, ground potassium carbonate. The resultant colored mixture is then heated under a nitrogen atmosphere at gentle reflux until the color due to the phenol anion has dissipated and a yellow mixture remains. Concentration of the cooled and filtered mixture yields an oil which on flash chromatography (silica gel, ethyl acetate/hexane- or methylene chloride as eluant) yields 2.4 g (96% yield) of the title compound (3) as an oily liquid.

Step B: Ethyl 4-(2-aminophenoxy)butyrate (4)

A solution of (3) (1.27 g, 5.0 mM) in 15 mL ethyl acetate containing 200 mg of 5% palladium on carbon is reacted in a hydrogen atmosphere (40 psig.) at room temperature until hydrogen uptake ceases. The mixture is then filtered and concentrated in vacuo to yield 1.0+g of (4) as an oil/low melting solid.

Step C: Dodecanedioic acid, mono methyl ester (6)

Diethyl dodecanedioate (5) (34.4 g, 0.12 M) is reacted with barium hydroxide octahydrate (19.2 g, 0.06 M) in methanol (240 mL) as per the analogous procedure of Org. Syn., Coll. Vol. III. p. 635 to yield 24.8 g of (6) as a white solid.

Step D: Dodecanedioic acid, mono methyl ester mono acid chloride (7)

A mixture of mono acid (6) (10.0 g, 0.041 M) and thionyl chloride (12.1 mL, 0.166 M) is refluxed for 5 hours, the excess thionyl chloride removed in vacuo, and the residual acid chloride repeatedly dissolved in dry benzene and concentrated until no thionyl chloride remains to yield 10.8 g of the title compound (7) as a waxy solid.

Step E: Ethyl 4-(2-(11-carbomethoxyundecanoylamino)-phenoxy)butyrate (8)

To a stirred, ice-cold solution of 0.89 g (4.0 mM) amine (4) and dried triethylamine (1.2 mL) in dry ether (40 mL) is added dropwise over ca. 4 minutes a solution of acid chloride (7) (1.04 g, 4.6 mM) in 20 mL of dry ether. The resultant mixture is allowed to stir cold for 20 minutes, and then at room temperature overnight. After filtering off the triethylamine hydrochloride, the ether filtrate is concentrated in vacuo and the residue chromatographed on an 82 g silica gel column using 20% ethyl acetate/hexane as eluant to give 1.49 g (85%) of (8) as a waxy solid.

The ether/triethylamine in the above reaction may be replaced by methylene chloride/pyridine with similar results. The same compound may also be prepared via direct coupling of acid (6) with the same amine using common coupling reagents, such as dicyclohexylcarbodiimide/N,N-dimethylaminopyridine, and the like.

Step F: 4-(2-(11-Carboxyundecanoylamino)phenoxy)-butyric acid (9)

To a stirred solution of (8) (1.0 g, 2.22 mM) in methanol (100 mL) is added 1 mL of water followed by dropwise addition of 2.5 N sodium hydroxide solution (4.0 mL). The walls of the reaction flask are rinsed down with 10 mL of methanol and the mixture is stirred under a nitrogen atmosphere until TLC analysis shows no ester (mono- or di-) remaining. The methanol is removed in vacuo, the residue taken up in 100 mL of water, stirred for solution, filtered (20 mL water rinses), and the stirred filtrate acidified dropwise with 2 N hydrochloric acid. Filtration of the resultant precipitate followed by copious water washing and drying gave 0.87 g (96%) of (9) as a chalk-like white solid. The compound was one component by TLC (silica gel, the eluant was 10 mL of 2% methanol in methylene chloride containing 4 drops of glacial acetic acid). mp 128.5–130° C. uncorr.

Microanalysis: Calc.: C, 64,84; H, 8.16; N, 3.44. Found: C, 64,90; H, 8.34; N, 3.33.

Step G: Ethyl 4-(2-Amino-3-methylphenylthio)butyrate (11)

To a stirred deaerated ($N_2$) solution of 2-aminothiophenol (10) (1.25 g., 10 mM) and ethyl 4-bromobutyrate (2.14 g., 11 mM) in 40 mL. of dry 1,2-dimethoxyethane is added 8.3 g. of solid ground anhydrous potassium carbonate, the resultant mixture deaerated 3× under nitrogen and allowed to stir at room temperature until TLC analysis indicates the reaction is complete. The filtered mixture is then concentrated and the residue flash chromatographed on silica gel (85 g.) using 15% ethyl acetate/hexane as eluant to give 1.8 g. of (11) as a pale tan oil.

Step H: 4-(2-(11-Carboxyundecanoylamino)phenylthio) butyric acid (13)

When amine (11) is acylated with acid chloride (7) as per procedure Step (E), and the resultant diester (ethyl 4-(2-(11-carbomethoxyundecanoylamino)phenylthio)butyrate 12 is hydrolyzed in Step I as per procedure (F), the title compound, 13 m.p. 113.5–115° C. is obtained.

The following representative compounds in this series were additionally made by the procedures outlined above:

14) 4-(2-(9-Carboxynonanoylamino)phenoxy)butyric acid, m.p. 121.5–124.5° C.
15) 4-(2-(10-Carboxydecanoylamino)phenoxy)butyric acid, m.p. 110–111.5° C.
16) 4-(2-(12-Carboxydodecanoylamino)phenoxy)butyric acid, m.p. 116–119° C.
17) 4-(2-(13-Carboxytridecanoylamino)phenoxy)butyric acid, m.p. 128–129.5° C.
18) 4-(2-(15-Carboxypentadecanoylamino)phenoxy)butyric acid, m.p. 121–125° C.
19) 5-(2-(11-Carboxyundecanoylamino)phenoxy)valeric acid, m.p. 112–113.5° C.
20) 4-(2-(11-Carboxyundecanoylamino)-3-methylphenoxy) butyric acid, m.p. 134.5–136.5° C.
21) 4-(2-(11-Carboxyundecanoylamino)-4-methylphenoxy) butyric acid, m.p. 99.5–100.5° C.
22) 4-(2-(11-Carboxyundecanoylamino)-5-methylphenoxy) butyric acid, m.p. 109.5–113° C.

Step J: Benzyl 2-Nitrophenyl Ether (23)

When 2-nitrophenol (1) is reacted with benzylbromide under the conditions of Step A the title ether (23) is obtained as a golden oil.

Step K: Benzyl 2-Aminophenyl Ether (24)

A solution of benzyl 2-nitrophenyl ether (23) (1.15 g., 5.0 mM) in ethanol (25 mL) saturated with anhydrous ammonia is stirred under a hydrogen atmosphere (40 p.s.i.) with Raney Nickel (2 g.) until TLC analysis indicates the absence of starting nitro compound. The filtered mixture is freed of excess ammonia by bubbling in anhydrous nitrogen. Removal of ethanol via vacuum distillation at room temperature yields 1.0 g. of title compound (24) as a deep colored crust, which was used as-is in the next reaction. This compound may also be obtained via careful reduction in ethanol or ethyl acetate using palladium on carbon as catalyst, but can be accompanied by slight,over-reduction if not monitored.

Step L: N-Trifluoroacetyl 2-Benzyloxvaniline (25)

To a stirred, near solution of amine (24) (5.0 mM) in dry diethyl ether (30 mL) is added anhydrous sodium carbonate (6.0 g., 57 mM) and the resultant mixture cooled in an ice-water bath. Trifluoroacetic anhydride (1.5 mL, 10.6 mM) is added dropwise to this cold mixture over 2 minutes, the color changing to a yellowish red. After 2 hours the cooling-bath is removed and the mixture allowed to stir at ambient temperatures overnight. After filtering, the filtrate is concentrated in vacuo and then pumped to yield 1.3 g. of the title compound (25) as a pale tan (with some reddish-brown color around the edges) crust.

Step M: N-Methyl-2-Benzyloxyaniline (27)

A well-stirred solution of (25) (0.295 g., 1.0 mM), methyl iodide (0.25 mL, 4.0 mM) and anhydrous acetone (5.0 ml) is set in an oil-bath previously heated to 59° C., and kept for 2 minutes. Powdered anhydrous potassium hydroxide (0.225 g., 4.0 mM) is added all at once, and the bath temperature allowed to rise to 65° C. Clumping-up of some of the KOH is observed. After 15 additional minutes, the reaction mixture is removed from the bath, allowed to cool, and the volatiles removed. Methanol (7 mL) is added with stirring to the residue of N-Methyl-N-trifluoroacetyl-2-benzyloxyaniline (26) obtained, followed by water (1 mL), and methanol (2 mL) (to wash down the sides). After stirring overnight at ambient temperatures, the methanol is removed in vacuo, the residue distributed between ether and water, separated, the organic layer washed with additional water, saturated sodium chloride solution, and dried over sodium sulfate. Concentration of the filtered ether solution gives the title compound (27) (0.212 g.) as an oil. NMR, MS, and TLC indicate little, if any, dimethyl compound.

Step N: N-(11-(Carbomethoxy)undecanoyl)-N-Methyl-2-Benzyloxyaniline (28)

To a stirred ice-cold solution of (27) (0.21 g., 1.0 mM) in dried methylene chloride (10 mL) containing anhydrous pyridine (0.3 mL) is added (7) (0.27 g., 1.03 mM), dissolved in 5 methylene chloride (5 mL), dropwise over 1 minute (some methylene chloride used as a rinse). After stirring cold for 30 minutes, the mixture is allowed to stir at ambient temperature for completion of the reaction. The reaction mixture is washed 1× with , 1N HCL, dried ($Na_2SO_4$) and filtered. Flash chromatography (silica gel, 20% ethyl acetate/ hexane as eluant) of the residue obtained gives the title compound (28) (0.33 g) as a colorless oil.

Step O: N-(11-(Carbomethoxy)undecanoyl)-N-Methyl-2-Hydroxy aniline (29)

A solution of (28) (0.11 g., 0.25 mM) in methanol (11 mL) containing 10% palladium on carbon (30 mg.) is shaken in a 40 p.s.i. hydrogen atmosphere until no (V) remained (TLC analysis). The filtered solution was then concentrated in vacuo to give the title compound (29), used immediately in step P.

Step P: Ethyl 4-(2-N-(11-Carbomethoxyundecanoyl)-N-(methyl)-amino)phenoxybutyrate (30)

To a stirred solution of (29) (0.087 g., 0.25 mM) and ethyl 4-bromobutyrate (0.115 mL, 0.80 mM) in anhydrous acetone (10 mL) is added anhydrous ground potassium carbonate (0.45 g., 3.2 mM) and the resultant mixture heated under gentle reflux under a nitrogen atmosphere for 24 hours. The mixture is cooled, filtered, and concentrated, and the residue flash chromatographed (silica gel; 20% ethyl acetate/ hexane eluant) to give 80 mg. of the title compound (30) as a colorless oil.

Step Q: 4-(2-N-(11-Carboxyundecanoyl)-N-(methyl)-amino)-phenoxybutyric Acid (31)

When (30) (0.055 g., 0.118 mM) is hydrolyzed as per its N-desmethyl analog (Step F, supra), and the resultant oil obtained after acidification is extracted with methylene chloride, there is obtained the title compound (31), (51 mg.), as a colorless oil.

Step R: Ethyl 4-(2-(11-Bromoundecanoylamino)phenoxy)-butyrate (32)

To a solution of (4) (2.60 g., 11 mM) and 11-bromoundecanoic acid (2.65 g., 10 mM) in anhydrous methylene chloride (90 mL) is added 4-(dimethylamino) pyridine (1.22 g., 10 mM) followed by N,N'-dicyclohexylcarbodiimide (2.3 g., 11 mM) (4×5 mL of methylenechloride rinses). Precipitation of dicyclohexylurea (DCU) begins within 4 minutes. When TLC analysis indicates the reaction is complete, the mixture is filtered, the filtrate concentrated in vacuo and the residue extracted with ether. The combined ether extracts are washed 1× with 1N hydrochloric acid, 1× saturated sodium chloride solution, dried ($Na_2SO_4$) and concentrated to a residue which is stirred, filtered, and concentrated alternately with ether and methylene chloride until all DCU is removed. Concentration of the final solution yields the title product (32) (2.35 g.) as an oil that goes readily to a waxy solid.

Attempted purification of an earlier run via column chromatography (silica gel;20% ethyl acetate/hexane as eluant) gave an impure product of greatly diminished yield.

Step S: Diethyl 10-(N-((2-(3-Carboethoxy)propyloxy)-phenyl)carboxamido)decylphosphonate (33)

A stirred mixture of (32) (0.235 g., 0.5 mM) and triethyl phosphite (TEP) (0.3 mL) is heated at 180° C. (bath temperature) under a nitrogen atmosphere for 8 hours, cooled, excess TEP removed in vacuo, and the residue flash chromatographed (Silica gel; ethyl acetate as eluant) to yield product 33 (0.13 g.) as a clear colorless oil.

Step T:

Cleavage of the phosphonate ester (33) using bromotrimethylsilane (procedure of J.C.S. Chem. Comm. p.739 (1979) yields 10-(N-((2-(3-(Carboethoxy)-propyloxy) phenyl carboxamido)decylphosphonic acid (34).

Step U:

Further hydrolysis of (34) using the procedure of Example (F) above yields the corresponding di-acid, 10-(N-((2-(3-Carboxy)propyloxy)phenyl)carboxamido)-decylphosphonic acid (35).

Step V: 10-(N-((2-(3-Carboethoxy)propyloxy)phenyl)-carboxamido)decaneisothiouronium bromide (36)

A stirred solution of (32) (0.047 g., 0.1 mM) in ethanol (2 mL) is reacted with thiourea (0.010 g., 0.13 mM) under the same conditions as (in Step W.). Concentration of the reaction mixture yields the title compound (36) (contaminated with a small amount of thiourea) which slowly solidifies in crystalline circles on standing. Stirring with dried chloroform followed by filtration and concentration yields the product as a thick wax.

Step W: Sodium 10-(N-((2-(3-Carboethoxy)propyloxy)-phenyl)carboxamido)decanethiosulfate (37)

To a stirred solution of (32) (0.047 g., 0.1 mM) in ethanol (2.0 mL) is added water (10 drops, slowly) followed by sodium thiosulfate (0.035 g., 0.14 mM), and the reaction mixture heated in an oil-bath (bath temperature ca. 90° C.) under a nitrogen atmosphere until TLC analysis indicated no starting bromo compound. The cooled mixture was then concentrated to remove the ethanol and water yielding a white crust. Extraction of this crust with chloroform, followed by filtration from inorganics, yielded product (37) (49 mg.) as a glaze which goes with time to a waxy solid. This product has appreciable water solubility.

Oxidation of (36) or (37) as per the analogous procedures in J. S. Showell et al., J. Org. Chem 27 (1962) 2853 or C. Ziegler et al J. Org. Chem. (1951) 621) yields the corresponding sulfonic acid (38).

Step X: Ethyl 4-(2-Nitropyrid-3-yloxy)butyrate (40)

This compound was prepared from ethyl 4-bromobutyrate 2 and 2-nitro-3-pyridinol (39) via the procedure of Step (A), supra. Following flash chromatography (silica gel; 1.5% methanol/methylene chloride eluant) a dilute sodium bicarbonate wash of an ether solution of the product was necessary to remove traces of starting phenol. The product (40) was obtained in 76% yield as a pale yelow oil.

Step Y: Ethyl 4-(2-Aminopyrid-3-yloxy)butyrate (41)

This compound was prepared via reduction of (40) as per the procedure of step (B), above. The amine (41) was obtained as a waxy solid.

Step Z: Ethyl 4-(2-(11-Carbomethoxyundecanoylamino) pyrid-3-yloxy)butyrate (42)

When (41) and (7) are reacted as per the procedure of step (E), above, the title compound (42) is obtained. Hydrolysis will yield the corresponding di-acid (4-(2-(11-Carboxyundecanoylamino)pyrid-3-yloxy)butyric acid (43).

Step AA: N-(11-Carbomethoxyundecanoyl)-2-hydroxyaniline (44)

To a stirred near solution of 2-aminophenol (0.24 g, 2.2 mM) in anhydrous methylene chloride (25 mL) was added dry pyridine (0.66 mL) and the mixture cooled in an ice-water bath. A solution of (7) (0.525 g, 2.0 mM) in methylene chloride (2 mL) was added over 1 minute (2×1.5 mL methylene chloride rinses), and the mixture allowed to stir cold. After 30 minutes the bath was removed. After stirring overnight at ambient temperatures, the mixture was filtered, the solvents removed in vacuo, and the residue pumped to remove all traces of pyridine. The product, (44) was used as is in subsequent steps.

Step BB: 4-(2-(11-Carbomethoxyundecanoylamino) phenoxy)-butyronitrile (45)

When (44) and 4-bromobutyronitrile are reacted under the conditions of step (A), above, (45) is obtained as a waxy solid. Conversely, reacting (44) with ethyl 4-bromobutyrate as in step (A) yields (8).

Step CC: 4-(2-(11-Carbomethoxyundecanoylamino) phenoxy)-butyramide (46)

To a stirred solution of (45) (11 mg, 0.027 mM) in methylene chloride (3 mL) is added activated manganese dioxide (100 mg) and the resultant suspension allowed to stir stoppered at room temperature. After a few days some additional methylene chloride and manganese dioxide (100 mg) are added and the reaction allowed to continue. This is repeated one additional time. When TLC analysis shows no nitrile remains the mixture is filtered, the catalyst washed well with fresh methylene chloride, and the filtrate concentrated to yield the title product, (46) as a waxy solid.

The above new isolated, purified compounds had NMR and Mass spectra consistent with their assigned chemical structures. All melting points were taken on an A.O. Spencer hot stage and are uncorrected.

CHAPTER 4

Example 1
17β-Benzoyl-Androst-3,5-diene-3-Carboxylic Acid

The title compound is made by reacting 17β-carbomethoxy-androst-3,5-diene-3-protected carboxylic acid in e.g., THF, with phenyl magnesium bromide under standard Grignard conditions. Standard workup procedure yields the title. compound, m.p.222–225° C.

Reference Example 1
Synthesis of 4-(4-isobutylbenzyloxy)-2,3-dimethylbenzaldehyde

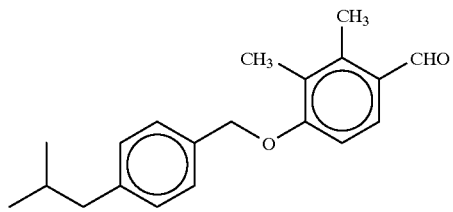

A mixture of 4-hydroxy-2,3-dimethylbenzaldehyde (220 mg), 4-isobutylbenzyl bromide (341 mg), potassium carbonate (1.38 g) and ethyl methyl ketone (10 ml) was refluxed for 6 hrs. After cooling, the reaction mixture was diluted with ethyl acetate, the solution was washed with di1 hydrochloric acid, water, successively, dried and evaporated. The residue was purified by column chromatography on silica gel (hexane:EtOAc=10:1) to give the title compound (383 mg) having the following physical data:

TLC: Rf 0.48 (hexane:EtOAc=5:1); NMR: δ7.64 (1H, d), 7.32 (1H, d), 7.16 (1H, d), 5.12 (2H, s), 2.60 (3H, s), 2.48 (2H, d), 2.24 (3H, s), 1.94–1.80 (1H, m), 0.90 (6H, d).

Reference Example 2
Synthesis of 4-(4-isobutylbenzyloxy)-2,3-dimethylbenzoic acid

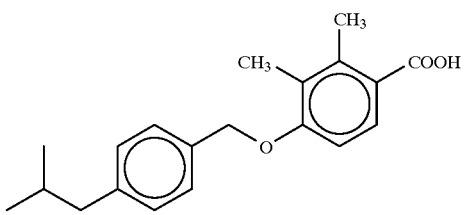

A solution of the aldehyde prepared in reference example 1 (380 mg) in acetone (5 ml) was cooled with ice. To the solution, Jones' reagent (2.67 N; 2 ml) was dropped and allowed to stand. The solution was stirred for 1.5 hrs at room temperature. The reaction was stopped by addition of isopropyl alcohol. The crystals deposited were washed with hexane, dried and purified by column chromatography on silica gel (hexane-EtOAc) to give the title compound (328 mg) having the following physical data: TLC: Rf 0.36 (hexane:EtOAc=2:1); NMR: δ7.80 (1H, d), 7.33 (1H, d), 7.15 (1H, d), 6.90 (1H, d), 5.09 (2H, s), 2.58 (3H, s), 2.48 (2H, d), 2.26 (3H, s), 0.91 (6H, d).

Reference Example 3
Synthesis of 4-[2-[4-(4-isobutylbenzyloxy)-2,3-dimethylbenzoylamino]phenoxy]butanoic acid ethyl ester

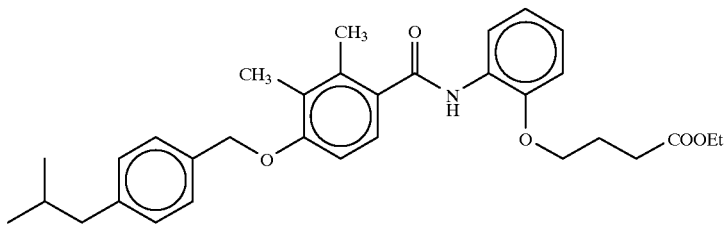

Oxalyl chloride (2 ml) was dropped to a solution of the carboxylic acid prepared in reference example 2 (325 mg) in methylene chloride (2 ml). The solution was stirred for 1 hr and evaporated. To an ice-cooled mixture of ethyl 4-(2-aminophenoxy)-butanoate (232 mg), pyridine (1 ml) and methylene chloride (15 ml), the above solution was dropped. The mixture was stirred for 30 mins at the same temperature and for 1 hr at room temperature. The reaction solution was washed with water, dried and evaporated. The residue was purified by column chromatography on silica gel (hexane:EtOAc=5:1) to give the title compound (383 mg) having the following physical data:

TLC: Rf 0.5 (hexane:EtOAc=3:1); NMR: δ 8.58–8.48 (1H, m), 8.05 (1H, s), 7.34 (H, d), 7.16 (1H, d), 7.08–6.96 (2H, m), 6.90–6.80 (2H, m), 5.07 (2H, s) 4.14–3.96 (4H, m), 2.49 (2H, d), 2.44 (3H, s), 1.18 (3H, t), 0.91 (6H, d).

Reference Example 4
Synthesis of 4-[2-[4-(4-isobutylbenzyloxy)-2,3-dimethylbenzoylamino]phenoxy]butanoic acid

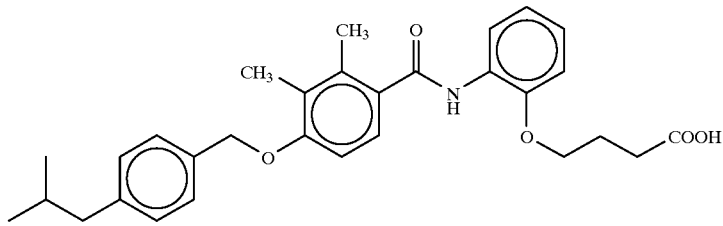

1N aq. Solution of lithium hydroxide (3 ml) was added to a solution of the ester prepared in Reference Example 3 (380 mg) in dimethoxyethane (8 ml). The mixture was stirred for 30 mins at 50° C. After reaction, the solution was neutralized with dil. hydrochloric acid and was extracted with ethyl acetate. The extract was dried and evaporated. The residue obtained was recrystallized from hexane to give the title compound (317 mg) having the following physical data:

TLC: Rf 0.26 (hexane:EtOAc=1:1): mp: 143° C.

Reference Example 5

By the similar procedure as reference examples 1, 2, 3 and 4, the following compound was made, 4-[2-[4-[1-(4-isobutylphenyl-)ethoxy)-2,3-dimethylbenzoylamino]phenoxy]butanoic acid, having the structural formula:

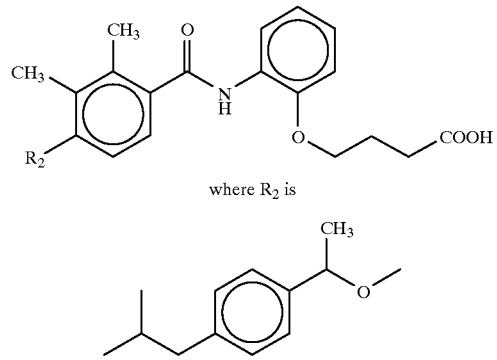

where $R_2$ is in which the Rf value is 0.37 (hexane:EtOAc=1:1), and the mass spectrum exhibited m/z values of 503, 345.

Reference Example 6
(−)-4-[2-(4-[1-(4-isobutylphenyl)ethoxy]-2,3-dimethylbenzoylamino phenoxy]butanoic acid The compound prepared above in reference example 5, (403 mg) and cinchonidine (2.36 g) were dissolved into acetone (70 ml) with heating. The solution was allowed to stand to give white crystals. The crystals were gathered by filtration and purified by recrystallization from acetone four times. The white crystals obtained were dissolved into chloroform. The solution was wahsed with dil. hydrochloric acid. The oily layer was washed with water, dried and evaporated to give the title compound having the following physical data:

Appearance: white crystal; Optical angle of rotation: $[a]_D$-39.6° (c=1, CHCl$_3$)

Reference Example 7
Sodium salt of (−)-4-[2-(4-[1-(4-isobutylphenyl)-ethoxy]-2,3-dimethylbenzoylamino)phenoxy]butanoic acid The compound prepared in Reference Example 6 was dissolved into methanol. The equivalent molar of an aq. Sodium hydroxide solution was added and evaporated to give the title compound having the following data: IR: ν 3050, 1750, 1580, 1560, 1510, 1445, 1260, 1090, 1020, 740 cm-1.

FORMULATION EXAMPLE

The following components are admixed in conventional method and punched out to obtain 100 tablets each containing 50 mg of active ingredient.

| | |
|---|---|
| 4-[2-[4-[1-(4-isobutylphenl)ethoxy)-2,3-dimethylbenzoylamino)phenoxy]butanoic acid | 5 g |
| Cellulose calcium gluconate (disintegrating agent) | 0.2 g |
| Magnesium stearate (lubricating agent) | 0.1 g |
| Microcrystaline cellulose | 4.7 g |

What is claimed is:

1. A method of treating prostatic cancer in patients who are in need of such treatment comprising the step of administering to such patients enhanced therapeutically effective amounts of the 5α-reductase inhibitor finasteride or a pharmaceutically acceptable ester or salt thereof in combination with the antiandrogen casodex.

2. A method according to claim 1 of treating prostatic cancer in patients who are in need of such treatment comprising the step of administering to such patients enhanced therapeutically effective amounts of the 5α-reductase inhibitor finasteride or a pharmaceutically acceptable ester or salt thereof, in combination with the antiandrogen casodex, wherein the combination is more effective than the use of either the 5α-reductase inhibitor or antiandrogen by itself.

3. A pharmaceutical composition for the treatment of prostatic cancer comprising enhanced therapeutically effective amounts of the 5α-reductase inhibitor finasteride and the antiandrogen casodex.

* * * * *